(12) United States Patent
King et al.

(10) Patent No.: US 6,307,026 B1
(45) Date of Patent: Oct. 23, 2001

(54) HUMANIZED ANTIBODIES DIRECTED AGAINST A33 ANTIGEN

(75) Inventors: David John King, Camberley; John Robert Adair, High Wycombe; Raymond John Owens, Henley-on-Thames, all of (GB)

(73) Assignee: Celltech Limited, Berkshire (GB)

( * ) Notice: Subject to any disclaimer, the term of this patent is extended or adjusted under 35 U.S.C. 154(b) by 0 days.

(21) Appl. No.: 08/976,183

(22) Filed: Nov. 21, 1997

Related U.S. Application Data

(62) Continuation of application No. 08/595,848, filed on Feb. 2, 1996, now abandoned, which is a continuation of application No. 08/256,325, filed as application No. PCT/GB93/02529 on Dec. 10, 1993, now abandoned.

(30) Foreign Application Priority Data

Dec. 10, 1992 (GB) .................................................. 9225853
Jul. 22, 1993 (GB) .................................................. 9315249

(51) Int. Cl.$^7$ ............................. C07K 16/30; C07K 16/28
(52) U.S. Cl. ................................ 530/387.3; 530/387.1; 530/387.7; 530/388.1; 530/388.2; 530/388.8; 530/391.1; 530/391.3
(58) Field of Search ............................. 530/387.1, 387.3, 530/388.2, 388.8, 387.7, 391.3

(56) References Cited

U.S. PATENT DOCUMENTS 5,091,542 * 2/1992 Ahlem et al. .
5,160,723 * 11/1992 Welt et al. .
5,225,538 * 7/1993 Capon et al. .
5,325,855 * 7/1994 Daghighian et al. .
5,530,101 * 6/1996 Queen et al. .

FOREIGN PATENT DOCUMENTS 0 239 400 * 9/1987 (EP) .
94/13805 * 6/1994 (WO) .

OTHER PUBLICATIONS

Tai, M.–S. et al. Biochemistry 29 (12): 8024–8030, 1990.*
Lacroix et al., "Monoclonal Antibodies to Lampbrush Chromosome Antigens of Pleurodeles Waltlii", *Chromosoma*, vol. 92:69–80, (1985).*
Welt et al., "Quantitative Analysis of Antibody Localization In Human Metastatic Colon Cancer: A Phase I Study Of Monoclonal Antibody A33", *Journal of Clinical Oncology*, vol. 8:1894–1906, (1990).*
Pyne et al., "Light And Elctron Microscopic Immunolocalization Of Two Nuclear Antigens In the Liver Of Pleurodeles Waltl Using Monoclonal Antibodies", *Biology of the Cell*, vol. 64:343–352, (1988).*
Queen et al., "A Humanized Antibody That Binds To The Interleukin 2 Receptor", *Proc. Natl. Acad. Sci. USA*, vol. 86:10029–10033, (1989).*
Riechmann et al., "Reshaping Human Antibodies For Therapy", *Nature*, vol. 332 323–327, (1988).*

* cited by examiner

Primary Examiner—Phillip Gambel
(74) Attorney, Agent, or Firm—Foley & Lardner

(57) ABSTRACT

A33 antigen binding proteins are described for use in the diagnosis or treatment of colorectal tumors and metastases arising therefrom. The binding protein may be a humanized A33 antibody, including complete antibody molecules, fragments thereof, and particularly, multivalent monospecific proteins comprising two, three, four or more antibodies or fragments thereof, bound to each other by a cross-linking agent. For diagnosis or therapy, the humanized A33 antibody may be linked to a reporter or effector molecule.

19 Claims, 30 Drawing Sheets

FIG. 1

HEAVY CHAIN FORWARD PRIMERS

| | | |
|---|---|---|
| CH1 | 5'GCGCGCAAGCTTGCCGCCACCATGAAATGCAGCTGGGTCATSTTCTT | 47 |
| CH2 | 5'GCGCGCAAGCTTGCCGCCACCATGGGATGGAGCTRTATCATSYTCTT | 47 |
| CH3 | 5'GCGCGCAAGCTTGCCGCCACCATGAAGWTGTGGTTAAACTGGGTTTT | 47 |
| CH4 | 5'GCGCGCAAGCTTGCCGCCACCATGRACTTTGGGYTCAGCTTGRT | 44 |
| CH5 | 5'GCGCGCAAGCTTGCCGCCACCATGGACTCCAGGCTCAATTTAGTTTT | 47 |
| CH6 | 5'GCGCGCAAGCTTGCCGCCACCATGGCTGTCYTRGYGCTRCTCTTCTG | 47 |
| CH7 | 5'GCGCGCAAGCTTGCCGCCACCATGGRATGGAGCBGGRTCTTTMTCTT | 47 |
| CH8 | 5'GCGCGCAAGCTTGCCGCCACCATGAGAGTGCTGATTCTTTTGTG | 44 |
| CH9 | 5'GCGCGCAAGCTTGCCGCCACCATGGMTTGGGTGTGGAMCTTGCTATT | 47 |
| CH10 | 5'GCGCGCAAGCTTGCCGCCACCATGGGCAGACTTACATTCTCATTCCT | 47 |
| CH11 | 5'GCGCGCAAGCTTGCCGCCACCATGGATTTTGGGCTGATTTTTTTTATTG | 49 |
| CH12 | 5'GCGCGCAAGCTTGCCGCCACCATGATGGTGTTAAGTCTTCTGTACCT | 47 |

Hind3

HEAVY CHAIN BACK PRIMER V/C JUNCTION

| | | |
|---|---|---|
| CH13 | 5'CAGATGGGCCCTTCGTTGAGGCTGMRGAGACDGTGA | 36 |

LIGHT CHAIN FORWARD PRIMERS

| | | |
|---|---|---|
| CL1 | 5'GGACTGTTCGAAGCCGCCACCATGAAGTTGCCTGTTAGGCTGTTGGTGCT | 50 |
| CL2 | 5'GGACTGTTCGAAGCCGCCACCATGGAGWCAGACACACTCCTGYTATGGGT | 50 |
| CL3 | 5'GGACTGTTCGAAGCCGCCACCATGAGTGTGCTCACTCAGGTCCT | 44 |
| CL4 | 5'GGACTGTTCGAAGCCGCCACCATGAGGRCCCCTGCTCAGWTTYTTGG | 47 |
| CL5 | 5'GGACTGTTCGAAGCCGCCACCATGGATTTWCAGGTGCAGATTWTCAGCTT | 50 |
| CL6 | 5'GGACTGTTCGAAGCCGCCACCATGAGGTBCYYTGYTSAGYTYCTGRG | 47 |
| CL7 | 5'GGACTGTTCGAAGCCGCCACCATGGGCWTCAAGATGGAGTCACA | 44 |
| CL8 | 5'GGACTGTTCGAAGCCGCCACCATGTGGGGAYCTBTTTYCMMTTTTTCAAT | 50 |
| CL9 | 5'GGACTGTTCGAAGCCGCCACCATGGTRTCCWCASCTCAGTTCCTT | 45 |
| CL10 | 5'GGACTGTTCGAAGCCGCCACCATGTATATATGTTTGTTGTCTATTTC | 47 |
| CL11 | 5'GGACTGTTCGAAGCCGCCACCATGGAAGCCCCAGCTCAGCTTCTCTT | 47 |

KAPPA LIGHT CHAIN BACK PRIMER V/C JUNCTION

| | | |
|---|---|---|
| CL12 | 5'GGATACAGTTGGTGCAGCATCCGTACGTTT 3' | 30 |

SplI

KEY: M=A/C, R=A/G, W=A/T, S=C/G, Y=T/C, B=T/G, D=A,G,T, H=A,C,T

FIG. 3(i)

A. LIGHT CHAIN

```
        T
ATG GGC ATC AAG ATG GAG TCA CAG ACC CAG GTC TTT GTA TTC GTG TTG CTC TGG
 M   G   I   K   M   E   S   Q   T   Q   V   F   V   F   V   L   L   W
                          F
TTG TCT GGT GTT GAT GGA GAC ATT GTG ATG ACC CAG TCT CAA AAA TTC ATG TCC
 L   S   G   V   D   G   D   I   V   M   T   Q   S   Q   K   F   M   S
                           1                                  10
ACA TCA GTA GGA GAC AGG GTC AGC ATC ACC TGC AAG GCC AGT CAG AAT GTT CGT
 T   S   V   G   D   R   V   S   I   T   C   K   A   S   Q   N   V   R
                              20                                      30
ACT GTT GTA GCC TGG TAT CAA CAG AAA CCA GGG CAG TCT CCT AAA ACA CTG ATT
 T   V   V   A   W   Y   Q   Q   K   P   G   Q   S   P   K   T   L   I
                                    40
TAC TTG GCC TCC AAC CGG CAC ACT GGA GTC CCT GAT CGC TTC ACA GGC AGT GGA
 Y   L   A   S   N   R   H   T   G   V   P   D   R   F   T   G   S   G
     50                                      60
TCT GGG ACA GAT TTC ACT CTC ACC ATT AGC AAT GTG CAA TCT GAA GAC CTG GCA
 S   G   T   D   F   T   L   T   I   S   N   V   Q   S   E   D   L   A
             70                                      80
GAT TAT TTC TGT CTG CAA CAT TGG AGT TAT CCT CTC ACG TTC GGC TCG GGG ACA
 D   Y   F   C   L   Q   H   W   S   Y   P   L   T   F   G   S   G   T
                         90                                 100
AAG TTG GAA GTA AAA CGT
 K   L   E   V   K   R
                 108
```

FIG. 3(ii)

B. HEAVY CHAIN

```
                         T              A
CC ACC ATG AAC TTT GGG CTC AGC TTG GTT TTC CTT GTC CTA ATT TTA AAA GGT
      M   N   F   G   L   S   L   V   F   L   V   L   I   L   K   G
                          E           I
GTC CAG TGT GAA GTG AAG CTG GTG GAG TCT GGG GGA GGC TTA GTG AAG CCT GGA
 V   Q   C   E   V   K   L   V   E   S   G   G   G   L   V   K   P   G
             1                                      10
GGG TCC CTG AAA CTC TCC TGT GCA GCC TCT GGA TTC GCT TTC AGT ACC TAT GAC
 G   S   L   K   L   S   C   A   A   S   G   F   A   F   S   T   Y   D
                 20                                          30
ATG TCT TGG GTT CGC CAG ACT CCG GAG AAG AGG CTG GAG TGG GTC GCA ACC ATT
 M   S   W   V   R   Q   T   P   E   K   R   L   E   W   V   A   T   I
                              40                                     50
AGT AGT GGT GGT AGT TAC ACC TAC TAT TTA GAC AGT GTG AAG GGC CGA TTC ACC
 S   S   G   G   S   Y   T   Y   Y   L   D   S   V   K   G   R   F   T
     a                                  60
ATC TCC AGA GAC AGT GCC AGG AAC ACC CTA TAC CTG CAA ATG AGC AGT CTG AGG
 I   S   R   D   S   A   R   N   T   L   Y   L   Q   M   S   S   L   R
    70                                          80        a   b   c
TCT GAG GAC ACG GCC TTG TAT TAC TGT GCA CCG ACT ACG GTA GTC CCG TTT GCT
 S   E   D   T   A   L   Y   Y   C   A   P   T   T   V   V   P   F   A
                             90                                     100
                                          T       C
TAC TGG GGC CAA GGG ACT CTG GTC ACC GTC TCT GCA
 Y   W   G   Q   G   T   L   V   T   V   S   A
                                 110         113
```

FIG. 4

```
        BstB1
5'GCGGGACTGTTCGAAGCCGCCACC 3'
   3'CCTGACAAGCTTCGGCGGTGGTACAGACAGGGGTGGGTTCAGGAGCCTGAGGACGACGAC
     G  L  F  E  A  A  T  M  S  V  P  T  Q  V  L  G  L  L  L  L
   5'TGGCTTACAGATGCCAGATGTGATATCCAGATGACTCAGAGTCCAAGTAGTCTCAGTGTA
     ACCGAATGTCTACGGTCTACA 5'
     W  L  T  D  A  R  C  D  I  Q  M  T  Q  S  P  S  S  L  S  V
     AGTGTAGGTGATAGGGTAACT 3'
     TCACATCCACTATCCCATTGATAGTGAACATTCCGGTCAGTCTTACAAGCATGACAACAT
     S  V  G  D  R  V  T  I  T  C  K  A  S  Q  N  V  R  T  V  V

5'CAGCAGAAACCAGGTCTCGCCCCAAAAACTCTCATCTATTTGGCCTCCAAC
     CGGACCATAGTCGTCTTTGGTCCAGAGCGG 5'
     A  W  Y  Q  Q  K  P  G  L  A  P  K  T  L  I  Y  L  A  S  N
                    Xba1
     CGGCACACTGGAGTACCATCTAGATTCAGTGGTAGCGGTAGT 3'
                        TCTAAGTCACCATCGCCATCACCATGACTAAAGTGAAAG
     R  H  T  G  V  P  S  R  F  S  G  S  G  S  G  T  D  F  T  F

5'GATATCGCCACTTACTTCTGCCTGCAACATTGGAGT
     TGATAGTCATCAGAGGTCGGTCTTCTATAGCGGTGAATGAAGACGGAC 5'
     T  I  S  S  L  Q  P  E  D  I  A  T  A  F  C  L  Q  H  W  S
                                                        Sp11
     TATCCTCTCACGTTCGGTCAGGGTACTAAAGTAGAAGTAAAACGTACGGGCCGG 3'
                                       3'CTTCATTTTGCATGCCCGGCC 5'
     Y  P  L  T  F  G  Q  G  T  K  V  E  V  K  R  t  g  r
```

FIG. 5

```
          Hind3
5'GCGCGCAAGCTTGCCGCCACC 3'
3'CGCGCGTTCGAACGGCGGTGGTACCTTACCTCGACCCAGAAAGAGAAGAAGGACAGTCAT
    A  R  K  L  A  A  T  M  E  W  S  W  V  F  L  F  F  L  S  V
           5'GTCCATTCTGAGGTGCAGCTGCTGGAGTCTGGAGGAGGACTGGTGCAGCCT
TGATGTCCTCAGGTAAGACTCCACGTCGAC 5'
    T  T  G  V  H  S  E  V  Q  L  L  E  S  G  G  G  L  V  Q  P
GGAGGATCTCTGAGACTGTCTTGTGCAGCATCTGGATTCGCTTTC 3'
                       3'CGTCGTAGACCTAAGCGAAAGTCATGGATACTGTAC
  G  G  S  L  R  L  S  C  A  A  S  G  F  A  F  S  T  Y  D  M
                             Xho1
                                  5'GTGGCAACCATTAGTAGTGGT
AGAACCCACTCTGTCCGTGGACCTTTTCCTGAGCTCACCCACCGTTGGTAATCATCACCA 5'
  S  W  V  R  Q  A  P  G  K  G  L  E  W  V  A  T  I  S  S  G GGTAGTTACACCTACTATTTAGACAGTGTGAAGGGAAGATTCACAATTTCCAGAGACTCT
                                             3'AGGTCTCTGAGA
  G  S  Y  T  Y  Y  L  D  S  V  K  G  R  F  T  I  S  R  D  S AGCAAGAAT 3'
TCGTTCTTATGTGACATGGACGTCTACTTAAGAGACGTCCGTCTCCTGAGACGTTAAATG
  S  K  N  T  L  Y  L  Q  M  N  S  L  Q  A  E  D  S  A  I  Y 5'TGTGCACCGACTACGGTAGTCCCGTTTGCTTACTGGGGACAGGGAACACTGGTGACA
ATGACACGTGGCTGATGCCATCAG 5'
  Y  C  A  P  T  T  V  V  P  F  A  Y  W  G  Q  G  T  L  V  T
                 Apa1
GTGTCTTCTGCCTCAACGAAGGGCCCGCGCGC 3'
          3'GAGTTGCTTCCCGGGCGCGCG 5'
  V  S  S  a  s  t  k  g  p  r
```

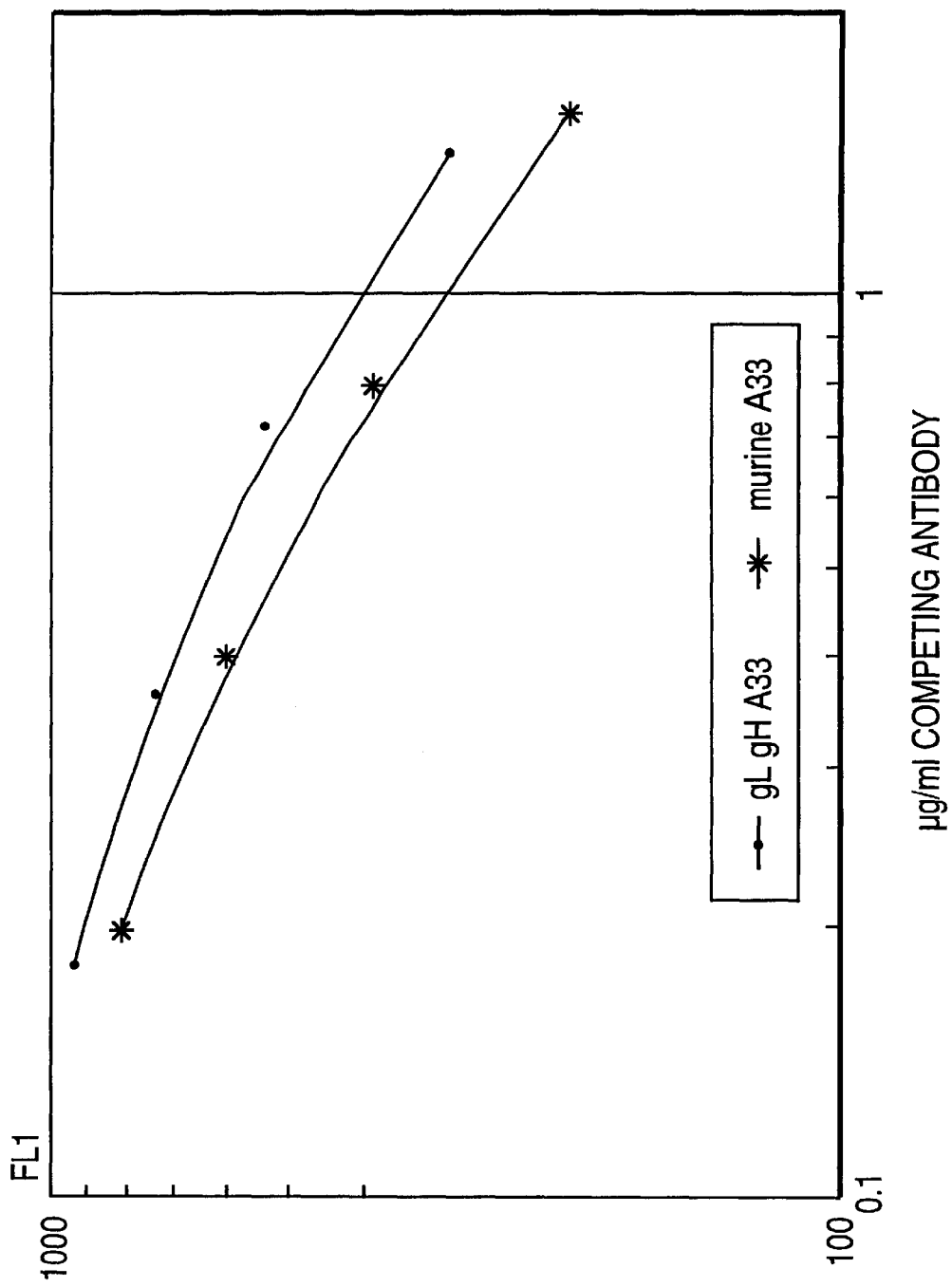

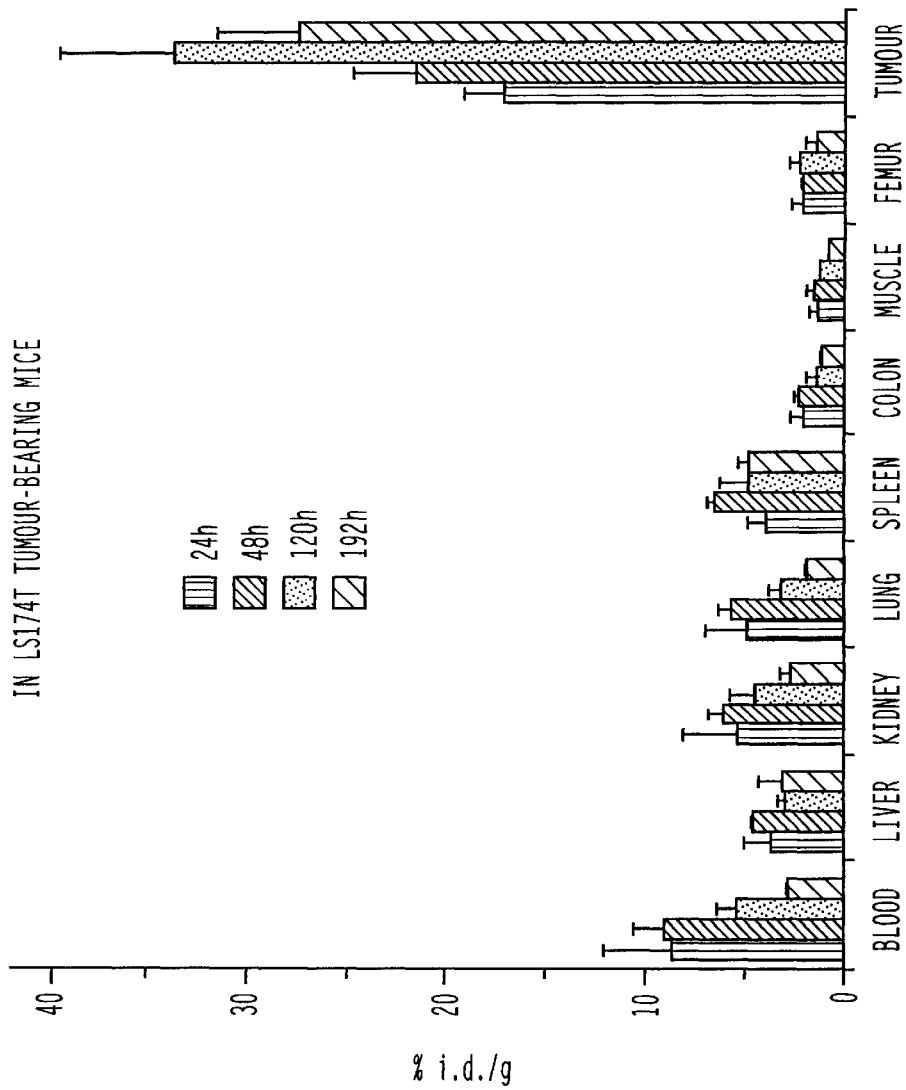

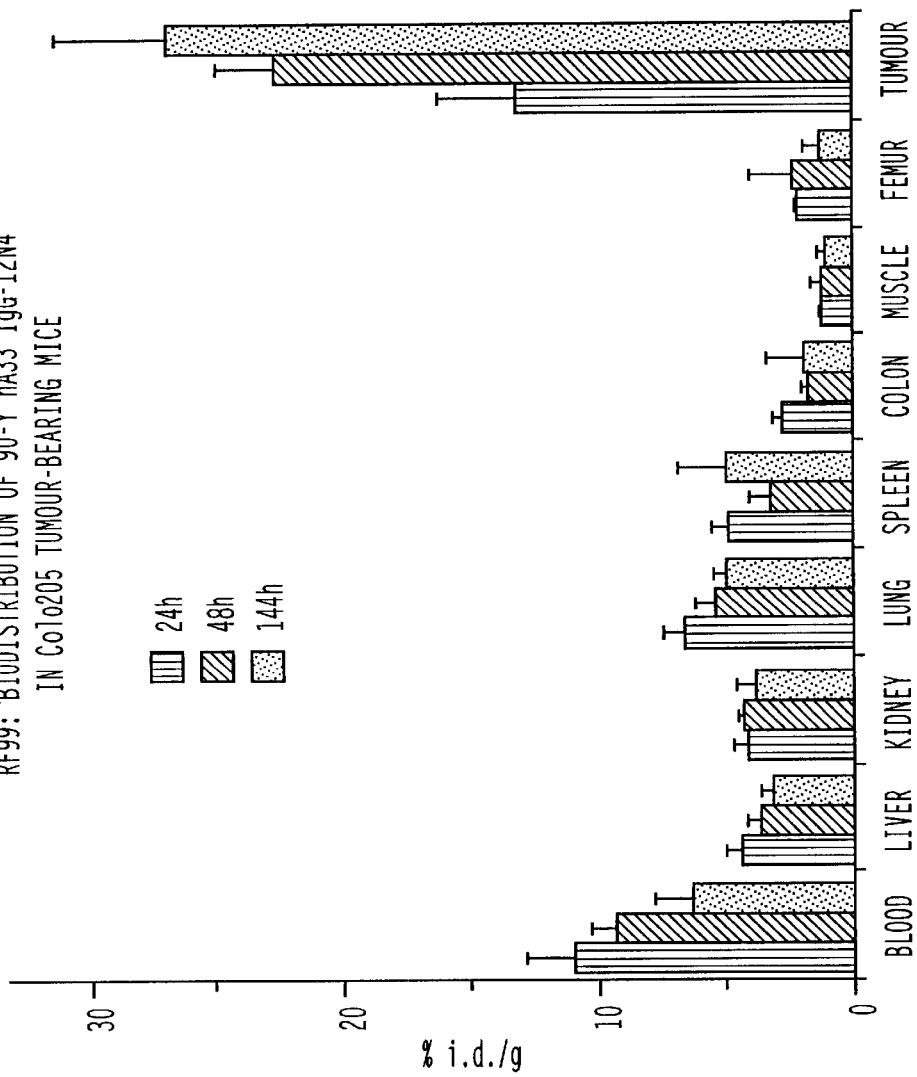

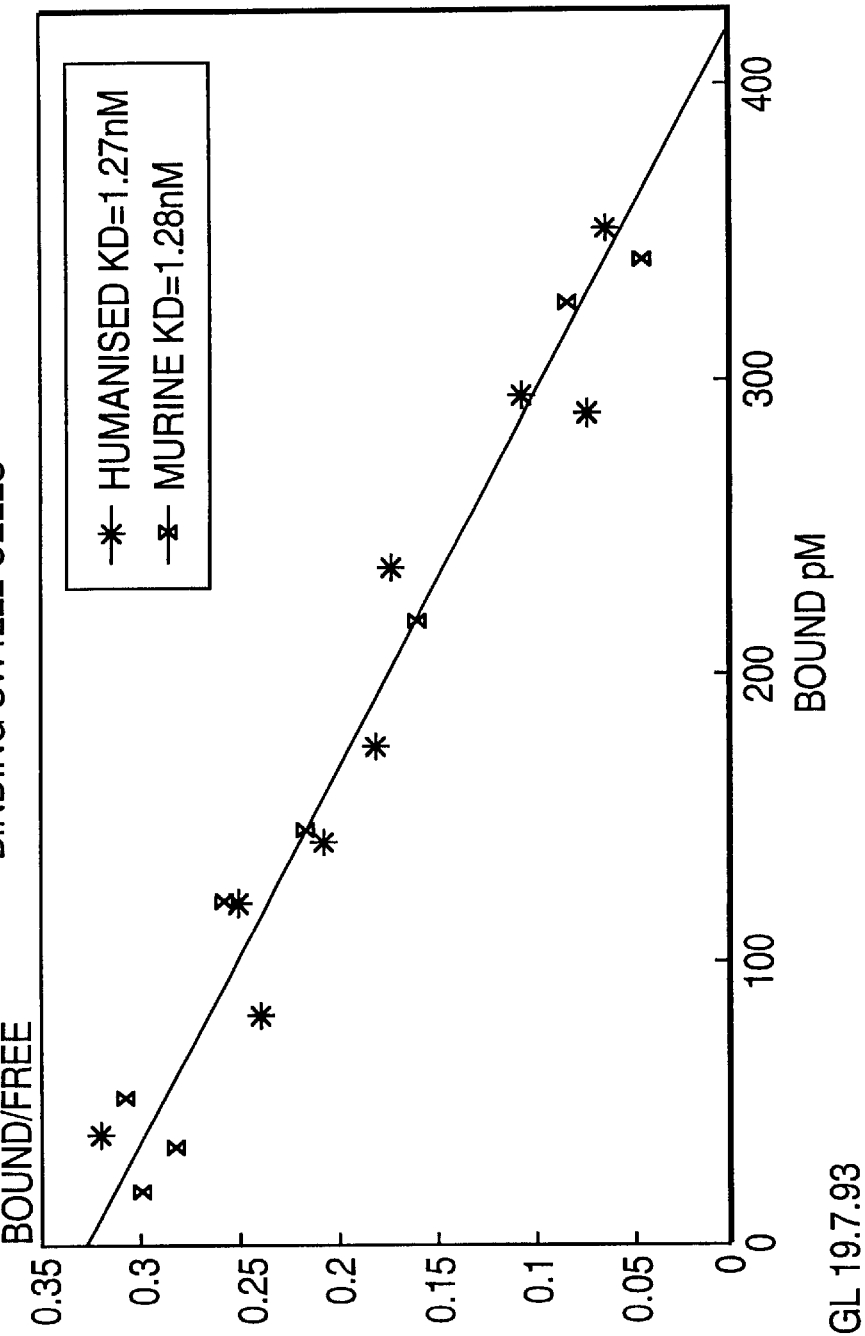

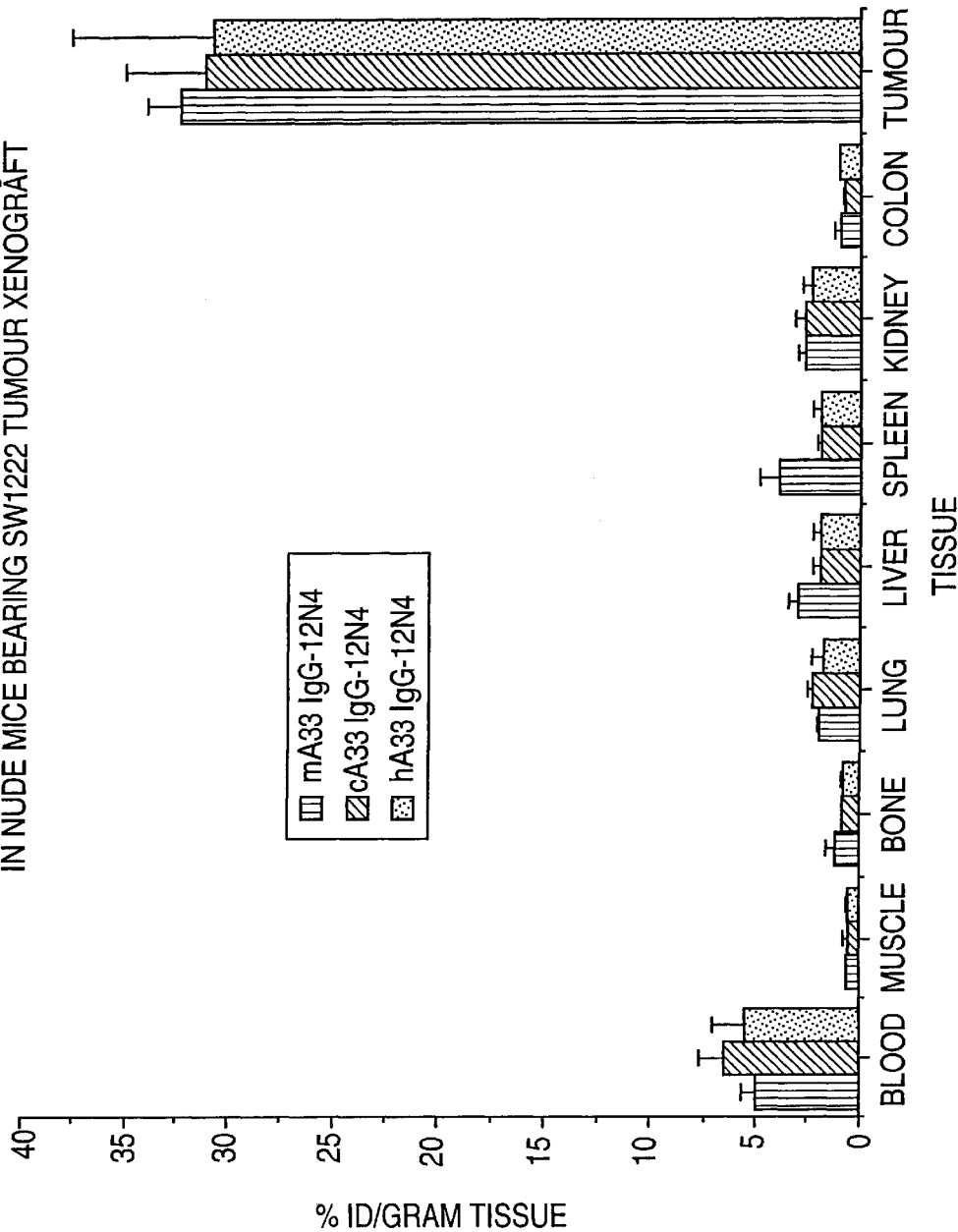

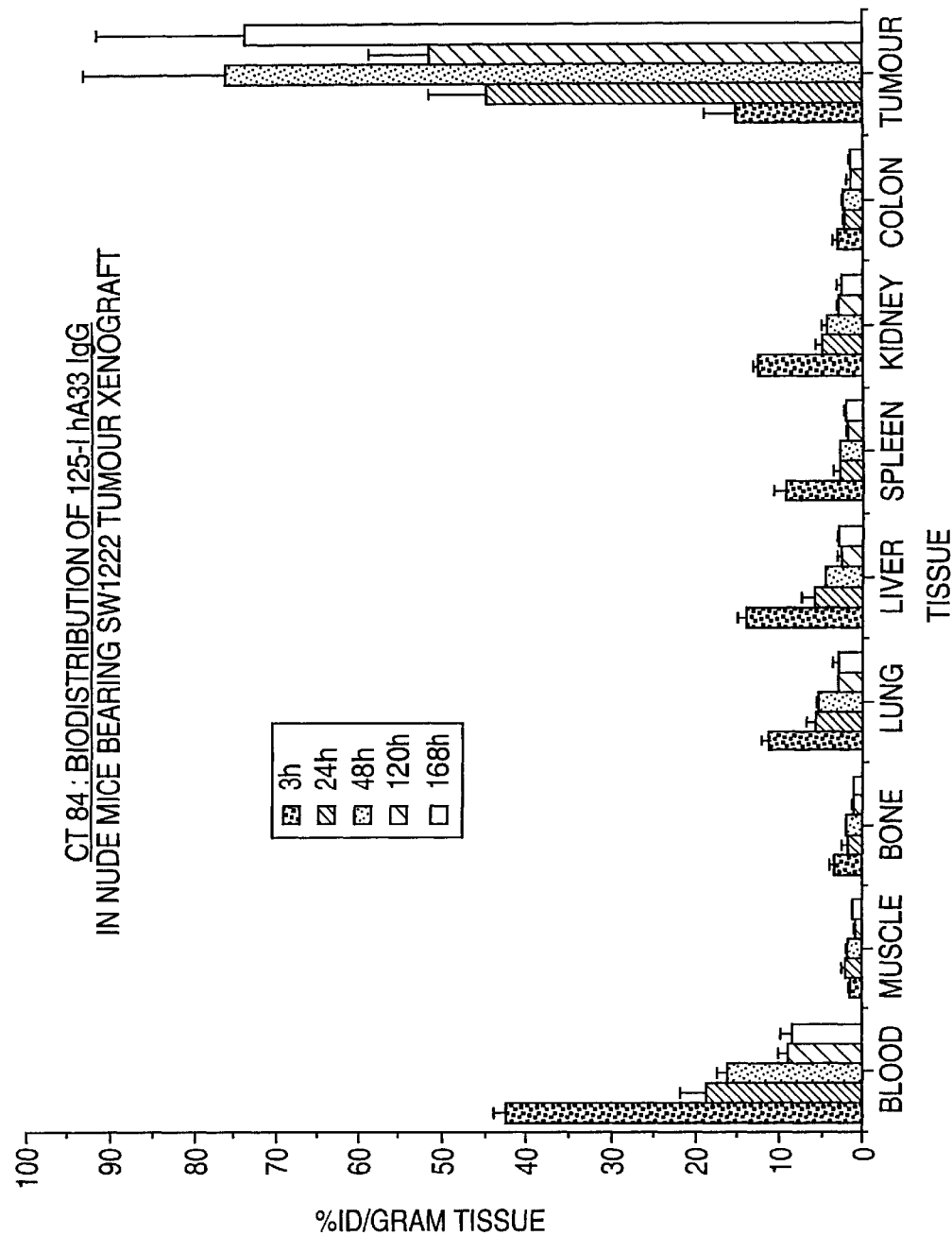

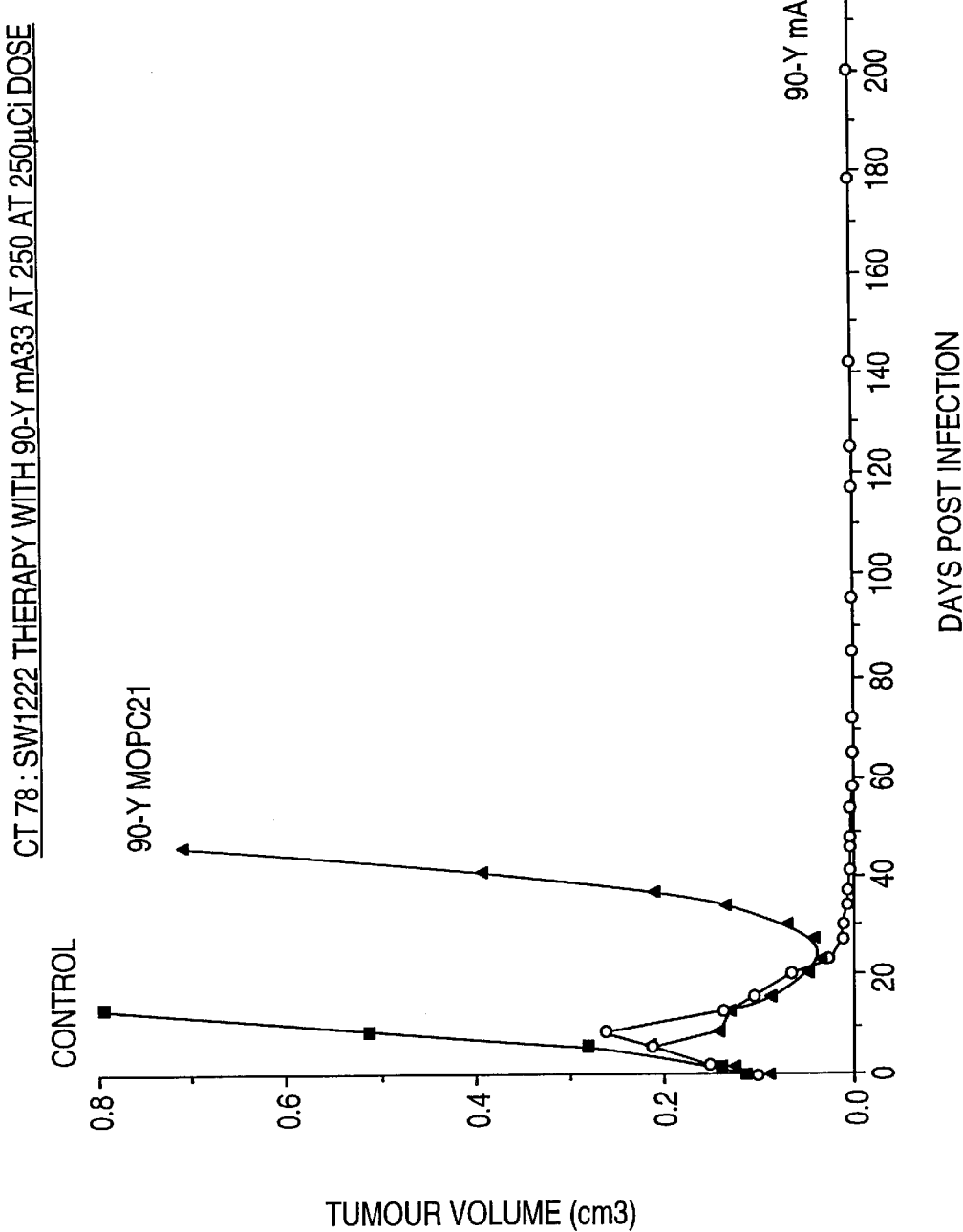

FIG. 14  Cross-linking of hA33 Fab' to DFM
HPLC gel filtration analysis
a) Reaction mix
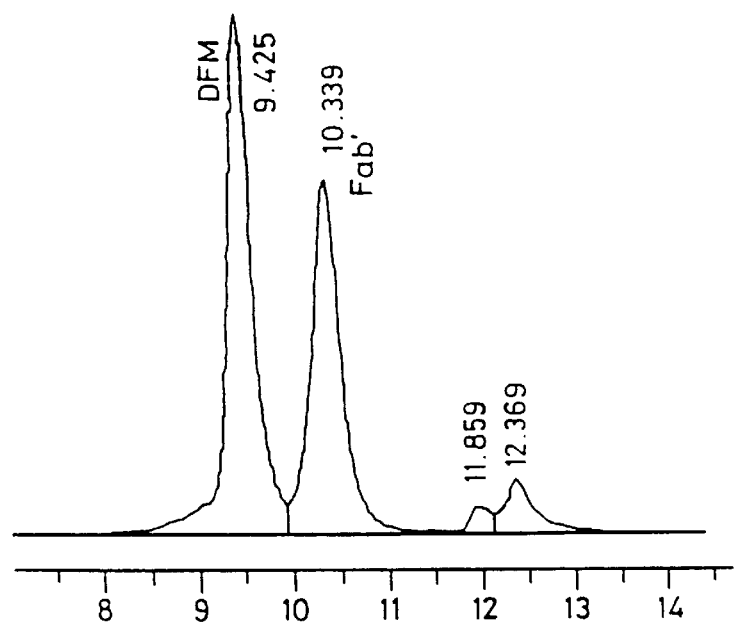
b) Purified DFM
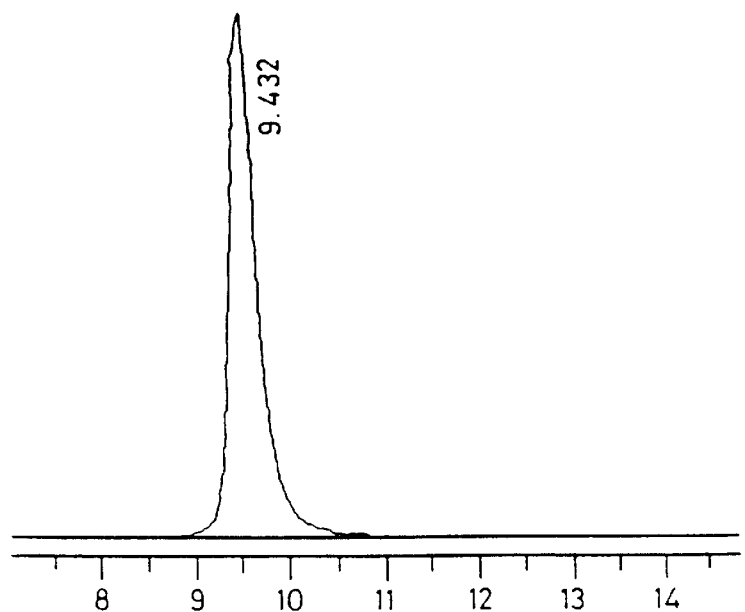

FIG. 15  Cross-linking of hA33 Fab' to TFM with CT557
HPLC gel filtration analysis
a) Reaction mix
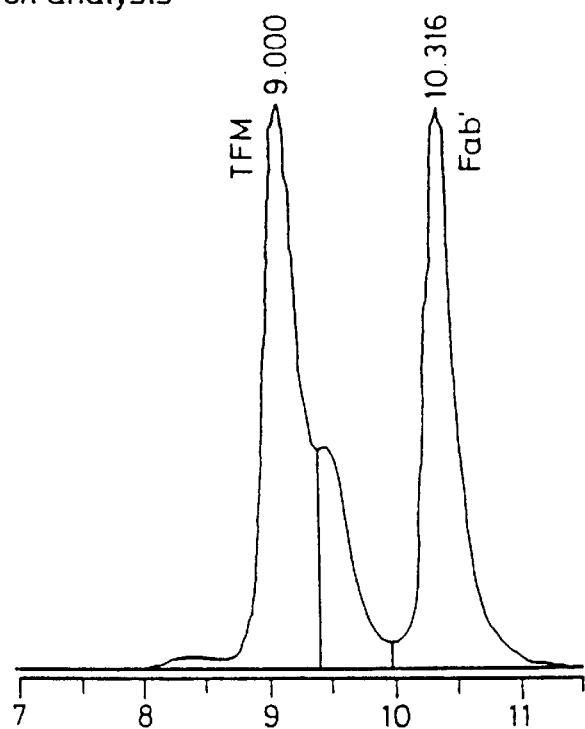
b) Purified TFM
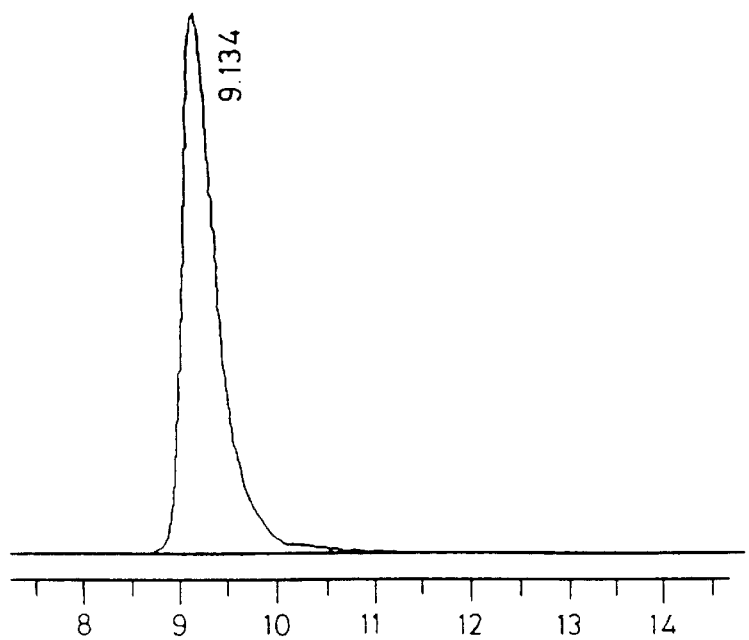

FIG. 16  Cross-linking of hA33 Fab' to TFM with CT998
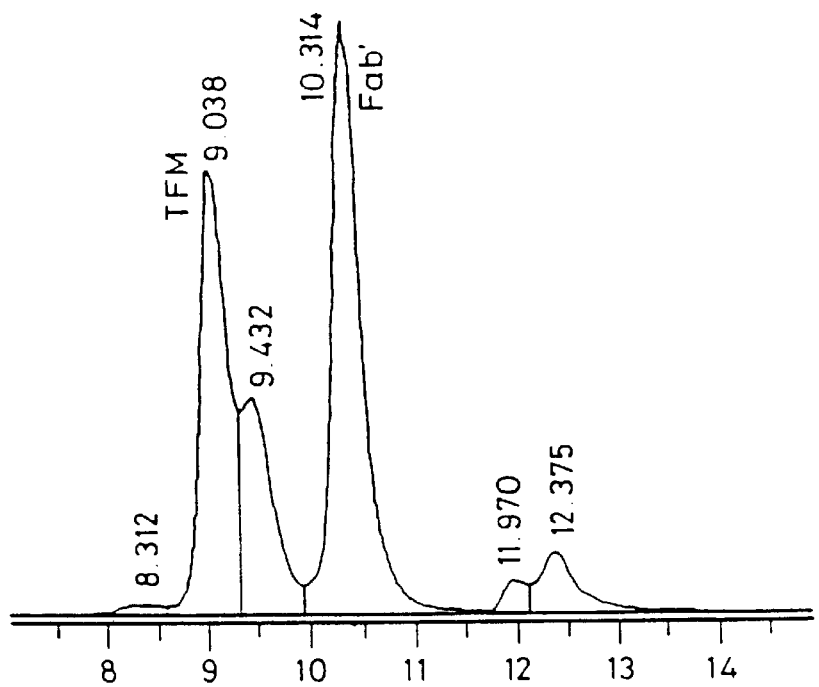

SDS-PAGE of hA33 Fab' Cross-linking

1  Molecular weight markers 2  hA33 Fab'

3  hA33 DFM reaction mix 4  hA33 DFM reaction mix 5  hA33 TFM(CT557) reaction mix 6  hA33 TFM(CT557) reaction mix 7  hA33 TFM(CT998) reaction mix 8  hA33 TFM(CT557) Purified

FIG. 27

Non-Reduced Western Blot Of 30° C And 46° C Extractions On Fermentation Cells

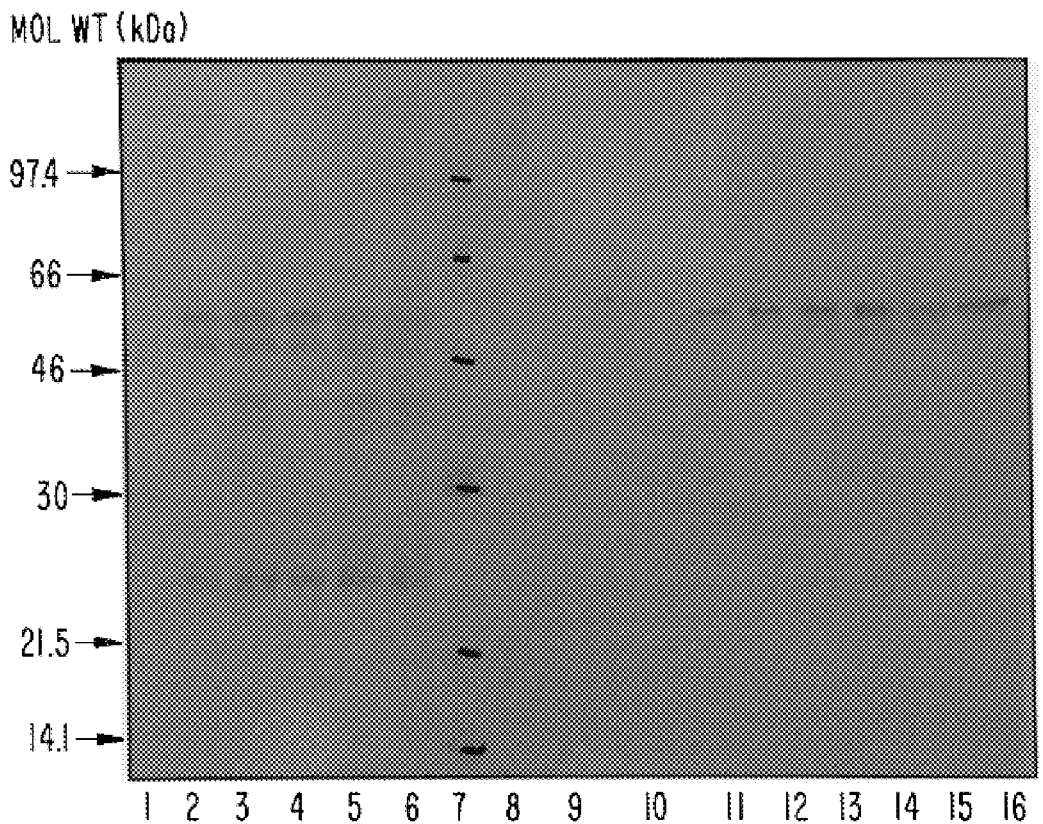

Non-reduced Western blot of extractions performed in Tris/EDTA at 30° C and 46° C on cell samples taken over the course of a fermentation from induction to harvest.

Lane 1:    30° C – Preinduction Cells
Lane 2-6:  30° C extraction on samples taken 8.3, 9.3, 13.5, 14.8 and 20.8 hours after induction
Lane 7:    Molecular Weight Markers
Lane 8:    46° C – Preinduction Cells
Lane 9-16: 46° C extractions on samples taken 2, 4.8, 5.8, 8.3, 9.3, 13.5, 14.8 and 20.8 hours after extraction COMPETITION ASSAY
DFMs OF GRAFTED A33 FROM E.coli AND NSO
VS FITC-mA33 FOR BINDING TO COLO 205

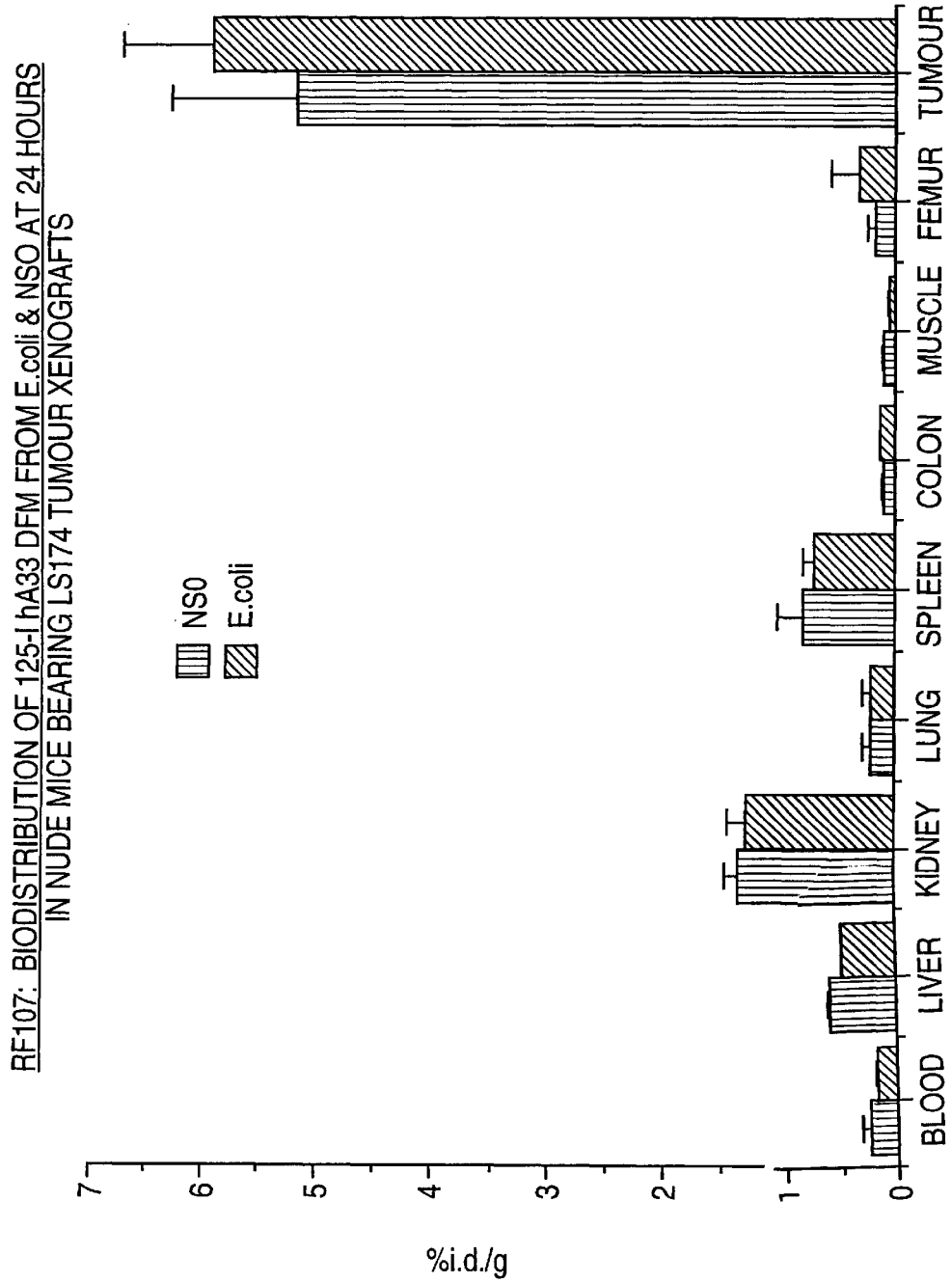

SEQUENCE LISTING

```
(1) GENERAL INFORMATION:

(iii) NUMBER OF SEQUENCES: 55

(2) INFORMATION FOR SEQ ID NO: 1:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "SYNTHETIC"

(xi) SEQUENCE DESCRIPTION: SEQ ID NO: 1:

AAAAAGACAG CTATCGCGAT TGCAGTGGCA CTGGCTGGTT TCGCTACCGT AGCGCAAGCT        60

GATATCCAGA TGACTCAG                                                     78

(2) INFORMATION FOR SEQ ID NO: 2:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "SYNTHETIC"

(xi) SEQUENCE DESCRIPTION: SEQ ID NO: 2:
```

```
CCGGCCCGTA CGTTTTACTT C                                                    21
```

(2) INFORMATION FOR SEQ ID NO: 3:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: other nucleic acid
        (A) DESCRIPTION:  /desc = "SYNTHETIC"

(xi) SEQUENCE DESCRIPTION: SEQ ID NO: 3:

```
AAAAAGACAG CTATCGCGAT TGCAGTGGCA CTGGCTGGTT TCGCTACCGT AGCGCAAGCT          60

GAGGTGCAGC TGCTGGAG                                                        78
```

(2) INFORMATION FOR SEQ ID NO: 4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION:  /desc = "SYNTHETIC"

(xi) SEQUENCE DESCRIPTION: SEQ ID NO: 4:

```
GCGCGCGGGC CCTTCGTTGA G                                                    21
```

(2) INFORMATION FOR SEQ ID NO: 5:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: other nucleic acid
        (A) DESCRIPTION:  /desc = "SYNTHETIC"

(xi) SEQUENCE DESCRIPTION: SEQ ID NO: 5:

```
GCGCGCAAGC TTGCCGCCAC CATGAAATGC AGCTGGGTCA TSTTCTT                        47
```

(2) INFORMATION FOR SEQ ID NO: 6:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: other nucleic acid
        (A) DESCRIPTION:  /desc = "SYNTHETIC"

(xi) SEQUENCE DESCRIPTION: SEQ ID NO: 6:

```
GCGCGCAAGC TTGCCGCCAC CATGGGATGG AGCTRTATCA TSYTCTT                        47
```

(2) INFORMATION FOR SEQ ID NO: 7:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: other nucleic acid (A) DESCRIPTION: /desc = "SYNTHETIC"

(xi) SEQUENCE DESCRIPTION: SEQ ID NO: 7:

GCGCGCAAGC TTGCCGCCAC CATGAAGWTG TGGTTAAACT GGGTTTT                47

(2) INFORMATION FOR SEQ ID NO: 8:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC"

(xi) SEQUENCE DESCRIPTION: SEQ ID NO: 8:

GCGCGCAAGC TTGCCGCCAC CATGRACTTT GGGYTCAGCT TGRT                   44

(2) INFORMATION FOR SEQ ID NO: 9:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC"

(xi) SEQUENCE DESCRIPTION: SEQ ID NO: 9:

GCGCGCAAGC TTGCCGCCAC CATGGACTCC AGGCTCAATT TAGTTTT                47

(2) INFORMATION FOR SEQ ID NO: 10:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC"

(xi) SEQUENCE DESCRIPTION: SEQ ID NO: 10:

GCGCGCAAGC TTGCCGCCAC CATGGCTGTC YTRGYGCTRC TCTTCTG                47

(2) INFORMATION FOR SEQ ID NO: 11:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC"

(xi) SEQUENCE DESCRIPTION: SEQ ID NO: 11:

GCGCGCAAGC TTGCCGCCAC CATGGRATGG AGCBGGRTCT TTMTCTT                47

(2) INFORMATION FOR SEQ ID NO: 12:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: other nucleic acid
            (A) DESCRIPTION:   /desc = "SYNTHETIC"

(xi) SEQUENCE DESCRIPTION: SEQ ID NO: 12:

GCGCGCAAGC TTGCCGCCAC CATGAGAGTG CTGATTCTTT TGTG                44

(2) INFORMATION FOR SEQ ID NO: 13:

(i) SEQUENCE CHARACTERISTICS:
            (A) LENGTH: 47 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "SYNTHETIC"

(xi) SEQUENCE DESCRIPTION: SEQ ID NO: 13:

GCGCGCAAGC TTGCCGCCAC CATGGMTTGG GTGTGGAMCT TGCTATT            47

(2) INFORMATION FOR SEQ ID NO: 14:

(i) SEQUENCE CHARACTERISTICS:
            (A) LENGTH: 47 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "SYNTHETIC"

(xi) SEQUENCE DESCRIPTION: SEQ ID NO: 14:

GCGCGCAAGC TTGCCGCCAC CATGGGCAGA CTTACATTCT CATTCCT            47

(2) INFORMATION FOR SEQ ID NO: 15:

(i) SEQUENCE CHARACTERISTICS:
            (A) LENGTH: 49 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "SYNTHETIC"

(xi) SEQUENCE DESCRIPTION: SEQ ID NO: 15:

GCGCGCAAGC TTGCCGCCAC CATGGATTTT GGGCTGATTT TTTTTATTG          49

(2) INFORMATION FOR SEQ ID NO: 16:

(i) SEQUENCE CHARACTERISTICS:
            (A) LENGTH: 47 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "SYNTHETIC"

(xi) SEQUENCE DESCRIPTION: SEQ ID NO: 16:

GCGCGCAAGC TTGCCGCCAC CATGATGGTG TTAAGTCTTC TGTACCT            47

(2) INFORMATION FOR SEQ ID NO: 17:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: other nucleic acid
            (A) DESCRIPTION:    /desc = "SYNTHETIC"

(xi) SEQUENCE DESCRIPTION: SEQ ID NO: 17:

CAGATGGGCC CTTCGTTGAG GCTGMRGAGA CDGTGA                                         36

(2) INFORMATION FOR SEQ ID NO: 18:

(i) SEQUENCE CHARACTERISTICS:
            (A) LENGTH: 50 base pairs
            (B) TYPE: nucleic acid
            (C) STRANDEDNESS: single
            (D) TOPOLOGY: linear (ii) MOLECULE TYPE: other nucleic acid
            (A) DESCRIPTION:    /desc = "SYNTHETIC"

(xi) SEQUENCE DESCRIPTION: SEQ ID NO: 18:

GGACTGTTCG AAGCCGCCAC CATGAAGTTG CCTGTTAGGC TGTTGGTGCT                          50

(2) INFORMATION FOR SEQ ID NO: 19:

(i) SEQUENCE CHARACTERISTICS:
            (A) LENGTH: 50 base pairs
            (B) TYPE: nucleic acid
            (C) STRANDEDNESS: single
            (D) TOPOLOGY: linear (ii) MOLECULE TYPE: other nucleic acid
            (A) DESCRIPTION:    /desc = "SYNTHETIC"

(xi) SEQUENCE DESCRIPTION: SEQ ID NO: 19:

GGACTGTTCG AAGCCGCCAC CATGGAGWCA GACACACTCC TGYTATGGGT                          50

(2) INFORMATION FOR SEQ ID NO: 20:

(i) SEQUENCE CHARACTERISTICS:
            (A) LENGTH: 44 base pairs
            (B) TYPE: nucleic acid
            (C) STRANDEDNESS: single
            (D) TOPOLOGY: linear (ii) MOLECULE TYPE: other nucleic acid
            (A) DESCRIPTION:    /desc = "SYNTHETIC"

(xi) SEQUENCE DESCRIPTION: SEQ ID NO: 20:

GGACTGTTCG AAGCCGCCAC CATGAGTGTG CTCACTCAGG TCCT                                44

(2) INFORMATION FOR SEQ ID NO: 21:

(i) SEQUENCE CHARACTERISTICS:
            (A) LENGTH: 47 base pairs
            (B) TYPE: nucleic acid
            (C) STRANDEDNESS: single
            (D) TOPOLOGY: linear (ii) MOLECULE TYPE: other nucleic acid
            (A) DESCRIPTION:    /desc = "SYNTHETIC"

(xi) SEQUENCE DESCRIPTION: SEQ ID NO: 21:

GGACTGTTCG AAGCCGCCAC CATGAGGRCC CCTGCTCAGW TTYTTGG                             47

(2) INFORMATION FOR SEQ ID NO: 22:

(i) SEQUENCE CHARACTERISTICS:
            (A) LENGTH: 50 base pairs
            (B) TYPE: nucleic acid
            (C) STRANDEDNESS: single (D) TOPOLOGY: linear (ii) MOLECULE TYPE: other nucleic acid
            (A) DESCRIPTION:   /desc = "SYNTHETIC"

(xi) SEQUENCE DESCRIPTION: SEQ ID NO: 22:

GGACTGTTCG AAGCCGCCAC CATGGATTTW CAGGTGCAGA TTWTCAGCTT              50

(2) INFORMATION FOR SEQ ID NO: 23:

(i) SEQUENCE CHARACTERISTICS:
            (A) LENGTH: 47 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "SYNTHETIC"

(xi) SEQUENCE DESCRIPTION: SEQ ID NO: 23:

GGACTGTTCG AAGCCGCCAC CATGAGGTBC YYTGYTSAGY TYCTGRG                 47

(2) INFORMATION FOR SEQ ID NO: 24:

(i) SEQUENCE CHARACTERISTICS:
            (A) LENGTH: 44 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "SYNTHETIC"

(xi) SEQUENCE DESCRIPTION: SEQ ID NO: 24:

GGACTGTTCG AAGCCGCCAC CATGGGCWTC AAGATGGAGT CACA                    44

(2) INFORMATION FOR SEQ ID NO: 25:

(i) SEQUENCE CHARACTERISTICS:
            (A) LENGTH: 50 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "SYNTHETIC"

(xi) SEQUENCE DESCRIPTION: SEQ ID NO: 25:

GGACTGTTCG AAGCCGCCAC CATGTGGGGA YCTBTTTYCM MTTTTTCAAT              50

(2) INFORMATION FOR SEQ ID NO: 26:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "SYNTHETIC"

(xi) SEQUENCE DESCRIPTION: SEQ ID NO: 26:

GGACTGTTCG AAGCCGCCAC CATGGTRTCC WCASCTCAGT TCCTT                   45

(2) INFORMATION FOR SEQ ID NO: 27:

(i) SEQUENCE CHARACTERISTICS:
            (A) LENGTH: 47 base pairs
            (B) TYPE: nucleic acid (C) STRANDEDNESS: single
            (D) TOPOLOGY: linear (ii) MOLECULE TYPE: other nucleic acid
            (A) DESCRIPTION:  /desc = "SYNTHETIC"

(xi) SEQUENCE DESCRIPTION: SEQ ID NO: 27:

GGACTGTTCG AAGCCGCCAC CATGTATATA TGTTTGTTGT CTATTTC          47

(2) INFORMATION FOR SEQ ID NO: 28:

(i) SEQUENCE CHARACTERISTICS:
            (A) LENGTH: 47 base pairs
            (B) TYPE: nucleic acid
            (C) STRANDEDNESS: single
            (D) TOPOLOGY: linear (ii) MOLECULE TYPE: other nucleic acid
            (A) DESCRIPTION:  /desc = "SYNTHETIC"

(xi) SEQUENCE DESCRIPTION: SEQ ID NO: 28:

GGACTGTTCG AAGCCGCCAC CATGGAAGCC CCAGCTCAGC TTCTCTT          47

(2) INFORMATION FOR SEQ ID NO: 29:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: other nucleic acid
            (A) DESCRIPTION:  /desc = "SYNTHETIC"

(xi) SEQUENCE DESCRIPTION: SEQ ID NO: 29:

GGATACAGTT GGTGCAGCAT CCGTACGTTT          30

(2) INFORMATION FOR SEQ ID NO: 30:

(i) SEQUENCE CHARACTERISTICS:
            (A) LENGTH: 416 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION:6..416

(xi) SEQUENCE DESCRIPTION: SEQ ID NO: 30:

CCACCATGAA CTTTGGGYTC AGCTTGRTTT TCCTTGTCCT AATTTTAAAA GGTGTCCAGT          60

GTGAAGTGAA GCTGGTGGAG TCTGGGGGAG GCTTAGTGAA GCCTGGAGGG TCCCTGAAAC         120

TCTCCTGTGC AGCCTCTGGA TTCGCTTTCA GTACCTATGA CATGTCTTGG GTTCGCCAGA         180

CTCCGGAGAA GAGGCTGGAG TGGGTCGCAA CCATTAGTAG TGGTGGTAGT TACACCTACT         240

ATTTAGACAG TGTGAAGGGC CGATTCACCA TCTCCAGAGA CAGTGCCAGG AACACCCTAT         300

ACTACCTGCA AATGAGCAGT CTGAGGTCTG AGGACACGGC CTTGTATTAC TGTGCACCGA         360

CTACGGTAGT CCCGTTTGCT TACTGGGGCC AAGGGACTCT GGTCACYGTC TCYGCA            416

(2) INFORMATION FOR SEQ ID NO: 31:

(i) SEQUENCE CHARACTERISTICS:
            (A) LENGTH: 136 amino acids
            (B) TYPE: amino acid (C) STRANDEDNESS: single
        (D) TOPOLOGY: linear (ii) MOLECULE TYPE: protein (xi) SEQUENCE DESCRIPTION: SEQ ID NO: 31:

Met Asn Phe Gly Leu Ser Leu Val Phe Leu Val Leu Ile Leu Lys Gly
1               5                   10                  15

Val Gln Cys Glu Val Lys Leu Val Glu Ser Gly Gly Gly Leu Val Lys
            20                  25                  30

Pro Gly Gly Ser Leu Lys Leu Ser Cys Ala Ala Ser Gly Phe Ala Phe
        35                  40                  45

Ser Thr Tyr Asp Met Ser Trp Val Arg Gln Thr Pro Glu Lys Arg Leu
    50                  55                  60

Glu Trp Val Ala Thr Ile Ser Ser Gly Gly Ser Tyr Thr Tyr Tyr Leu
65                  70                  75                  80

Asp Ser Val Lys Gly Arg Phe Thr Ile Ser Arg Asp Ser Ala Arg Asn
                85                  90                  95

Thr Leu Tyr Leu Gln Met Ser Ser Leu Arg Ser Glu Asp Thr Ala Leu
            100                 105                 110

Tyr Tyr Cys Ala Pro Thr Thr Val Val Pro Phe Ala Tyr Trp Gly Gln
        115                 120                 125

Gly Thr Leu Val Thr Val Ser Ala
    130                 135

(2) INFORMATION FOR SEQ ID NO: 32:

(i) SEQUENCE CHARACTERISTICS:
        (A) LENGTH: 136 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 32:

Met Asn Phe Gly Phe Ser Leu Ile Phe Leu Val Leu Ile Leu Lys Gly
1               5                   10                  15

Val Gln Cys Glu Val Lys Leu Val Glu Ser Gly Gly Gly Leu Val Lys
            20                  25                  30

Pro Gly Gly Ser Leu Lys Leu Ser Cys Ala Ala Ser Gly Phe Ala Phe
        35                  40                  45

Ser Thr Tyr Asp Met Ser Trp Val Arg Gln Thr Pro Glu Lys Arg Leu
    50                  55                  60

Glu Trp Val Ala Thr Ile Ser Ser Gly Gly Ser Tyr Thr Tyr Tyr Leu
65                  70                  75                  80

Asp Ser Val Lys Gly Arg Phe Thr Ile Ser Arg Asp Ser Ala Arg Asn
                85                  90                  95

Thr Leu Tyr Leu Gln Met Ser Ser Leu Arg Ser Glu Asp Thr Ala Leu
            100                 105                 110

Tyr Tyr Cys Ala Pro Thr Thr Val Val Pro Phe Ala Tyr Trp Gly Gln
        115                 120                 125

Gly Thr Leu Val Thr Val Ser Ala
    130                 135

(2) INFORMATION FOR SEQ ID NO: 33:

(i) SEQUENCE CHARACTERISTICS:
        (A) LENGTH: 136 amino acids (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 33:

Met Asn Phe Gly Leu Ser Leu Ile Phe Leu Val Leu Ile Leu Lys Gly
1               5                   10                  15

Val Gln Cys Glu Val Lys Leu Val Glu Ser Gly Gly Leu Val Lys
                20                  25                  30

Pro Gly Gly Ser Leu Lys Leu Ser Cys Ala Ala Ser Gly Phe Ala Phe
            35                  40                  45

Ser Thr Tyr Asp Met Ser Trp Val Arg Gln Thr Pro Glu Lys Arg Leu
    50                  55                  60

Glu Trp Val Ala Thr Ile Ser Ser Gly Gly Ser Tyr Thr Tyr Tyr Leu
65                  70                  75                  80

Asp Ser Val Lys Gly Arg Phe Thr Ile Ser Arg Asp Ser Ala Arg Asn
                85                  90                  95

Thr Leu Tyr Leu Gln Met Ser Ser Leu Arg Ser Glu Asp Thr Ala Leu
                100                 105                 110

Tyr Tyr Cys Ala Pro Thr Thr Val Val Pro Phe Ala Tyr Trp Gly Gln
            115                 120                 125

Gly Thr Leu Val Thr Val Ser Ala
130                 135

(2) INFORMATION FOR SEQ ID NO: 34:

(i) SEQUENCE CHARACTERISTICS:
        (A) LENGTH: 136 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 34:

Met Asn Phe Gly Phe Ser Leu Val Phe Leu Val Leu Ile Leu Lys Gly
1               5                   10                  15

Val Gln Cys Glu Val Lys Leu Val Glu Ser Gly Gly Gly Leu Val Lys
                20                  25                  30

Pro Gly Gly Ser Leu Lys Leu Ser Cys Ala Ala Ser Gly Phe Ala Phe
            35                  40                  45

Ser Thr Tyr Asp Met Ser Trp Val Arg Gln Thr Pro Glu Lys Arg Leu
    50                  55                  60

Glu Trp Val Ala Thr Ile Ser Ser Gly Gly Ser Tyr Thr Tyr Tyr Leu
65                  70                  75                  80

Asp Ser Val Lys Gly Arg Phe Thr Ile Ser Arg Asp Ser Ala Arg Asn
                85                  90                  95

Thr Leu Tyr Leu Gln Met Ser Ser Leu Arg Ser Glu Asp Thr Ala Leu
                100                 105                 110

Tyr Tyr Cys Ala Pro Thr Thr Val Val Pro Phe Ala Tyr Trp Gly Gln
            115                 120                 125

Gly Thr Leu Val Thr Val Ser Ala
130                 135

(2) INFORMATION FOR SEQ ID NO: 35:

(i) SEQUENCE CHARACTERISTICS:

(A) LENGTH: 396 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION:1..396

(xi) SEQUENCE DESCRIPTION: SEQ ID NO: 35:

```
ATGGGCATCA AGWTGGAGTC ACAGACCCAG GTCTTTGTAT TCGTGTTGCT CTGGTTGTCT      60

GGTGTTGATG GAGACATTGT GATGACCCAG TCTCAAAAAT TCATGTCCAC ATCAGTAGGA     120

GACAGGGTCA GCATCACCTG CAAGGCCAGT CAGAATGTTC GTACTGTTGT AGCCTGGTAT     180

CAACAGAAAC CAGGGCAGTC TCCTAAAACA CTGATTTACT TGGCCTCCAA CCGGCACACT     240

GGAGTCCCTG ATCGCTTCAC AGGCAGTGGA TCTGGGACAG ATTTCACTCT CACCATTAGC     300

AATGTGCAAT CTGAAGACCT GGCAGATTAT TTCTGTCTGC AACATTGGAG TTATCCTCTC     360

ACGTTCGGCT CGGGGACAAA GTTGGAAGTA AAACGT                               396
```

(2) INFORMATION FOR SEQ ID NO: 36:

(i) SEQUENCE CHARACTERISTICS:
        (A) LENGTH: 132 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 36:

```
Met Gly Ile Lys Met Glu Ser Gln Thr Gln Val Phe Val Phe Val Leu
1               5                   10                  15

Leu Trp Leu Ser Gly Val Asp Gly Asp Ile Val Met Thr Gln Ser Gln
            20                  25                  30

Lys Phe Met Ser Thr Ser Val Gly Asp Arg Val Ser Ile Thr Cys Lys
        35                  40                  45

Ala Ser Gln Asn Val Arg Thr Val Val Ala Trp Tyr Gln Gln Lys Pro
    50                  55                  60

Gly Gln Ser Pro Lys Thr Leu Ile Tyr Leu Ala Ser Asn Arg His Thr
65                  70                  75                  80

Gly Val Pro Asp Arg Phe Thr Gly Ser Gly Ser Gly Thr Asp Phe Thr
                85                  90                  95

Leu Thr Ile Ser Asn Val Gln Ser Glu Asp Leu Ala Asp Tyr Phe Cys
            100                 105                 110

Leu Gln His Trp Ser Tyr Pro Leu Thr Phe Gly Ser Gly Thr Lys Leu
        115                 120                 125

Glu Val Lys Arg
    130
```

(2) INFORMATION FOR SEQ ID NO: 37:

(i) SEQUENCE CHARACTERISTICS:
        (A) LENGTH: 132 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 37:

```
Met Gly Ile Lys Phe Glu Ser Gln Thr Gln Val Phe Val Phe Val Leu
 1               5                  10                  15
Leu Trp Leu Ser Gly Val Asp Gly Asp Ile Val Met Thr Gln Ser Gln
            20                  25                  30
Lys Phe Met Ser Thr Ser Val Gly Asp Arg Val Ser Ile Thr Cys Lys
        35                  40                  45
Ala Ser Gln Asn Val Arg Thr Val Val Ala Trp Tyr Gln Gln Lys Pro
    50                  55                  60
Gly Gln Ser Pro Lys Thr Leu Ile Tyr Leu Ala Ser Asn Arg His Thr
65                  70                  75                  80
Gly Val Pro Asp Arg Phe Thr Gly Ser Gly Ser Gly Thr Asp Phe Thr
                85                  90                  95
Leu Thr Ile Ser Asn Val Gln Ser Glu Asp Leu Ala Asp Tyr Phe Cys
            100                 105                 110
Leu Gln His Trp Ser Tyr Pro Leu Thr Phe Gly Ser Gly Thr Lys Leu
        115                 120                 125
Glu Val Lys Arg
        130
```

(2) INFORMATION FOR SEQ ID NO: 38:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "SYNTHETIC"

(xi) SEQUENCE DESCRIPTION: SEQ ID NO: 38:

```
GCGGGACTGT TCGAAGCCGC CACC                                          24
```

(2) INFORMATION FOR SEQ ID NO: 39:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "SYNTHETIC"

(xi) SEQUENCE DESCRIPTION: SEQ ID NO: 39:

```
TGGCTTACAG ATGCCAGATG TGATATCCAG ATGACTCAGA GTCCAAGTAG TCTCAGTGTA   60

AGTGTAGGTG ATAGGGTAAC T                                             81
```

(2) INFORMATION FOR SEQ ID NO: 40:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "SYNTHETIC"

(xi) SEQUENCE DESCRIPTION: SEQ ID NO: 40:

```
CAGCAGAAAC CAGGTCTCGC CCCAAAAACT CTCATCTATT TGGCCTCCAA CCGGCACACT   60

GGAGTACCAT CTAGATTCAG TGGTAGCGGT AGT                                93
```

(2) INFORMATION FOR SEQ ID NO: 41:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "SYNTHETIC"

(xi) SEQUENCE DESCRIPTION: SEQ ID NO: 41:

```
GATATCGCCA CTTACTTCTG CCTGCAACAT TGGAGTTATC CTCTCACGTT CGGTCAGGGT    60
ACTAAAGTAG AAGTAAAACG TACGGGCCGG                                     90
```

(2) INFORMATION FOR SEQ ID NO: 42:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "SYNTHETIC"

(iv) ANTI-SENSE: YES (xi) SEQUENCE DESCRIPTION: SEQ ID NO: 42:

```
ACATCTGGCA TCTGTAAGCC ACAGCAGCAG GAGTCCGAGG ACTTGGGTGG GGACAGACAT    60
GGTGGCGGCT TCGAACAGTC C                                              81
```

(2) INFORMATION FOR SEQ ID NO: 43:

(i) SEQUENCE CHARACTERISTICS:
        (A) LENGTH: 98 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "SYNTHETIC"

(iv) ANTI-SENSE: YES (xi) SEQUENCE DESCRIPTION: SEQ ID NO: 43:

```
GGCGAGACCT GGTTTCTGCT GATACCAGGC TACCAGGCTA CAACAGTACG AACATTCTGA    60
CTGGCCTTAC AAGTGATAGT TACCCTATCA CCTACACT                            98
```

(2) INFORMATION FOR SEQ ID NO: 44:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "SYNTHETIC"

(iv) ANTI-SENSE: YES (xi) SEQUENCE DESCRIPTION: SEQ ID NO: 44:

```
CAGGCAGAAG TAAGTGGCGA TATCTTCTGG CTGGAGAGTA CTGATAGTGA AAGTGAAATC    60
AGTACCACTA CCGCTACCAC TGAATCT                                        87
```

(2) INFORMATION FOR SEQ ID NO: 45:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC"

(iv) ANTI-SENSE: YES (xi) SEQUENCE DESCRIPTION: SEQ ID NO: 45:

CCGGCCCGTA CGTTTTACTT C                                                         21

(2) INFORMATION FOR SEQ ID NO: 46:

(i) SEQUENCE CHARACTERISTICS:
        (A) LENGTH: 138 amino acids
        (B) TYPE: amino acid
        (C) STRANDEDNESS: single
        (D) TOPOLOGY: linear (ii) MOLECULE TYPE: protein (iii) HYPOTHETICAL: YES (xi) SEQUENCE DESCRIPTION: SEQ ID NO: 46:

```
Gly Leu Phe Glu Ala Ala Thr Met Ser Val Pro Thr Gln Val Leu Gly
 1               5                  10                  15

Leu Leu Leu Leu Trp Leu Thr Asp Ala Arg Cys Asp Ile Gln Met Thr
            20                  25                  30

Gln Ser Pro Ser Ser Leu Ser Val Ser Val Gly Asp Arg Val Thr Ile
        35                  40                  45

Thr Cys Lys Ala Ser Gln Asn Val Arg Thr Val Val Ala Trp Tyr Gln
    50                  55                  60

Gln Lys Pro Gly Leu Ala Pro Lys Thr Leu Ile Tyr Leu Ala Ser Asn
65                  70                  75                  80

Arg His Thr Gly Val Pro Ser Arg Phe Ser Gly Ser Gly Ser Gly Thr
                85                  90                  95

Asp Phe Thr Phe Thr Ile Ser Ser Leu Gln Pro Glu Asp Ile Ala Thr
            100                 105                 110

Tyr Phe Cys Leu Gln His Trp Ser Tyr Pro Leu Thr Phe Gly Gln Gly
        115                 120                 125

Thr Lys Val Glu Val Lys Arg Thr Gly Arg
    130                 135
```

(2) INFORMATION FOR SEQ ID NO: 47:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC"

(xi) SEQUENCE DESCRIPTION: SEQ ID NO: 47:

GCGCGCAAGC TTGCCGCCAC C                                                         21

(2) INFORMATION FOR SEQ ID NO: 48:

(i) SEQUENCE CHARACTERISTICS:
    (A) LENGTH: 96 base pairs
    (B) TYPE: nucleic acid
    (C) STRANDEDNESS: single
    (D) TOPOLOGY: linear (ii) MOLECULE TYPE: other nucleic acid
    (A) DESCRIPTION:   /desc = "SYNTHETIC"

(xi) SEQUENCE DESCRIPTION: SEQ ID NO: 48:

GTCCATTCTG AGGTGCAGCT GCTGGAGTCT GGAGGAGGAC TGGTGCAGCC TGGAGGATCT    60

CTGAGACTGT CTTGTGCAGC ATCTGGATTC GCTTTC                              96

(2) INFORMATION FOR SEQ ID NO: 49:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "SYNTHETIC"

(xi) SEQUENCE DESCRIPTION: SEQ ID NO: 49:

GTGGCAACCA TTAGTAGTGG TGGTAGTTAC ACCTACTATT TAGACAGTGT GAAGGGAAGA    60

TTCACAATTT CCAGAGACTC TAGCAAGAAT                                     90

(2) INFORMATION FOR SEQ ID NO: 50:

(i) SEQUENCE CHARACTERISTICS:
        (A) LENGTH: 89 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "SYNTHETIC"

(xi) SEQUENCE DESCRIPTION: SEQ ID NO: 50:

TGTGCACCGA CTACGGTAGT CCCGTTTGCT TACTGGGAC AGGGAACACT GGTGACAGTG     60

TCTTCTGCCT CAACGAAGGG CCCGCGCGC                                      89

(2) INFORMATION FOR SEQ ID NO: 51:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "SYNTHETIC"

(iv) ANTI-SENSE: YES (xi) SEQUENCE DESCRIPTION: SEQ ID NO: 51:

CAGCTGCACC TCAGAATGGA CTCCTGTAGT TACTGACAGG AAGAAGAGAA AGACCCAGCT    60

CCATTCCATG GTGGCGGCAA GCTTGCGCGC                                     90

(2) INFORMATION FOR SEQ ID NO: 52:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: other nucleic acid
              (A) DESCRIPTION:   /desc = "SYNTHETIC"

(iv) ANTI-SENSE: YES (xi) SEQUENCE DESCRIPTION: SEQ ID NO: 52:

ACCACTACTA ATGGTTGCCA CCCACTCGAG TCCTTTTCC AGGTGCCTGTC TCACCCAAGA      60

CATGTCATAG GTACTGAAAG CGAATCCAGA TGCTGC                               96

(2) INFORMATION FOR SEQ ID NO: 53:

(i) SEQUENCE CHARACTERISTICS:
              (A) LENGTH: 96 base pairs
              (B) TYPE: nucleic acid
              (C) STRANDEDNESS: single
              (D) TOPOLOGY: linear (ii) MOLECULE TYPE: other nucleic acid
              (A) DESCRIPTION:   /desc = "SYNTHETIC"

(iv) ANTI-SENSE: YES (xi) SEQUENCE DESCRIPTION: SEQ ID NO: 53:

GACTACCGTA GTCGGTGCAC AGTAGTAAAT TGCAGAGTCC TCTGCCTGCA GAGAATTCAT      60

GTGCAGGTAC AGTGTATTCT TGCTAGAGTG TCTGGA                               96

(2) INFORMATION FOR SEQ ID NO: 54:

(i) SEQUENCE CHARACTERISTICS:
              (A) LENGTH: 21 base pairs
              (B) TYPE: nucleic acid
              (C) STRANDEDNESS: single
              (D) TOPOLOGY: linear (ii) MOLECULE TYPE: other nucleic acid
              (A) DESCRIPTION:   /desc = "SYNTHETIC"

(iv) ANTI-SENSE: YES (xi) SEQUENCE DESCRIPTION: SEQ ID NO: 54:

GCGCGCGGGC CCTTCGTTGA G                                                21

(2) INFORMATION FOR SEQ ID NO: 55:

(i) SEQUENCE CHARACTERISTICS:
              (A) LENGTH: 150 amino acids
              (B) TYPE: amino acid
              (C) STRANDEDNESS: single
              (D) TOPOLOGY: linear (ii) MOLECULE TYPE: protein (iii) HYPOTHETICAL: YES (xi) SEQUENCE DESCRIPTION: SEQ ID NO: 55:

Ala Arg Lys Leu Ala Ala Thr Met Glu Trp Ser Trp Val Phe Leu Phe
1               5                   10                  15

Phe Leu Ser Val Thr Thr Gly Val His Ser Glu Val Gln Leu Leu Glu
                20                  25                  30

Ser Gly Gly Gly Leu Val Gln Pro Gly Gly Ser Leu Arg Leu Ser Cys
            35                  40                  45

Ala Ala Ser Gly Phe Ala Phe Ser Thr Tyr Asp Met Ser Trp Val Arg
        50                  55                  60

Gln Ala Pro Gly Lys Gly Leu Glu Trp Val Ala Thr Ile Ser Ser Gly
65                  70                  75                  80

-continued

```
Gly Ser Tyr Thr Tyr Tyr Leu Asp Ser Val Lys Gly Arg Phe Thr Ile
             85              90                  95

Ser Arg Asp Ser Ser Lys Asn Thr Leu Tyr Leu Gln Met Asn Ser Leu
            100             105             110

Gln Ala Glu Asp Ser Ala Ile Tyr Tyr Cys Ala Pro Thr Val Val
            115             120             125

Pro Phe Ala Tyr Trp Gly Gln Gly Thr Leu Val Thr Val Ser Ser Ala
    130             135             140

Ser Thr Lys Gly Pro Arg
145             150
```

HUMANIZED ANTIBODIES DIRECTED AGAINST A33 ANTIGEN

This application is a continuation of application Ser. No. 08/595,848, filed Feb. 2, 1996 now abandoned, which is a continuation of application Ser. No. 08/256,375, filed on Oct. 4, 1994 now abandoned, which is the national phase of PCT/GB93/02529, filed Dec. 10, 1996.

FIELD OF THE INVENTION

This invention relates to antibody molecules having specificity for the epitope recognised by the murine monoclonal antibody A33, to processes for their preparation, to pharmaceutical compositions containing them and to their use, in medicine.

BACKGROUND TO THE INVENTION

The murine monoclonal antibody (MAb) A33, is an IgG2a/k which recognises a heat-stable, protease-resistant neuraminidase-resistant epitope which is homogeneously expressed in virtually all primary and metastatic colon cancers. The expression of the antigen is restricted to normal colonic mucosal epithelium and colonic carcinoma and it is not shed into the circulation (Welt et al., 1990). The antigen is expressed on a number of human tumour cell lines, including ASPC-1 and Colo205.

The A33 antibody internalises after binding to antigen. It has been shown to localise to tumours in vivo in patients with hepatic metastases of colorectal carcinoma (Welt et al., 1990). $^{131}$I labelled antibody (0.2 mg., n=3; 2 mg., n=8; 10 mg. n=3; 25 mg, n=3; 50 mg, n=3; labelled with 2–5 mCi) was administered i.v. to 20 patients 7–8 days prior to surgery. Selective mAb33 localisation to tumour tissue was demonstrated in 19 of the 20 patients. One week after administration tumour/liver ratios ranged from 6.9 to 100 while tumour/serum ratios ranged from 4.1 to 25.2. Studies with a control 125I MAb Ta99 (2 mg. dose, co-administered to three patients who received 2 mg. A33), showed that the tumour uptake of A33 was specific, with 2.3 to 45 fold higher uptake for A33.

However a human anti-mouse antibody (HAMA) response was detected in patients as early as day 7 in 8 patients and all patients developed a HAMA response by day 30. Initially the predominant HAMA was IgM but by day 30 IgG responses were also detected. The HAMA reactivity was not, however, restricted to the IgG2a isotype. Murine IgG1 and IgG3 could also be detected with patient serum. It can therefore be expected that the usefulness of the murine MAb A33 as a therapeutic agent in humans will be limited by the fact that the human subject will mount an immunological response to the MAb and will either remove it entirely or at least reduce its effectiveness.

Proposals have been made for making non-human MAbs less antigenic in humans. Such techniques can be generically termed "humanisation" techniques. These techniques generally involve the use of recombinant DNA technology to manipulate DNA sequences encoding the polypeptide chains of the antibody molecule. A simple form of humanisation involves the replacement of the constant regions of the murine antibody with those from a human antibody (Morrison et al., 1984, Whittle et al., 1987). A number of these chimeric mouse variable human constant region antibodies have been administered to patients. (Baker et al., 1991; Begent et al., 1990; Ghrayeb et al., 1991; Khazaeli A., 1992; Knox et al., 1990; LoBuglio et al., 1989; Meredith et al., 1991, 1992; Saleh et al., 1992; Trang et al., 1990). In general an immune response still develops against these chimeric antibodies although the level of the response is usually lower than that seen against the murine antibody and delayed in onset. In one case, chimeric 17-1A(γ1), the response seen has been remarkably low (LoBughio et al., 1989; Meredith et al., 1991; Trang et al. 1990) with only 1 of 16 patients treated showing a low level response. In the other examples approximately 50% of the patients treated develop a response which is predominantly against the murine variable region, including the binding site. The lowering of the level of the HAMA response to the chimeric antibodies leads to the expectation that further humanisation of the variable region outside of the antigen binding site may abolish the response to these regions and further reduce the response against the binding site.

A more complex form of humanisation of an antibody involves the re-design of the variable region domain so that the amino acids constituting the murine antibody binding site are integrated into the framework of a human antibody variable region (Jones eta., 1986). That this can be cone is a consequence of the close structural and sequence relationship between immunoglobulins from different species.

Within the variable region sequence it has been noticed that a number of non-contiguous sequences, three per domain, are particularly variable (termed hypervariable). This observed sequence variation between antibodies was postulated to provide the variability which enables antibodies ,o recognise and bind to a wide range of antigenic forms and the three hypervariable regions in each domain were termed the Complementarity Determining Regions (CDR's) (Wu and Kabat, 1970; Kabat et al., 1987). This proposal has been confirmed from structural studies where it is seen that for the most part the hypervariable sequences are associated on the surface as a set of loops which form a large surface patch and that these sequences are in contact with antigen in those cases where antigen-antibody complexes have been studied (Amit et al., 1986; Bhat et al., 1990; Boulot et al., 1987, 1990; Colman et al., 1987; Davies et al, 1989; Padlan et al., 1989; Poljak, 1991; Sheriff et al., 1987). In most but not all cases the CDRs correspond to, but extend a short way beyond, these structural loop regions.

Substitution of these hypervariable regions alone into a human antibody does not, in general, lead to the reconstitution of the binding affinity of the murine antibody (Verhoeyen et al., 1988; Riechmann et al., 1988).

Residues not identified in the loop or hypervariable regions must therefore contribute to antigen binding directly or indirectly by affecting antigen binding site topology, by inducing a stable packing of the individual variable domains, or by stabilising the inter-variable domain interaction. Methods for the identification of these key framework locations are available (eg. Adair et al., 1991; Kurrie et al., 1990; Law et al., 1991; Padlan, 1991; Queen et al., 1990; Winter, 1987).

The choice of human framework for the humanisation process can be based on the desire to use an antibody domain for which there is a known structure determined from X-ray crystallography, so that some positional information is available about framework amino acids, or to use a matched light and heavy chain pair, or to use a representative example from the various human subgroups, or simply to search the available human sequences and identify human antibody domains which have high homology to the variable domains of the mouse antibody in question.

Humanisation has led to the reconstitution of full antigen binding activity in a number of cases (Co et al., 1990, 1992;

Carter et al., 1992; Routledge et al., 1991; and International Patent Specifications Nos. WO 91/09967; WO 91/09968; and WO 92111383).

The reduction in immunogenicity that may be expected from the humanisation process has been examined by Hakimi et al., (1991) using the humanised form of the anti-Tac antibody, anti-Tac-H (Queen et al., 1989). The humanised antibody was expressed in the murine myeloma line Sp2/0. The antibody contained less than 10 endotoxin units/mg of protein. Antibody was administered to 8 groups each of 4 cynomolgus monkeys. The groups were given either anti-Tac-H or the murine antibody (anti-Tac-M) i.v. in doses of 0, 0.05, 0.5 or 5 mg/kg each day for 14 days followed by challenge with the same antibody on day 42. Pharmacokinetics and immunogenicity were monitored throughout the study. Adverse responses (anaphylaxis) to the anti-Tac-H on the 42 d re-challenge was seen in one animal given 5 mg/kg and in all 4 animals given 0.05 mg/kg of anti-Tac-M. Therefore none of the animals given 0.5 or 5 mgikg of anti-Tac-M received the day 42 re-challenge.

The response to the humanized antibody was seen to be lower in absolute amount and delayed in onset compared to the response to the murine antibody. In the anti-Tac-M groups response in 9 of 12 animals was seen during the course of treatment, while in those animals given the humanized antibody response was generally seen 5 to 10 days after the last injection. For both antibodies the level of response appeared in general to be inversely proportional to the dosage. The earliest and most vigorous response to the murine antibody was seen in the 0.05 mg/kg group where in the case of one animal an anti-antibody response measured at over 200 mg/mL was seen. In contrast the groups receiving the higher doses of the murine antibody had similar, lower patterns of absolute levels of anti-anti-Tac-M, with the 5 mg/kg group showing a delayed onset of response. In two animals no response was seen at this dose, while in the 0.5 mg/kg group one animal showed no response. For the animals given the humanized antibody a similar trend was seen but the levels of response were much lower. The highest response was seen in one animal given 0.5 mg/kg. where 60 mg/mL of anti-antibody was seen at day 42. This level of response was exceeded by 9 of the 12 animals given the murine antibody. Again the response was inversely proportional to the dosage with all of the animals in the 0.05 mg/kg group showing some level of response (in the range 5 to 25 mg/mL of anti-antibody). In all cases where a second dose at 42 days was able to be given a large, >10 fold, increase in specific titre was observed.

The type of response was measured by competition ELISA in which each of the murine or humanized antibodies was bound to a solid phase and incubated with serum in the presence of various potential competitors, including the antibodies themselves, soluble IL-2R or non-specific murine or human IgG. It was shown that the response to both murine and humanized antibody was both anti-idiotypic and anti-isotypic. However the anti-isotype response against the humanized antibody was marginal. The majority of the response against the humanized antibody could be inhibited by the presence of humanized or murine anti-Tac or soluble IL-2R suggesting that the response was predominantly anti-binding site.

Three studies of the use of the humanized anti-CAMPATH-1 antibody, CAMPATH-1H, have been described (Crowe, 1992: Hale et al., 1989; Mathieson et al., 1990). In the first study two patients with non-Hodgkin lymphoma were treated with CAMPATH-1H for up to 43 days with escalating doses ranging from 1–20 mg/day by intravenous infusion (Hale et al., 1988). No anti-antibody response was detected during the course of treatment. The lack of response may be due to the fact that the antibody itself is immunosuppressive and the patients were already immunosuppressed as a result of their disease (Hale et al., 1988).

A further case study has been reported (Mathieson et al., 1990). The CAMPATH-1 H antibody has been used in conjunction with a rat anti-human CD4 to establish a remission in a patient with a chronic and previously intractable systemic vasculitis. The lymphocyte population was depleted by a 3 day treatment of CAMPATH-1 H (i.v. 2 mg/day) followed by the rat anti-human CD4 for 12 days at 20mg/day (i.v.) to remove any remaining $T_H$ cells. After the treatment course remission of disease occurred that has lasted 12 months. No anti-antibody response has been detected.

More recently it has been disclosed that a further 8 patients with rheumatoid arthritis have been treated with CAMPATH-1 H. The patients were given 4mg/day for 5 days followed by 8 mg/day for a further 5 days. In 7 of 8 cases there was statistically significant reduction in assessable criteria for pain and joint disease (Crowe, 1992). No anti-antibody response was evident for a period of several months post treatment.

Hird et al., (1991) have administered the humanised anti-PLAP antibody Hu2PLAP (Verhoeyen et al., 1991), derived from the murine antibody H17E2 (Travers and Bodmer, 1984) in 7 patients with various carcinomas, including ovarian, stomach and breast. Two patients had raised serum levels of human anti-mouse antibody prior to therapy. In one case the patient had previously been treated with the murine antibody HMFG1, $^{90}$Y labelled by conjugation with the macrocycle DTPA. The second patient had had prior treatment with murine H17E2, $^{111}$In labelled by conjugation with the macrocycle, DOTA (Moi et al., 1988). The 7 patients received 220–833 mg of Hu2PLAP-$^{111}$In-DOTA i.v., as a radio-imaging dose. The patients were monitored at 24 and 96 h. In those patients with no pre-existing HAMA response the $t_{1/2}b$ was 73.1 h compared to 27 h for patients given the murine antibody. Where pre-existing HAMA response was seen the patients showed $t_{1/2}b$ of 47 h and 39 h. None of the 7 patients, however developed antibodies specific for the Hu2PLAP over the 96h of study, although 3 patients developed anti-DOTA antibodies, one of these being the patient previously treated with murine H17E2-$^{111}$In-DOTA and who had a pre-existing anti-DOTA response.

SUMMARY OF THE INVENTION

It can therefore be anticipated that the humanisation of A33 may lead to reduced immunogenicity in man, and overcome the problem of the HAMA response previously associated with the use of the murine antibody in humans.

We have now prepared humanised antibody molecules having specificity for the epitope recognised by the murine monoclonal antibody A33. The compounds in general show good tumour localisation and high tumour loading in vivo. Certain compounds have surprisingly increased avidity for target cells and are quickly eliminated from other body tissues, in particular from the kidney, leading to improved tumour to blood ratios and little or no undesirable side-effects.

Thus according to the first aspect of the present invention there is provided a humanised antibody molecule (HAM) having specificity for the epitope recognised by the murine monoclonal antibody A33 and having an antigen binding site wherein at least one of the complementarity determining regions (CDRs) of the variable domain is derived from the mouse monoclonal antibody A33 (MAb A33) and the remaining immunoglobulin-derived parts of the HAM are derived from a human immunoglobulin or an analogue thereof, said HAM being optionally conjugated to an effector or reporter molecule.

DETAILED DESCRIPTION OF THE INVENTION

The HAM of the invention may comprise a chimeric humanised antibody or a CDR-grafted humanised antibody. When the HAM comprises a CDR-grafted humanised antibody, each heavy or light chain variable domain may comprise only one or two A33-derived CDRs. Preferably, however, all three heavy and light chain CDRs are derived from A33. In general, the HAM according to the invention will have at least a binding potency equivalent to, or better than, the murine A33 antibody.

As described above, MAb A33 is an IgG2a/k monoclonal antibody previously described by Welt et al (1990). The amino acid sequences of the light and heavy chain variable regions of the antibody are shown in FIG. 3 (SEQ ID NOS 31–34 and 36–37, respectively hereinafter).

The HAM of the present invention may comprise: a complete antibody molecule, having full length heavy and light chains; a fragment thereof, such as a Fab, Fab', (Fab')$_2$ or Fv fragment; a single chain antibody fragment, e.g. a single chain Fv; a light chain or heavy chain monomer or dimer; multivalent monospecific antigen binding proteins comprising two, three, four or more antibodies or fragments thereof bound to each other by a connecting structure; or a fragment or analogue of any of these or any other molecule with the same specificity as MAb A33.

The remaining non-A33 immunoglobulin-derived parts of the HAM may be derived from a suitable human immunoglobulin. For instance, when the HAM is a CDR-grafted HAM, appropriate variable region framework sequences may be used having regard to the class or type of the A33 donor antibody from which the antigen binding regions are derived. Preferably, the type of human framework used is of the same or similar class or type as the donor antibody (A33 is IgG2-kappa). Advantageously, the framework is chosen to maximise or optimise homology with the donor antibody sequence, particularly at positions spatially close to or adjacent the CDRs. Examples of human frameworks which may be used to construct CDR-grafted HAMs are LAY, POM, TUR, TEI, KOL, NEWM, REI and EU. (Kabat et al, 1987) KOL and NEWM are suitable for heavy chain construction. REI is suitable for light chain construction and EU is suitable for both heavy chain and light chain construction. Preferably, however, the LAY framework is used as the human framework for both heavy and light chain variable domains in view of its high level of homology with MAb A33.

The light or heavy chain variable regions of the HAM may be fused to human light or heavy chain constant domains as appropriate, (the term "heavy chain constant domains" as used herein are to be understood to include hinge regions unless specified otherwise). The human constant domains of the HAM, where present, may be selected having regard to the proposed function of the antibody, in particular the effector functions which may be required. For example, the heavy chain constant domains fused to the heavy chain variable region may be human IgA, IgG or IgM domains. Preferably human IgG domains are used. IgG1 and IgG3 isotype domains may be used when the HAM is intended for therapeutic purposes and antibody effector functions are required. Alternatively, IgG2 and IgG4 isotype domains may be used when the HAM is intended for purposes for which antibody effector functions are not required, e.g. for imaging, diagnostic or cytotoxic targeting purposes. Light chain human constant domains which may be fused to the light chain variable region include human Lambda or, especially, human Kappa chains.

Analogues of human constant domains may alternatively be advantageously used. These include those constant domains containing one or more additional amino acids than the corresponding human domain, or those constant domains wherein one or more existing amino acids of the corresponding human domain has been deleted or altered. Such domains may be obtained, for example, by oligonucleotide directed mutagenesis.

The remainder of the HAM need not comprise only protein sequences from human immunoglobulins. For instance, a gene may be constructed in which a DNA sequence encoding part of a human immunoglobulin chain is fused to a DNA sequence encoding the amino acid sequences of a polypeptide effector or reporter molecule.

According to a second aspect of the present invention, there is provided a process for producing the HAM of the first aspect of the invention, which process comprises:

(a) producing in an expression vector an operon having a DNA sequence which encodes an antibody heavy or light chain comprising a variable domain wherein at least one of the CDRs of the variable domain is derived from the A33 MAb and the remaining immunoglobulin-derived parts of the antibody chain are derived from a human immunoglobulin;

(b) producing in an expression vector an operon having a DNA sequence which encodes a complementary antibody light or heavy chain comprising a variable domain wherein at least one of the CDRs of the variable domain is derived from the MAb A33 and the remaining immunoglobulin-derived parts of the antibody chain are derived from a human immunoglobulin;

(c) transfecting a host cell with both operons; and (d) culturing the transfected cell line to produce the HAM.

The cell line may be transfected with two vectors, the first vector containing the operon encoding the light chain-derived polypeptide and the second vector containing the operon encoding the heavy chain- derived polypeptide. Preferably, the vectors are identical except in so far as the coding sequences and selectable markers are concerned so as to ensure as far as possible that each polypeptide chain is equally expressed.

Alternatively, a single vector may be used, the vector including the operons encoding both light chain- and heavy chain-derived polypeptides.

In further aspects, the invention also includes DNA sequences coding for the heavy and light chains of the HAM of the present invention, cloning and expression vectors containing these DNA sequences, host cells transformed with these DNA sequences and processes for producing the heavy or light chains and antibody molecules comprising expressing these DNA sequences in a transformed host cell.

The general methods by which the vectors may be constructed, transfection methods and culture methods are well known per se [see for example Maniatis et al (1982) and Primrose and Old (1980) and the Examples hereinafter].

The DNA sequences which encode the A33 heavy and light chain variable domain amino acid sequences (and the corresponding deduced amino acid sequences) are given hereinafter in FIG. 3 (SEQ ID NOS 30–37, respectively).

DNA coding for human immunoglobulin sequences may be obtained in any appropriate way. For example, amino acid sequences of preferred human acceptor frameworks, such as LAY, POM, KOL. REI, EU, TUR. TEI and NEWM, are widely available to workers in the art. Corresponding DNA sequences which code for these amino acid sequences may be inferred or deduced by reverse application of the genetic code. Similarly, the amino acid sequences of human constant region domains are well known and DNA sequences which code for them may be readily deduced.

The standard techniques of molecular biology may be used to prepare DNA sequences coding for CDR-grafted products. Desired DNA sequences may be synthesised completely or in part using oligonucleotide synthesis techniques. Site-directed mutagenesis and polymerase chain reaction (PCR) techniques may be used as appropriate. For example, oligonucleotide directed synthesis (Jones et al, 1986) may be used. Also, oligonucleotide directed mutagenesis of a pre-existing variable domain region (Verhoeyen a, 1988; Riechmann et al, 1988) may be used. Enzymatic filling-in of gapped oligonucleotides using T4 DNA polymerase (Queen et al, 1989; International Patent Specification No. WO 90/078861) may be used.

Any suitable host cell/vector system may be used for expression of the DNA sequences coding for the chimeric or CDR-grafted heavy and light chains. Bacterial, e.g. *E. coli*, and other microbial systems may be used, advantageously in particular for expression of antibody fragments. e.g. Fv, Fab and Fab' fragments and single chain antibody fragments, e.g. single chain Fvs. A particularly useful process for producing Fab fragments according to the invention using *E. coli* transformed with an expression vector derived from pACtac (International Patent Specification No. WO 92/01059) is described in the Examples hereinafter and forms a further aspect of the invention. Eucaryotic, e.g. mammalian host cell, expression systems may also be used to obtain antibodies according to the invention, particularly for production of larger chimeric or CDR-grafted antibody products, including complete antibody molecules. Suitable mammalian host cells include CHO cells and myeloma or hybridoma cell lines, for example NS0 cells.

In the HAM according to the invention, the heavy and light chain variable domains may comprise either the entire variable domains of MAb A33, or may comprise framework regions of a human variable domain having grafted thereon one, some or all of the CDRs of MAb A33. Thus the HAM may comprise a chimeric humanised antibody or a CDR-grafted humanised antibody.

When the HAM is a CDR-grafted humanised antibody, in addition to the CDRS, specific variable region framework residues may be altered to correspond to non-human, i.e. the A33 mouse, residues. Preferably, the CDR-grafted humanised antibodies of the present invention include CDR-grafted humanised antibodies as defined in our International Patent Specification No. WO-A-91109967. The disclosure of WO-A-91/09967 is incorporated herein by reference.

Preferably, the CDRs of the light chain correspond to the Kabat MAb A33 CDRs at CDR1 (residues 24 to 34) and CDR2 (residues 50 to 56) and to the structural loop residues (residues 91 to 96) or Kabat MAb A33 CDR residues (residues 89 to 97) in CDR3. (The residue designations given above and elsewhere in the present application are numbered according to the Kabat numbering system Kabat et al, 1987). In addition, the light chain may have mouse A33 residues at one or both of residues 46 and 87. In a preferred embodiment, when the human framework used is LAY, the light chain comprises Kabat MAb A33 CDRs at all of CDR1, CDR2 and CDR3 and preferably additional A33 residues at positions 46 and 87.

Preferably, the CDRs of the heavy chain correspond to the Kabat MAb A33 CDRs at all of CDR1 (31 to 35), CDR2 (50 to 65) and CDR3 (95 to 102). In addition, the heavy chain may have mouse A33 residues at one or more of residues, 1, 27, 28, 29, 30, 72, 73, 82b, 86 and 94.

Preferably, the humanized antibody molecule (HAM) of the present invention is a HAM having specificity for the epitope recognized by the marine monoclonal antibody A33 (MAb A33), wherein the HAM comprises: (1) the light chain variable region comprising amino acids 28 to 135 of SEQ ID NO, 46, (2) the heavy chain variable region comprising amino acids 27 to 143 of SEQ ID NO: 55; and (3) the remaining immununoglobulin-derived parts of the IIAM being derived from a human immunoglobulin or an analogue thereof, wherein the HAM is optionally conjugated to an effector or reporter molecule.

The HAM according to the invention may be a complete antibody or, as explained above, a fragment thereof; a monomer or dimer; or, in particular, a multivalent monospecific binding protein. Certain compounds of this latter group are particularly advantageous in that they posess high avidity and can be used to achieve improved tumour to blood ratios. The compounds are quickly eliminated from other body tissues and overall have little or none of the undesirable side-effects which can occur when antibody products accumulate in non-tumourous tissue.

Thus according to a further particular aspect of the invention we provide a multivalent monospecific antigen binding protein comprising two, three, four or more antibodies or fragments thereof bound to each other by a connecting structure, which protein is not a natural immunoglobulin, each of said antibodies or fragments having a specificity for the epitope recognised by the murine monoclonal antibody A33 said antigen binding protein being optionally conjugated with an effector or reporter molecule.

In this aspect of the invention each antibody or fragment is preferably a humanised antibody or a fragment thereof, as defined above with respect to the humanised antibody molecule (HAM) of the first aspect of the invention, and the multivalent monospecific antigen binding protein is thus a humanised multivalent monospecific antigen binding protein. Non-humanised, e.g. murine, multivalent monospecific antigen binding proteins can however be contemplated and the invention is to be understood to also extend to these.

The multivalent antigen binding protein preferably comprises two, three or four antibodies or, preferably, fragments thereof bound to each other by a connecting structure.

Antibody fragments for use in this aspect of the invention may De those discussed above in relation to the HAMs of the invention. Particularly useful fragments are Fab fragments.

Thus according to a preferred aspect of the invention we provide a multivalent monospecific antigen binding protein comprising two, three or four Fab fragments bound to each other by a connecting structure, which protein is not a natural immunoglobulin, each of said Fab fragments having specificity for the epitope recognised by the murine monoclonal antibody A33, said antigen binding protein being optionally conjugated with an effector or reporter molecule.

Compounds of this type provide exceptionally good tumour to blood ratios when used in vivo. Particularly advantageous compounds are those comprising four, or especially three, Fab-fragments bound to each other by a connecting structure, which in addition to providing good tumour to blood ratios in vivo are quickly eliminated from other tissues such as the kidney, and do not have undesirable side-effects which would be associated with accumulation of the fragments in such tissues.

The term "Fab" is used herein to mean optionally modified Fab and Fab' antibody fragments derived from natural antibodies or synthesised, either chemically or by recombinant DNA technology. By "optionally modified" is meant that the Fab or Fab' fragment may contain a number of insertions, deletions or changes in or to the amino acid sequence as long as the binding ability of the fragment is not adversely affected.

Each Fab fragment is preferably a humanised fragment. A particularly advantageous Fab fragment is a genetically modified Fab fragment which has only a single free thiol group in the hinge region. Construction of such fragments is described in our European Patent Specification No. 347433 and in the Examples hereinafter.

In the multivalent antigen binding proteins of the invention, the antibodies or fragments thereof are preferably bound together covalently by the use of cross-linkers. In general the cross-linker may be any of the many known chemical cross-linkers conventionally used for cross-linking molecules such as proteins. Preferably however, the cross-linker is a specifically designed single linker molecule containing two, three, four or more functional groups each capable of reacting with an appropriate amino acid in the antibody or fragment, such as an amino acid containing a side-chain thiol, amino or carboxyl group, or with the carboxyl group at the C-terminus.

Examples, of such linkers can be found in International Patent Specifications Nos. WO-A-90/09195 and WO-A-90/09196 and European Patent Specifications Nos. 384624, 385601, 446071 and 453082. Particulary useful tri- and tetra-functional cross-linking reagents are described in our copending International Patent Application No. WO 92/22583, the disclosure of which is incorporated herein by reference.

Thus, for example, a particularly useful group of suitable cross-linking agents include those of formula (1);

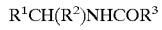

wherein $R^1$ is a carboxyl (—$CO_2H$) or esterified carboyl (—$CO^2R$) group a carboxamide (—$CONH_2$) or a group —COA where A is an effector or reporter molecule attached to the —CO group either directly or via a spacer group to form a carbon—carbon, or carbon-hetero atom linkage; $R^2$ and $R^3$, which may be the same or different, is each an optionally substituted straight or branched alkylene, alkenylene or alkynylene chain [optionally interrupted by one or more —O— or —S— atoms, or —$N(R^4)$ (where $R^4$ is a hydrogen atom or a $C_{1-6}$ alkyl group), —$N(R^4)CO$—, —$CON(R^4)$—, $C_{5-8}$ cycloalkylene, $C_{6-12}$ arylene or $C_{5-10}$ heteroarylene groups] containing one, two, three or more reactive functional groups such that the total number of reactive functional groups in $R^2$ and $R^3$ together is two, three or more.

It will be appreciated that in cross-linking reagents of this type, the reactive functional groups react with appropriate amino acids in the antibody or fragment such that the resulting connecting structure Is a residue of the cross-linking reagent.

In a further preference the antibodies or fragments thereof in the multivalent antigen binding proteins of the invention are bound to each other by a connecting structure linked to a thiol group in each antibody or fragment.

In general, the cross-linking reaction to produce the multivalent binding proteins of the invention may be achieved using conventional processes, for example by mixing the starting materials, comprising the antibody or fragment and the appropriate linker in an aqueous solvent, at an appropriate temperature e.g. ambient temperature to 40° C., e.g. around 37° C. The relative concentrations of the starting materials used will depend to a large extent on the cross-linker used, and the number of reactive functional groups it contains, and the nature of the desired product, but generally the antibody or fragment will be present in excess concentration.

If desired, the antibody or fragment starting material may be modified before use to facilitate the reaction with the cross-linker. Thus, for example, thiol groups may be introduced for subsequent reaction with the cross-linker, using conventional thiolation reactions, for example by reaction with 2-iminothiolane, as described in the Examples hereinafter. In another example, where the antibody fragment has a blocked thiol group, for example a blocked hinge thiol group, the free thiol group may be obtained by any suitable reaction, such as by reduction, e.g. by using β-mercaptoethylamine as described in the Examples hereinafter.

The humanised antibody molecules according to the invention, including the multivalent antigen binding proteins may be used for in vivo diagnosis or therapy, in particular for the diagnosis or treatment of colorectal tumours and metastases arising therefrom.

For use in diagnosis or therapy, the HAM according to the invention is preferably conjugated to an effector or reporter molecule. Thus for example the HAM of the pesent invention may have attached to it an effector molecule such as a cytotoxic or cytostatic agent, or a reporter group, for example an atom or molecule such as a radionuclide for example radioiodide or complexed radionuclide capable of being detected while inside the human body.

The effector or reporter molecule may be attached direct to the HAM of the invention, optionally through a linking group, or where the HAM contains a connecting structure through the connecting structure itself.

For instance, the HAM may have an organic group, such as a macrocycle, capable of binding a metal atom, or a toxin, such as ricin, or an anti-tumour agent attached to it by a covalent bridging structure. Alternatively, the procedures of recombinant DNA technology may be used to produce a HAM in which the Fc fragment, CH2 or CH3 domain of a complete molecule has been replaced by or has attached thereto by peptide linkage a functional non-immunoglobulin protein, such as an enzyme or toxin molecule.

Particularly useful reporter or effector groups are those described in our copending International Patent Specification No. WO 92/22583, the disclosure of which is incorporated herein by reference.

Thus, for example, particular effector or reporter groups include radionuclides, particularly radioiodide, chelated metals, flourescent compounds of compounds which may be detected by NMR or ESR spectroscopy.

Chelated metals include chelates of di-or tripositive metals having a coordination number from 2 to 8 inclusive. Particular examples of such metals include technetium (Tc), rhenium (Re), cobalt (Co), coper (Cu), gold (Au), silver (Ag), lead (Pb), bismuth (Bi), indium (In), gallium (Ga), yttrium (Y), terbium (Th), gadolinium (Gd), and scandium (Sc). In general the metal is preferably a radionuclide. Particular radionuclides include $^{99}mTc$, $^{186}Re$, $^{188}Re$, $^{58}Co$, $^{60}Co$, $^{67}Cu$, $^{195}Au$, $^{199}Au$, $^{110}Ag$, $^{203}Pb$, $^{206}Bi$, $^{207}Bi$, $^{111}In$, $^{67}Ga$, $^{68}Ga$, 88y, 90Y, $^{160}Tb$, $^{153}Gd$ and $^{47}Sc$.

The chelated metal may be for example one of the above types of metal chelated with any suitable polydentate chelating agent, for example cyclic polyamines, polyethers, (e.g. crown ethers and derivatives thereof); polyamides; porphyrins; and carbocyciic derivatives.

In general, the type of chelating agent will depend on the metal in use. One particularly useful group of chelating agents in conjugates according to the invention, however, are acyclic and cyclic polyamines, especially polyaminocarboxylic acids, for example diethylenetriaminepentaacetic acid and derivatives thereof, and macrocyclic amines, e.g. cyclic t ri-aza and tetra-aza derivatives for example 1,4,7-triazacyclononane-N,N'N"-trisacetic acid and 1,4,7,10 tetraazacyclododecane-N,N',N",N'"-tetraacetic acid and derivatives thereof; and polyamides, especially desferrioxamine and derivatives thereof.

Particularly useful chelated metals are chelated $^{111}$In and $^{90}$y.

In multivalent antigen binding proteins according to the invention the reporter or effector group may constitute part of the linking group binding the antibodies or fragments together, for example as described in International Patent Specification No. WO 92122583 and in formula (1) above. In this respect particularly useful multivalent antigen binding proteins according to the invention are those wherein the antibodies or fragments thereof are bound to each other by a cross-linking agent selected from CT557, CT558 or CT998, and the metal, e.g. yttrium or indium complexes thereof. CT557, CT558 and CT998 are the compounds of formulae (2), (3) and (4) below, the preparation of which is described in International Patent Specification No. WO 92122583:

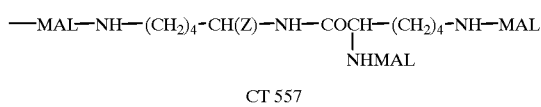

(2)

CT 557

Wherein MAL is

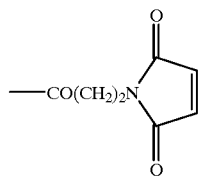

and Z is benzyloxycarbonyl;

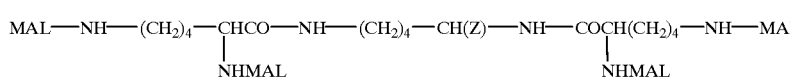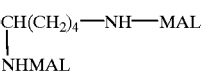

(3)

CT 558 where MAL and Z are as defined for formula (2); or

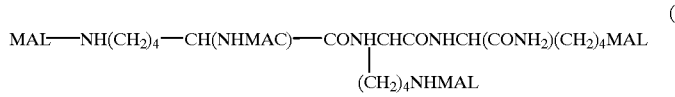

(4)

CT 998 where MAL is as defined for formula (2) and MAC is:

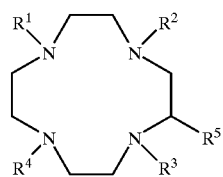

where $R^1$, $R^2$, $R^3$ and $R^4$ is each a group $-CH_2CO_2H$ and $-R^5$- is a group $-(CH2)_4NHCO(CH_2)_2CO-$. CT 998 may be prepared from the compound of Example 2 and Intermediate 8 described in WO 92122583.

Four, or, in particular, three Fab fragments bound together by CT 557, CT558 or CT998, and the metal, e.g. yttrium or indium complexes thereof are especially useful. In compounds of this type, the fragments are preferably bound to each other through a thiol group present in each fragment. Advantageously each fragment is a genetically engineered fragment containing one thiol group (for reaction with the cross-linker) in the hinge region.

The present invention also includes therapeutic and diagnostic compositions containing the HAM of the invention, particularly a conjugate molecule comprising a HAM conjugated to an effector or reporter molecule and uses of such compositions in therapy and diagnosis, in particular for the treatment or diagnosis of colorectal tumours and metastases arising therefrom. Such therapeutic and diagnostic compositions typically comprise a HAM according to the invention together with a pharmaceutically acceptable excipient, diluent or carrier, e.g. for in vivo use.

Therapeutic and diagnostic uses typically comprise administering a pharmaceutically effective amount of a HAM according to the invention to a human subject. The exact dose to be administered will vary according to the intended use of the HAM and on the age and condition of the patient but may be typically varied from about 0.1 mg to 1000 mg, for example from about 1 mg to 500 mg. The HAM may be administered as a single dose, or in a continuous manner over a period of time. Doses may be repeated as appropriate. The HAM may be formulated in accordance with conventional practice for administration by any suitable route, and may generally be in a liquid form [e.g. a solution of the HAM in a sterile physiologically acceptable buffer] for administration by for example an intravenous, intraperitoneal or intramuscular route.

DESCRIPTION OF SPECIFIC EMBODIMENTS

The present invention is now described by way of example only, by reference to be accompanying drawings, in which:

FIG. 1 shows oligonucleotide primers (SEQ ID NOS 5–29, respectively) for PCR cloning of murine A33 variable region sequences:

A. Chimeric light chain expression vector, pRO108

B. Chimeric heavy chain expression vector, pRO107

Only relevant restriction sites are shown;

FIG. 3 shows the amino acid sequences (SEQ ID NOS 31–34 and 36–37 respectively)of the variable regions of A33 light chain (A) and heavy chain (B). Sequences for the signal sequence (underlined) and the mature variable region (upper case) are shown. DNA sequence (SEQ ID NOS 30 and 35, respectively) defined by the PCR primers are shown italicised. The CDR regions are shown double underlined FIG. 4 shows the oligonucleotides (SEQ ID NOS 38 and 45, respectively)used for the assembly of the A33 humanised light chain-variable region nucleotides are shown underlined. The expected coding sequence for the signal sequence (italicised), the mature variable region (upper case) and the N terminal sequence of the human kappa constant region (lower case) (SEQ ID NOS 44) are shown below the oligonucleotide sequences. The mature light chain variable region comprises amino acids 28 to 135 of SEQ ID NO: 46 and corresponds to the upper case letters of FIG. 4.

The CDR regions and the non-CDR residues derived from the murine sequence are shown double underlined;

FIG. 5 shows the oligonucleotides (SEQ ID NOS 47 and 54, respectively) used for the assembly of the A33 humanised heavy chain-variable region nucelotides are shown underlined.

The expected coding sequence for the signal sequence (italicised), the mature variable region (upper case) and the N terminal sequence of the human CH1 domain region (lower case) (SEQ ID NOS 55) are shown below the oligonucleotide sequences. The mature heavy chain variable region comprising amino acids 27 to 143 of SEQ ID NO: 55 and corresponds to the upper case letters of FIG. 5.

Figure 7A:
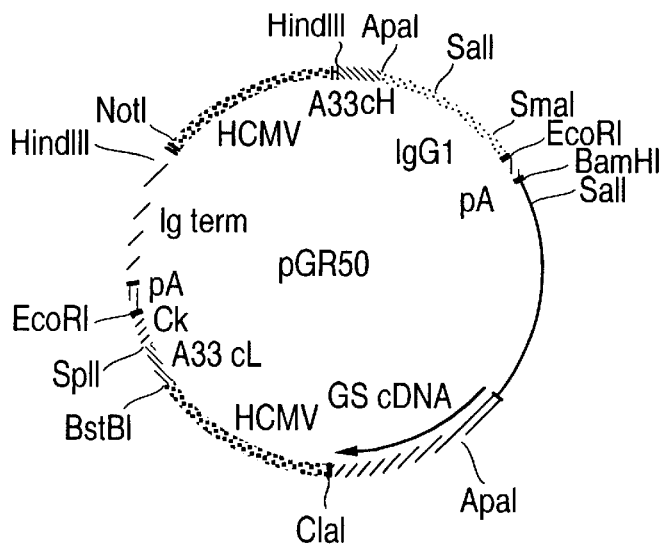
Figure 7B:
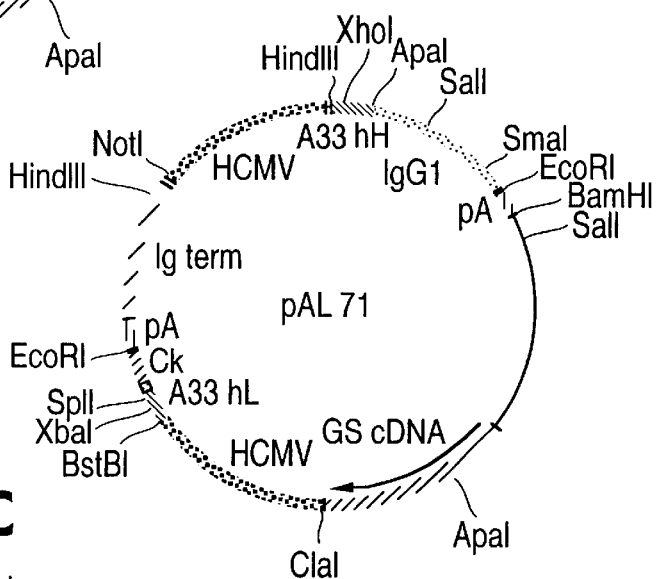
Figure 7C:
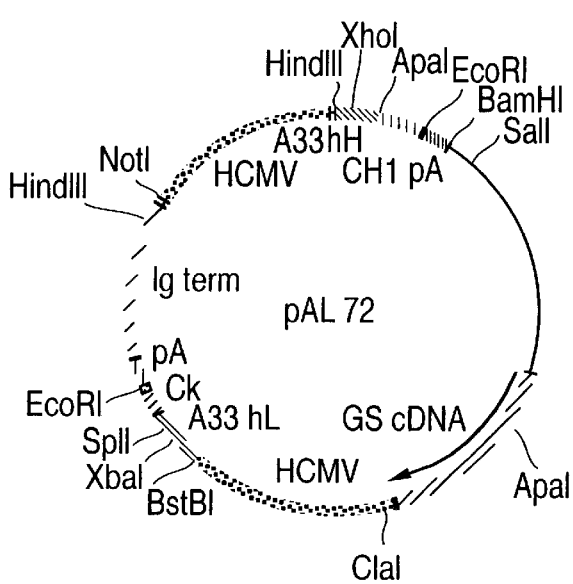

The CDR regions and the non-CDR residues derived from the murine sequence are shown double underlined;

FIG. 6 shows the results of a competition assay in which murine A33 (*) and humanised A33 prepared form CHO-KL transient expression experiments were used to compete for binding to Colo205 cells with FITC-labelled murine A33. Residual FITC-mA33 bound to cells was measured in a FACScan analyser and fluorescence (Y axis) was related to input unlabelled antibody (X axis);

FIG. 7 is a schematic of the chimeric and humanised A33 GS expression vectors

A. Chimeric A33(γ1) expression vector, pGR50

B. Humanised A33(γ1) expression vector, pAL71

C. Humanised A33 FAB'(γ4Δcys) expression vector, pAL72

Figure 17:
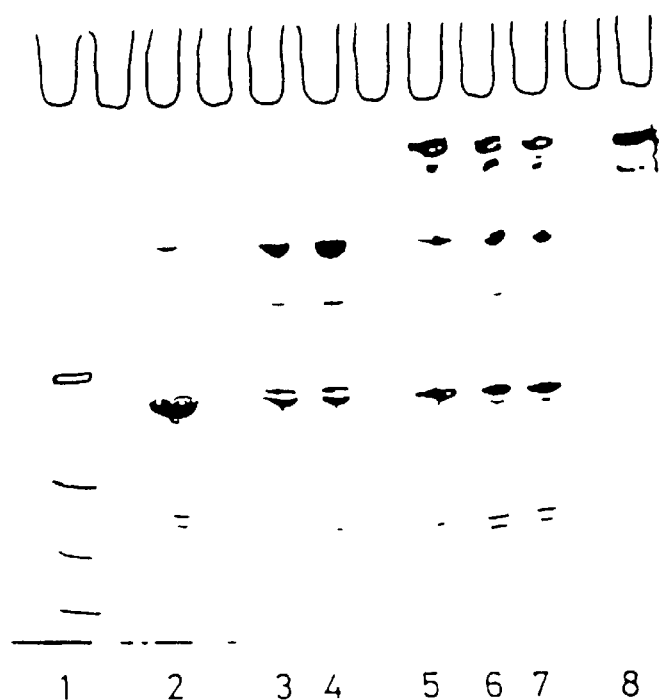

Only relevant restriction sites are shown;

FIG. 8 shows the biodistribution of $^{111}$cA33(γ1)-9N3 conjugate in LS174T tumour bearing nude mice at 24, 48, 120 and 192 h post-injection;

FIG. 9 shows the biodistribution of $^{90}$Y-hA33(γ1)-12N4 conjugate in Colo205 tumour bearing nude mice at 24, 48 and 144 h post-injection:

FIG. 10 is a Schatchard plot showing that hA33 (γ1) and murine A33 are equally potent in binding to cells of the human colorectal cancer cellline SW1222;

FIG. 11 compares the biodistribution of $^{90}$Y-hA33(γ1)-12N4, $^{90}$Y-cA33(γ1)-12N4 and $^{90}$Y-murine A33-12N4 conjugates in female nude mice bearing subcutaneous SW 1222 xenografts at 24, 72 and 120h post-injection;

FIG. 12 shows the biodistribution of $^{125}$I-hA33(γ1) in female nude mice bearing subcutaneous SW 1222 xenografts at 3, 24, 48 and 168h post-injection;

FIG. 13 is a graph showing the complete regression of SW 1222 tumours in female nude mice following treatment with $^{90}$Y-A33(γ1)-12N4 conjugate;

FIG. 14 shows a HPLC profile of hA33 Fab'(γ4Δcys) cross linking with CT 52 to form the DFM A. Reaction mixture B. Purified DFM FIG. 15 shows a HPLC profile of hA33 Fab'(γ4Δcys) cross linking using CT557 to form the TFM A. Reaction mixture B. Purified TFM FIG. 16 shows a HPLC profile of hA33 Fab'(γ4Δcys) cross linking using CT998 to form the TFM FIG. 17 shows a non reducing SDS-PAGE of hA33 cross-linked materials.

Lane 1, Molecular weight markers; Lane 2, hA33 Fab' (γ4Acys); Lane 3, A33 DFM reaction mixture; Lane 4, A33 DFM reaction mixture; Lane 5, A33 TFM (CT557) reaction mixture; Lane 6, A33 TFM (CT557) reaction mixture; Lane 7, A33 TFM (CT998) reaction mixture; Lane 8, Purified A33 TFM(CT557).

Figure 18:
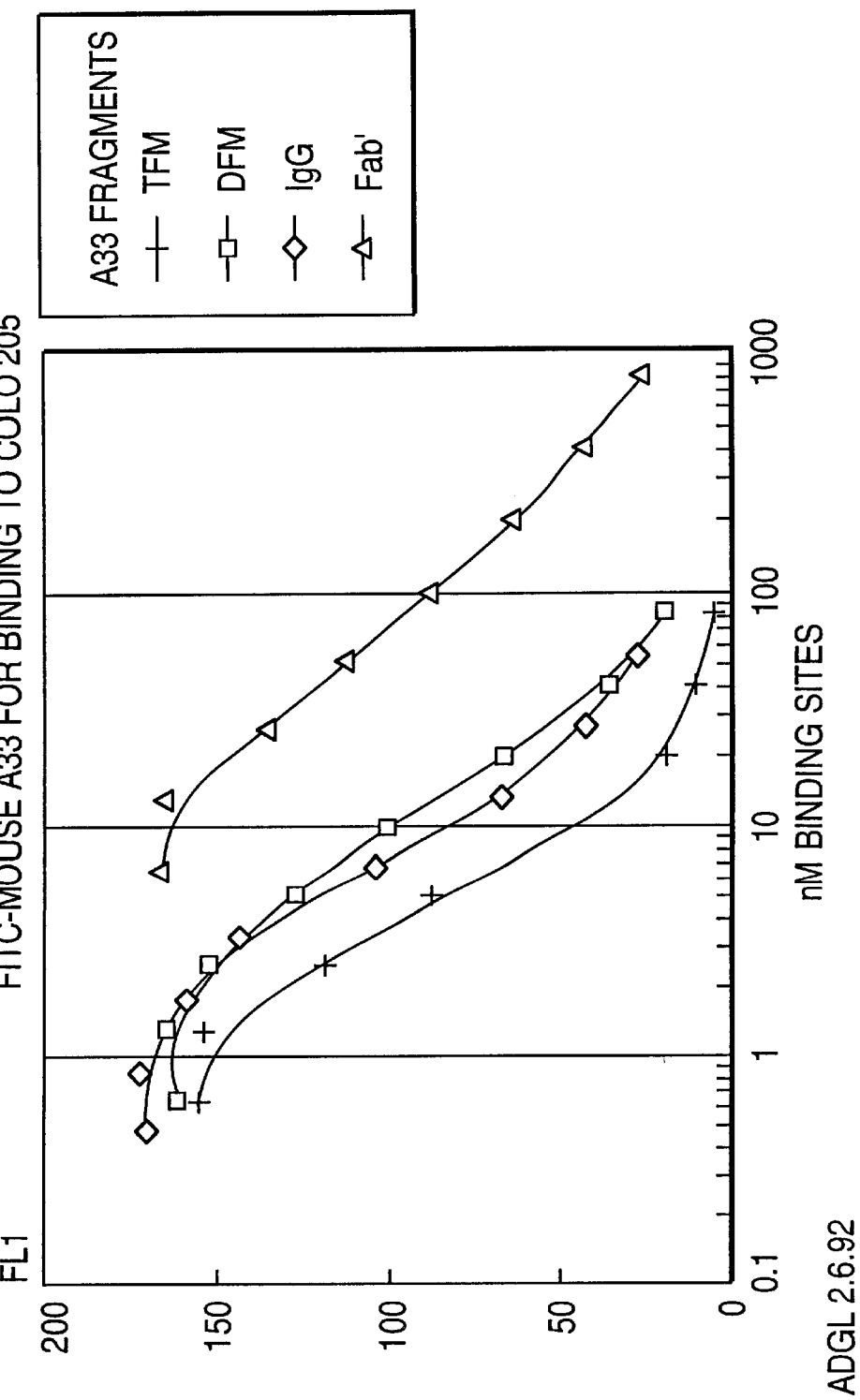
Figure 19:
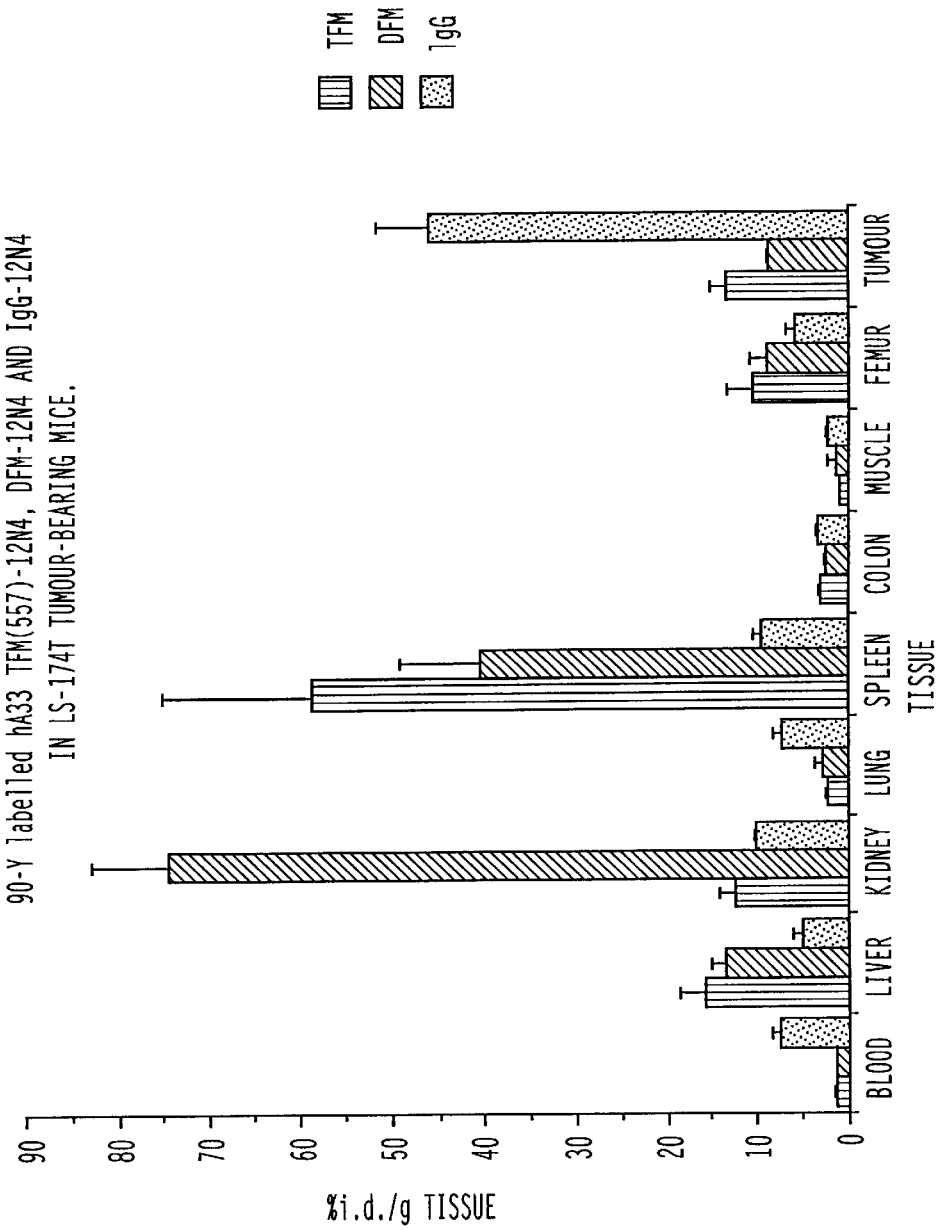
Figure 20:
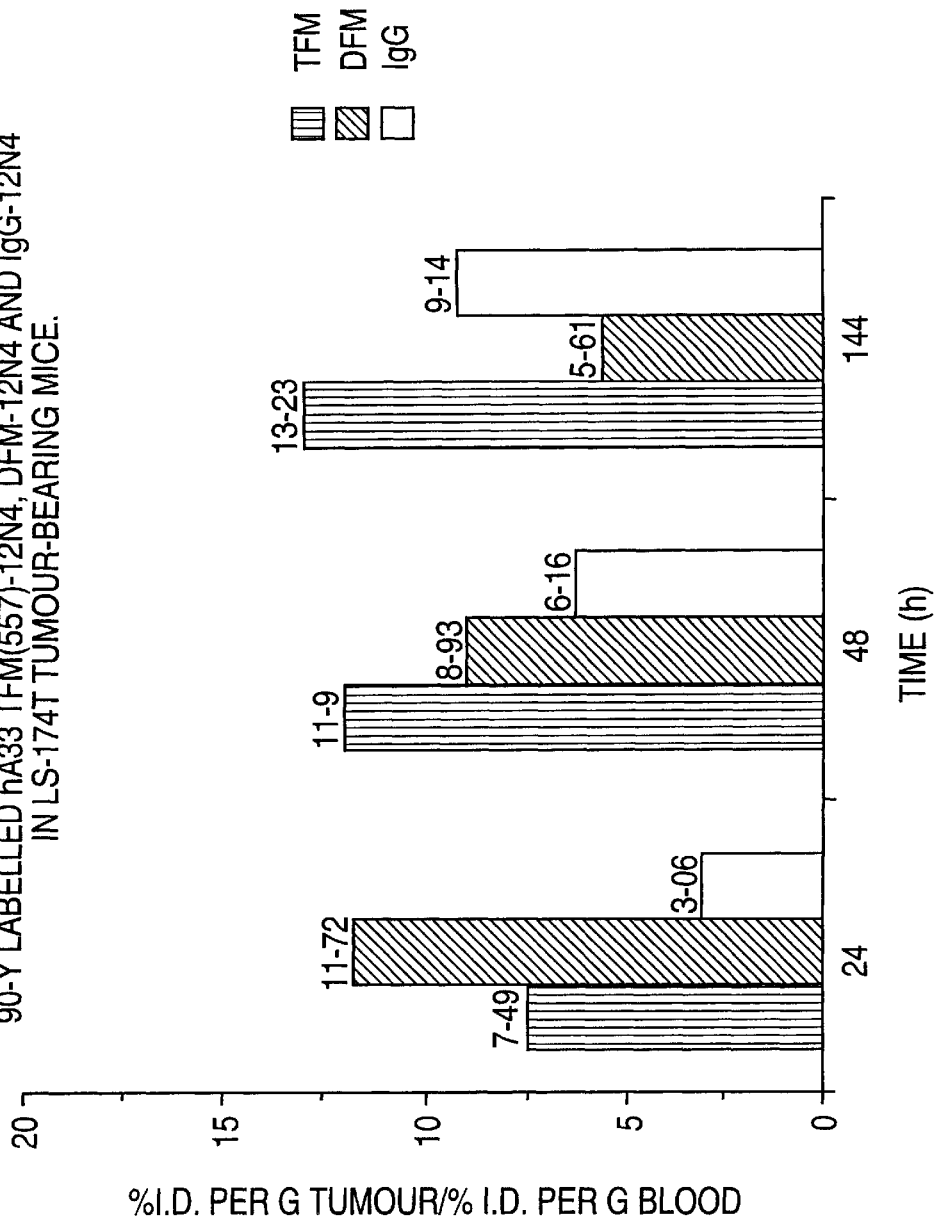
Figure 21:
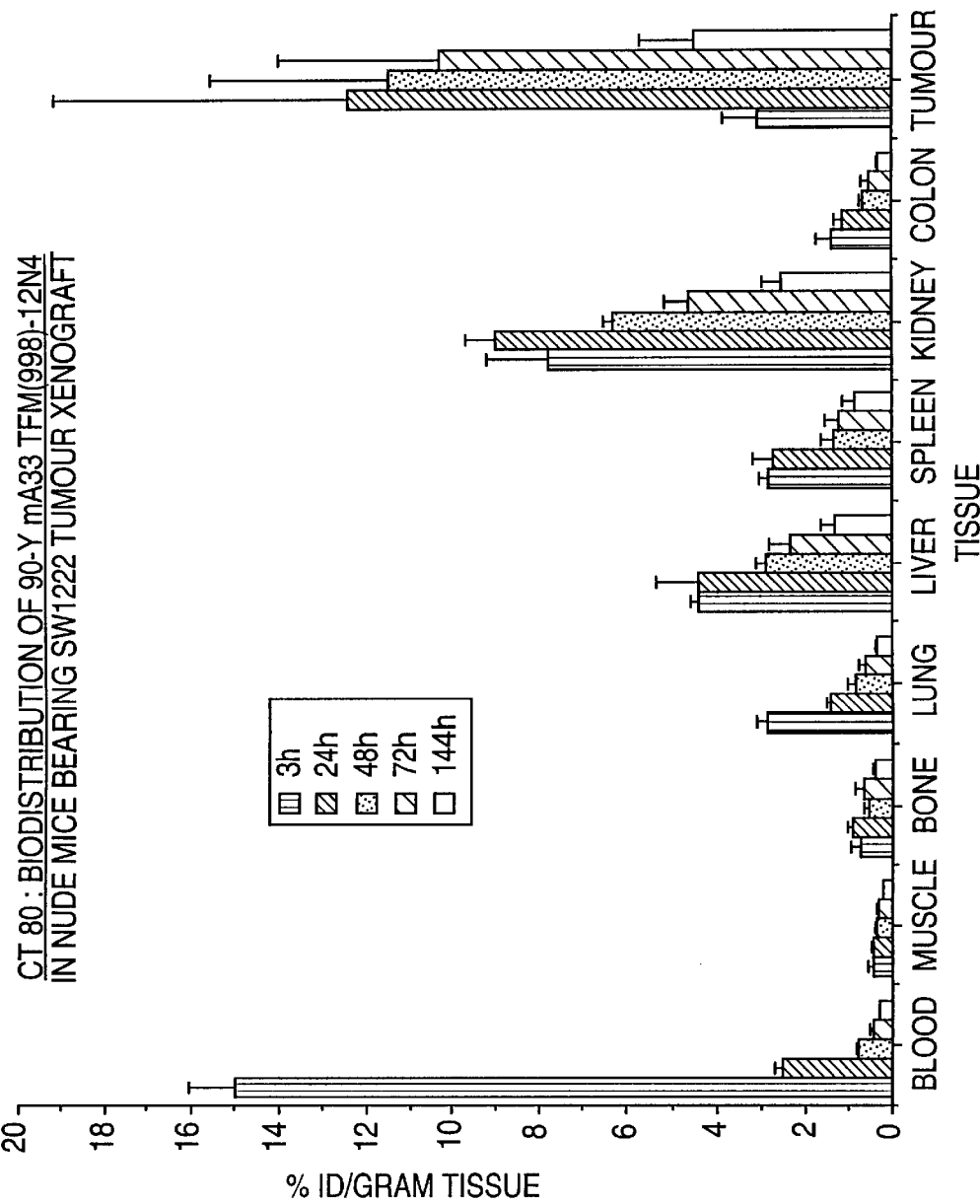
Figure 22:
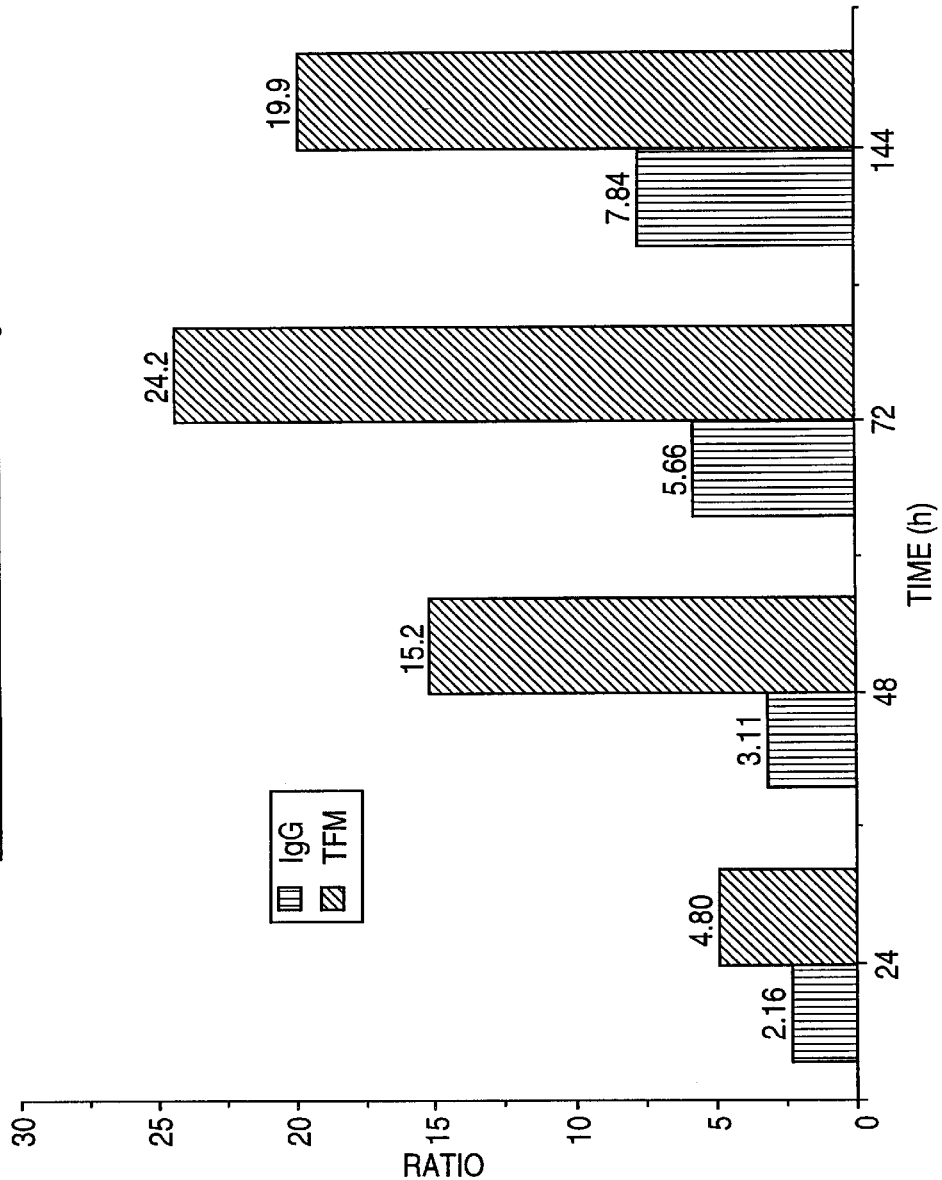
Figure 23:
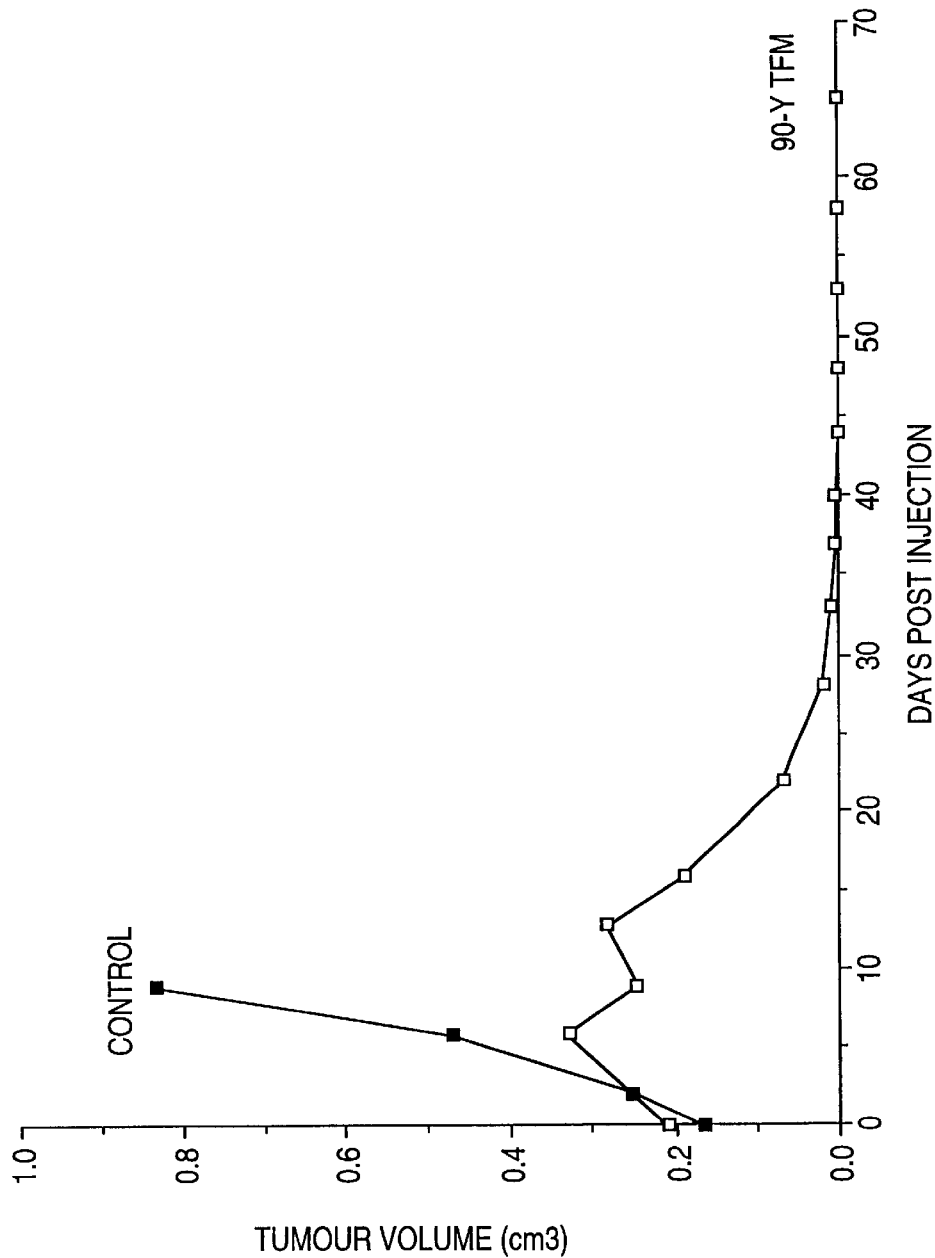
Figure 24:
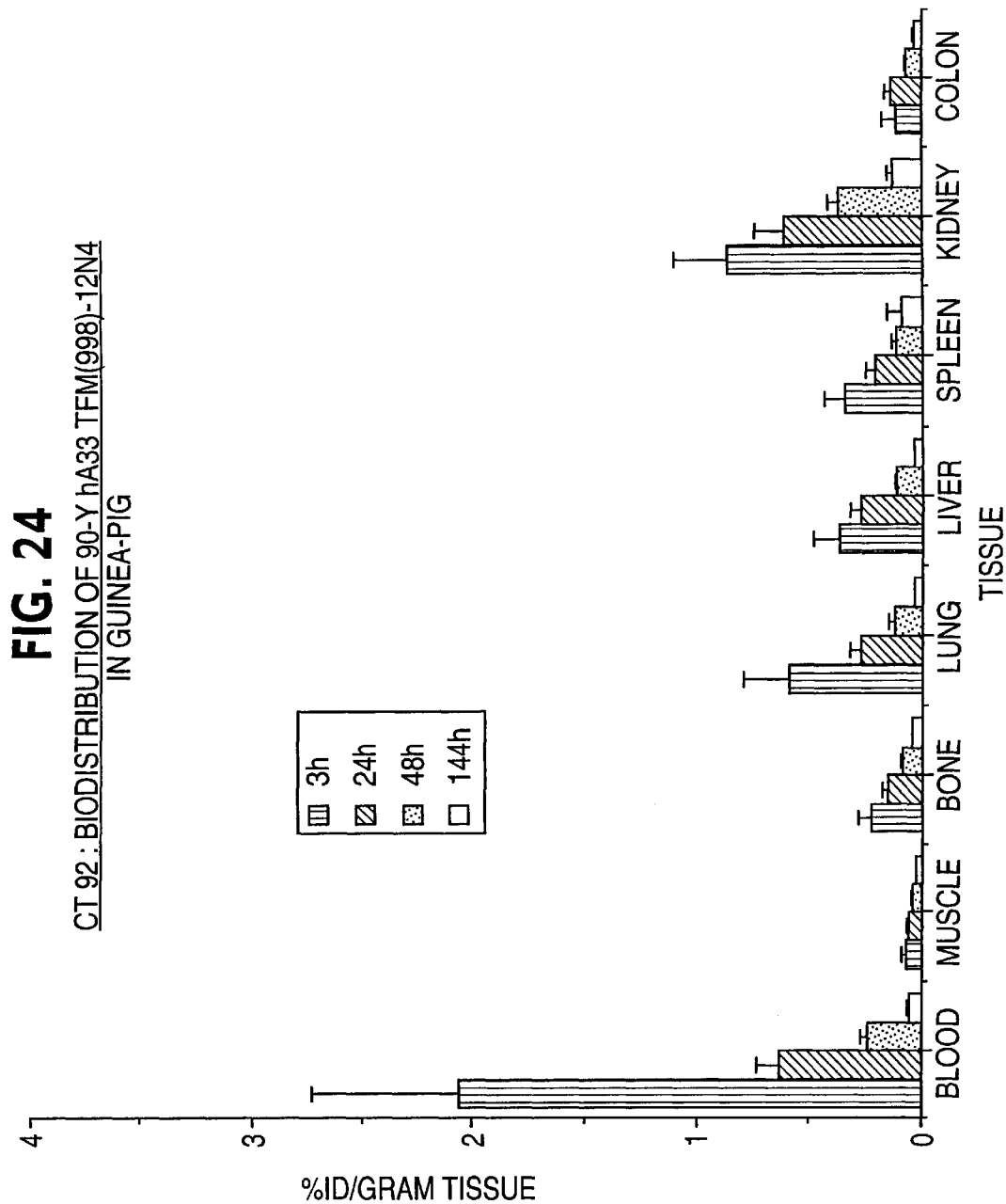
Figure 25:
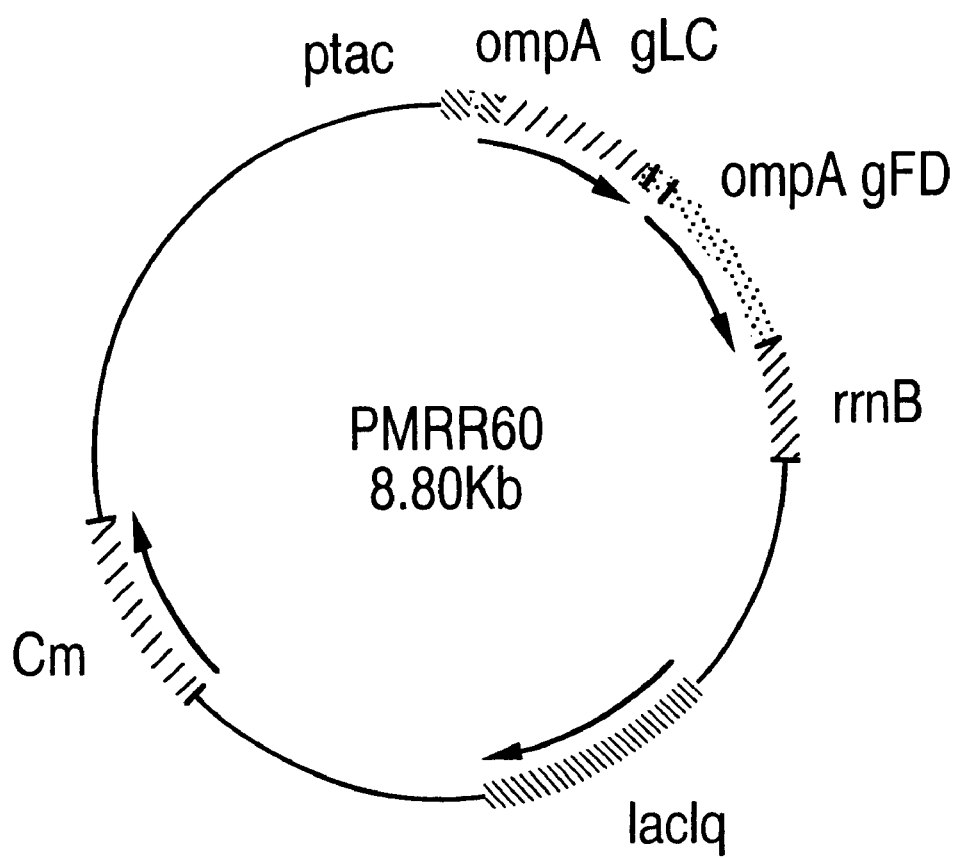
Figure 26:
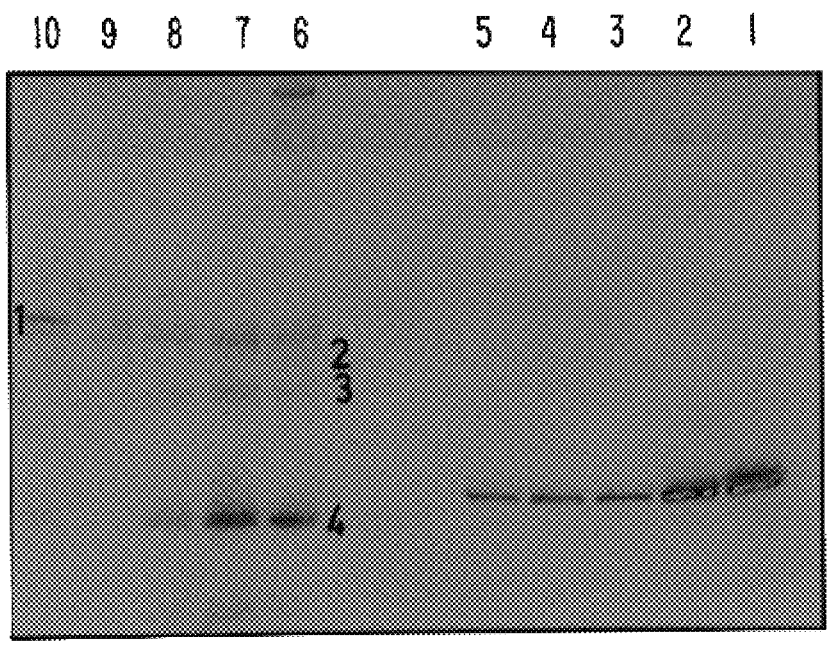
Figure 28:
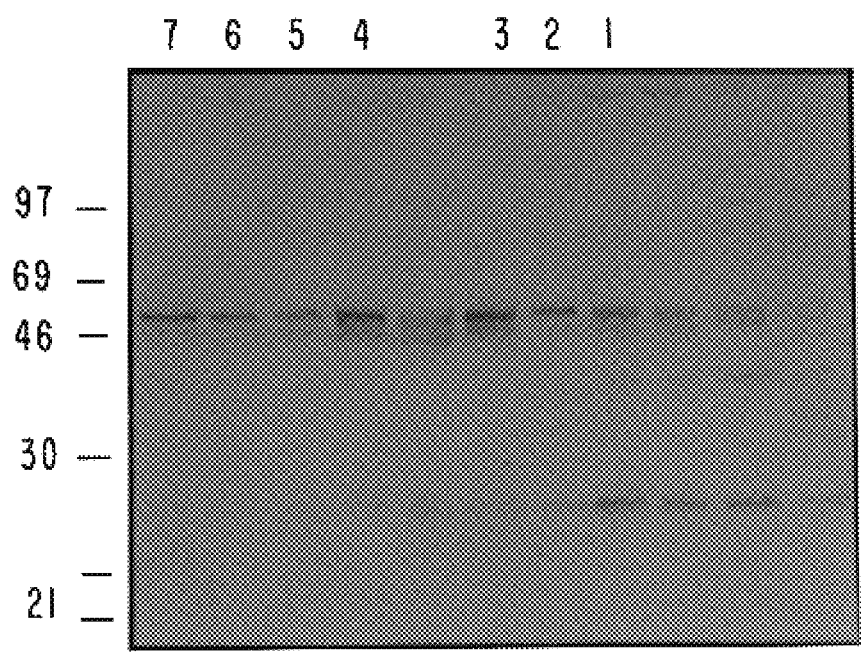
Figure 29:
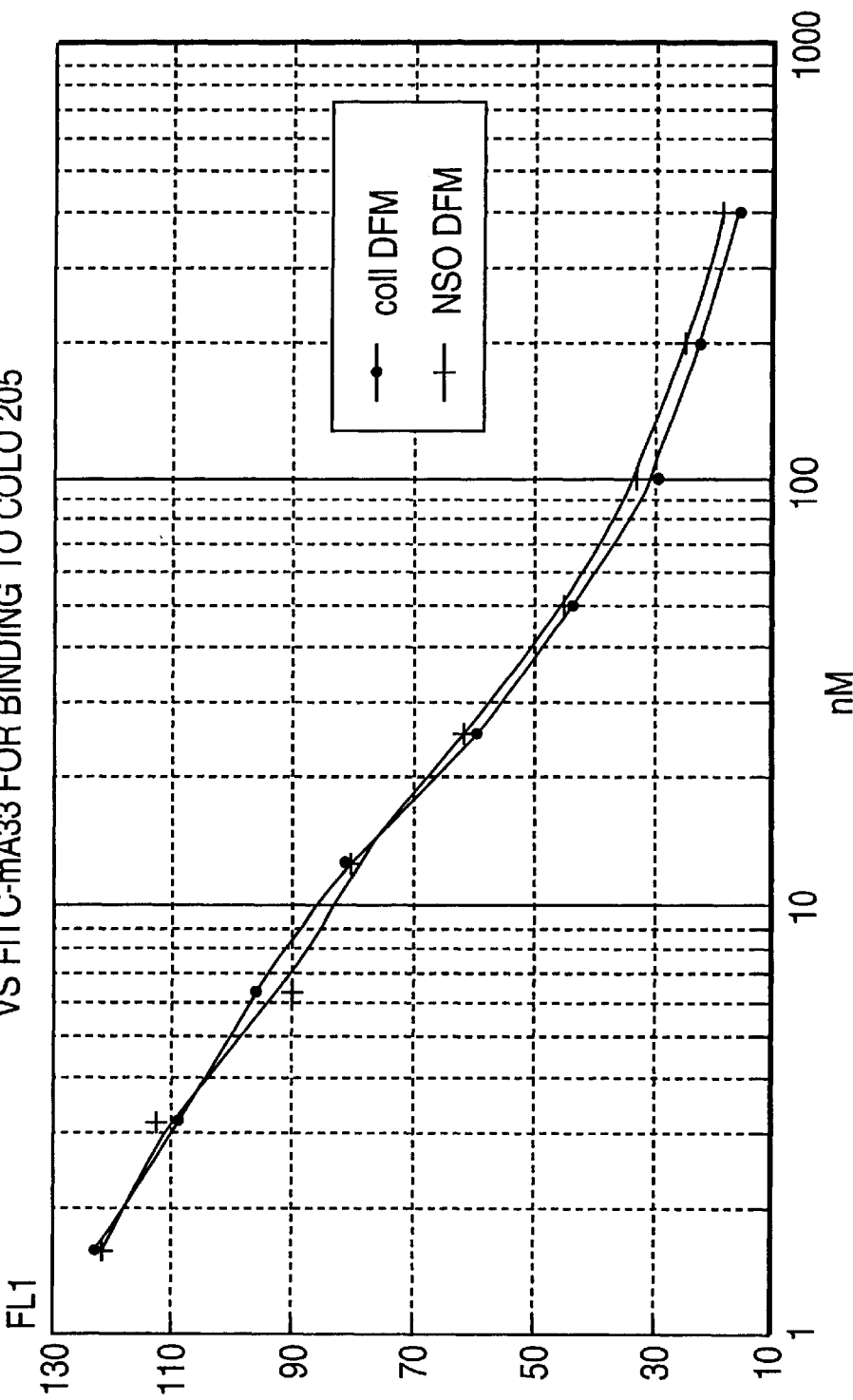

FIG. 18 shows the results of a competition assay in which hA33 TFM (+), hA33 DFM (□), hA33(γ1) (◇), or hA33 Fab'(γ4Δcys) (Δ) were used to compete for binding to Colo205 cells with FITC-label led murine A33. Residual FITC-mA33 bound to cells was measured in a FACScan analyser and fluorescence (Y axis) was related to input unlabelled antibody (X axis);

FIG. 19 shows the biodistribution at 48h post-injection, in LS174T tumour bearing nude mice, of 90Y labelled hA33 TFM(CT557)-12N4, hA33 DFM, and hA33(γ1)-12N4;

FIG. 20 shows the tumour:blood ratios of $^{90}$Y labelled hA33 TFM(CT557)-12N4, hA33 DFM, and hA33(γ1)-12N4 in LS174T tumour bearing nude mice at 24, 48 and 144 h post-injection;

FIG. 21 shows the biodistribtion of $^{90}$YmA33TFM(998)-12N4 conjugate in SW 1222 tumour bearing nude mice at 3, 24, 48, 72 and 144h post-injection;

FIG. 22 shows the improved tumour:blood ratios of $^{90}$YmA33TFM(998)-12N4 conjugate over IgG in SW 1222 tumour bearing nude mice at 3, 24, 48, 72 and 144h post-injection;

FIG. 23 shows the reduction in tumour volume over a period of 70 days in SW 1222 tumour bearing nude mice treated with $^{90}$YmA33TFM;

FIG. 24 shows the biodistribution of $^{90}$YmA33TFM (998)-12N4 conjugate in male Dunkin Hartley guinea pigs;

FIG. 25 is a schematic of the E. coli expression vector pMRR60. Only relevant restriction sites are shows;

FIG. 26 shows a western immunoblot of E. coli cell extracts after incubation overnight at a range of temperatures (for details see Example 3 in the text);

FIG. 27 shows a non-reduced western blot of E. coli cell extracts performed at 30° C. and 46° C. over the course of a fermentation from induction to harvest;

FIG. 28 shows a western immunoblot of E. coli cell extracts obtained by incubation in Tris-EDTA buffer (lanes 1 and 2) or by treatment with lysozyme (lanes 3–7);

FIG. 29 shows the results of a competition assay in which hA33 DFM prepared from N50 and E. coli cells were used to compete for binding to colo 2050 cells with FITC-labelled murine A33. Residual FITC-mA33 bound to cells was measured in a FACScan analyser and fluorescence (Y axis) was related to input unlabelled antibody (X axis); and FIG. 30 shows the biodistrbution of $^{125}$I hA33 DFM prepared from N50 and E. coli cells in L5174T tumour bearing nude mice at 24h post-injection.

In the Examples the following abbreviations are used:

C—chimeric h—humanised

L—light

H—heavy

γ4Δcys—IgG4 constant region containing one free thiol group in the hinge region, (see European Patent Specification No. 347433)

DFM—divalent monospecific binding protein comprising two Fab fragments bound to each other TFM—trivalent monospecific binding protein comprising three Fab fragments bound to each other HPLC high performance liquid chromatography CT 557 and CT 998 are as described previously above.

EXAMPLE 1

Assay Development

Assembled antibody in culture supernatants or in purified preparations was measured in an ELISA format assay (Whittle et at., 1987) using solid phase anti-Fcg chain to capture the chimeric antibody and mouse monoclonal antibody to human kappa chain linked to horseradish peroxidase (HRP) to reveal the bound antibody.

To demonstrate antigen binding both direct and competition format binding assays were used. In the direct binding assay ASPC-1 or Colo205 cells were incubated at 40° C. for 1 h. in the presence of various amounts of murine, chimeric or humanised A33, or non-specific antibody controls. After washing the cells to remove unbound antibody, the presence of bound antibody was revealed by further incubation with FITC-labelled anti-murine or anti-human Fc and by detection in the FACScan analyser (Becton Dickinson).

In competition format increasing amounts of the test antibody were co-incubated with saturating amounts of FITC-labelled murine antibody and the ASPC-1 or Colo205 cells as above. After washing the cells to remove unbound antibody, the binding of the FITC labelled murine antibody to the cells was detected in the FACScan analyser.

Cloning of A33 Variable Region Sequences

Murine A33 (IgG2a/k), (Welt et al., 1990), was obtained from culture of 1.5 L of hybridoma supernatant. (Atcc, HB 8779). 32.5 mg was purified by Protein A Sepharose. This material was used as assay standard and the separated heavy and light chains were subjected to N terminal sequencing.

The variable region sequences were obtained by the use of specific oligonucleotide primers (Jones and Bendig, 1990), modified to allow cloning into Celltech expression vectors (see FIG. 1 (SEQ ID NOS 5–29, respectively)), to amplify sequences in cDNA derived from polyA+ mRNA from the A33 hybridoma. Sequence amplification was done using the Polymerase Chain Reaction (PCR, Saiki et al., 1985), with denaturation, annealing and amplification conditions of 92° C., 1 min: 55° C., 1 min; 72° C., 1 min, with 30 cycles of amplification, and using the Taq Polymerase (Perkin Elmer-Cetus). 100 ng. of first strand cDNA synthesised using the Amersham International cDNA synthesis kit, and 10 pmoles of oligonucleotide primers were used in a 100 mL reaction volume.

Figure 2A:
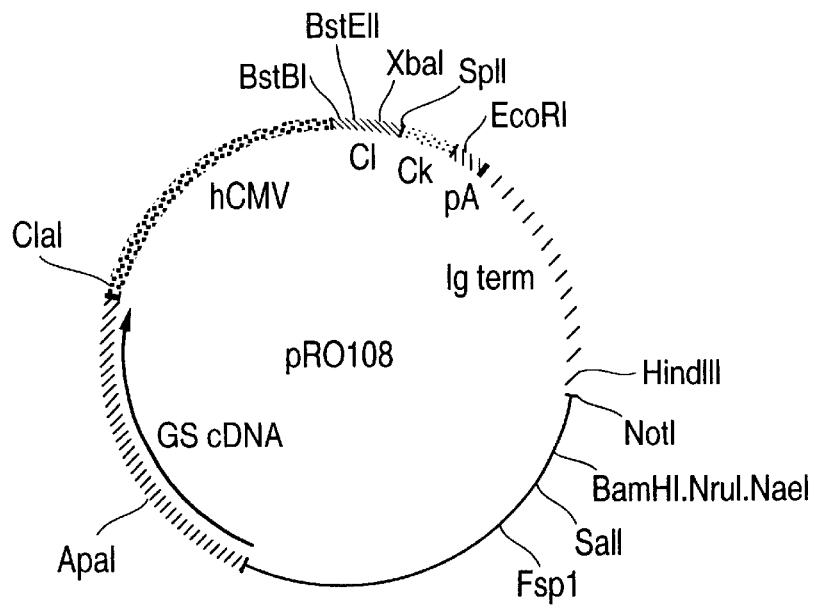
FIG. 2 is a schematic of the chimeric A33 expression vectors.
Figure 2B:
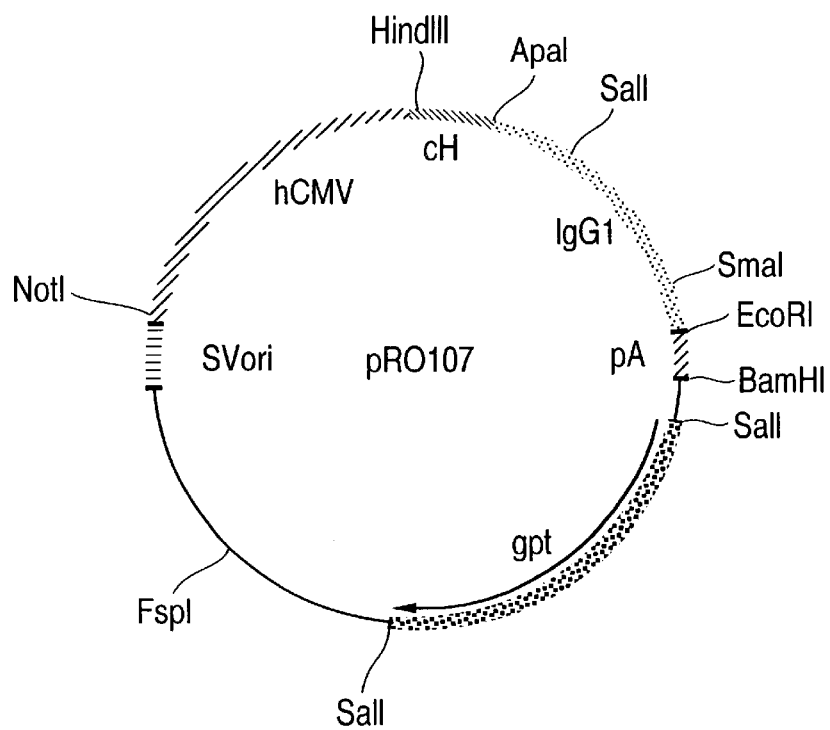

The PCR amplified products were cleaved with BstBI and SpII for the light chain and HindIII and ApaI for the heavy chain. These fragments were cloned into the human kappa light chain acceptor vector, pMRR1 5.1 and the human heavy chain, IgG1, acceptor vector, pMRR011 respectively to give chimeric expression vectors pRO108 for the light chain (FIG. 2) and pRO107 for the heavy chain (FIG. 2), respectively.

For each plasmid the variable regions from four independent clones were sequenced. For both variable regions the DNA sequence between the priming regions was the same in each of the four clones. Within the priming region sequence variability was seen, derived from the redundancy in the sequences of the primers used. For both heavy and light chains the deduced amino acid sequences obtained for the first 11 residues of the mature variable domain were in agreement with results of N terminal peptide sequencing of the murine antibody.

The DNA sequences were further confirmed by a second PCR experiment using forward primers that anneal in framework 1 (Orlandi et al. 1989). The sequences obtained agreed with those found in the first experiment. The amino acid sequences of the A33 light and heavy chain variable regions are shown in FIG. 3 (SEQ ID NOS 31–34 and 36–37, respectively).

Expression of Chimeric A33(γ1) to Demonstrate Activity

To confirm that the sequences obtained could combine to bind to the A33 antigen the chimeric expression plasmids pRO107 and pRO108 were transiently co-expressed in CHO-L761h cells (Cockett et al., 1990) at 200 mL scale. The resultant culture supernatant was shown to contain assembled antibody by ELISA assay. The antibody was purified by Protein A Sepharose chromatography and was shown to bind, in a concentration dependent manner, to ASPC-1 cells. The binding of the antibody to the cells was measured using FITC labelled anti-human IgG and the bound fluorescence was detected in a FACScan analyser.

Design of Humanised A33

The murine variable regions of A33 Were humanised according to the strategy described in Adair et al., (1991), and by reference to other recently published data on antibody humanisation (Co et al., 1991). The $V_H$ of A33 shows closest homology (70%) to the consensus sequence of human subgroup $V_H$III, while the $V_L$ shows greatest homology to the consensus sequence of $V_L$I and $V_L$IV (62%). From these subgroups LAY, which has a $V_H$III heavy chain and $V_L$I light chain, was chosen as the human framework. For the light chain residues 1–23, 35–45, 47–49, 57–86, 88 and 98–108 inclusive were derived from the LAY sequence, (numbering as in Kabat et al., 1987) and the residues 24–34, 46, 50–56, 87 and 89–97 inclusive were derived from the murine sequence. Residues 24–34, 50–56 and 89–97 correspond to the Complementarity Determining Regions (Kabat et al., 1987) (see FIG. 4). Residues 46 and 87 are predicted to be at the interface of the light and heavy variable regions. Residue 46 is usually a Leucine. Residue 87 is usually either a phenylalanine or tyrosine.

For the heavy chain residues 2–26, 36–49, 66–71, 74–82a, 82c–85, 87–93 and 103 to 113 inclusive were derived from the LAY sequence while residues 1, 27–35, 50–65, 72, 73, 82b, 86 and 94–102 inclusive were derived from the murine sequence (see FIG. 5). Residues 31–35, 50–65 and 95–102 in the heavy chain correspond to the Complementarity Determining Regions (Kabat et al., 1987). The murine derived amino acids in the framework regions were included for the following reasons. Residue 1 is usually solvent accessible and in the vicinity of the CDR region. LAY has a residue, alanine, not normally found at this position in human or murine $V_H$ sequences and therefore the murine residue was used. At positions 72 and 73 the murine residue was used because of the predicted proximity to CDR2 and also, in the case of residue 72, to remove the possibility of introducing an N-linked glycosylation site into the variable domain by the use of the LAY framework (see also Co et al., 1991; Law et al., 1991). The murine sequence was also used at the inter-domain residue 94, where A33 has a proline, not normally found at this position. Murine residues were used at positions 82b and 86 because the use of the human amino acids at these positions in a humanised antibody with LAY frameworks has previously been found to be deleterious for the expression of the heavy chain (International Patent Specification No. WO 92/010509).

Construction of Humanised A33 and Expression in CHO Transients

The humanised variable regions were assembled from overlapping oligonucleotides using a PCR assembly procedure (International Patent Specifications Nos WO 92.010509 and WO 92/011383, also Daugherty et al., 1991; Law et al., 1991). The oligonucleotides are given in FIG. 4 (SEQ ID NOS 38 and 45 respectively) for the light chain and FIG. 5 (SEQ ID NOS 47 and 54) for the heavy chain. The oligonucleotides were assembled using either 1 pmole of the longer internal oligonucleotides for the heavy chain variable region or 0.01 pmole for the light chain, with 10 pmole of the shorter terminal oligonucleotides in both cases. The reaction conditions were 30 cycles of 920C, 1 min; 550C 1 min; 72° C. 1 min using Taq polymerase. The PCR products were digested with the appropriate restriction enzymes as described for the chimeric antibody constructions and cloned into pMRRO15.1 for the light chain, and pMRRO11 for the heavy chain to give pCG16 and pRO109 respectively. pRO108 (cL expression vector) and pCG16 (hL expression vector) were each co-transfected with pRO107 (cH expression vector) or pRO109 (hH expression vector) into CHO L761h cells, and the antibody in the culture supernatant was calibrated and shown to compete for binding with FITC-labelled murine A33 for antigen on Colo205 cells by FAC-Scan analysis (FIG. 6). The relative potency of the fully humanised antibody was calculated to be 75% of that of the murine antibody based on the competition $IC_{50}$ values.

Construction of Stable Cell Lines in NSO For cA33(γ1), hA33(γ1), hFab'(γ4Δcys)

Expression vectors based on the GS amplification system (Bebbington et al., 1992; European Patent Specification No. 256055) were constructed for the chimeric A33 and the humanised A33 and also for a vector capable of producing a humanised Fab'(γ4Δcys) fragment.

The chimeric expression vector pGR50 (FIG. 7), capable of co-expressing both cL and cH chains, was constructed by combining a BamHI-Kpn1 fragment from the expression vector pEE13 with a Kpn1-Not1 fragment from pRO108, and a Not1-BamH1 fragment from pRO107.

pEE13 is an expression vector similar to pEE12 (Rolfe and Bebbington, 1992), in which a 1.7 Kbp Bcl1-BamH1DNA sequence containing the Immunoglobulin terminator fragment (Law et al., 1987) was cloned into the BamH1 site of pEE12 and clones with a resultant BamH1 site 3' to the terminator fragment were selected. The Kpn1-Not1 fragment from pRO108 contains a copy of the hCMV-MIE promoter/enhancer 5' to the chimeric light chain which is followed by SV40 polyadenylation sequences and the Ig terminator sequence (Law et a., 1987). The Not1-BamH1 fragment from pRO107 contains the chimeric A33(γ1) heavy chain between the hCMV-MIE promoter/enhancer and SV40 polyadenylation sequences.

The humanised A33 expression vector pAL71 (FIG. 7), capable of co-expressing both hL and hH chains, was constructed by obtaining a Not1-BamH1 vector fragment from pCG16 which contains the shuttle vector sequences, the GS cDNA selectable marker, a copy of the hCMV-MIE promoter/enhancer 5' to the humanised light chain which is followed by the SV40 polyadenylation sequences and the 1g terminator sequence. This vector fragment was combined with the Not1-BamH1 fragment from pRO109 which contains the humanised A33(γ1) heavy chain between the hCMV-MIE promoter/enhancer and the SV40 polyadenylation sequences.

The heavy chain fragment which combines with light chain to give an antibody Fab' fragment consists of the heavy chain variable domain, the CH1 domain and the hinge sequence (or derivative hinge sequence) and is known as the Fd' fragment. A modified Fd' sequence, in which the hinge sequence has been altered to substitute one of the cysteines for alanine, and so reduce the number of hinge cysteines to one is described in Bodmer et al., (1989) and is known as the Fd'(γ4ΔCys) sequence.

An expression vector capable of producing A33 hL and A33 hH-Fd'(γ4ΔCys), pAL72 (FIG. 7), was constructed by combining the Not1-BamH1 vector fragment from pCG16 with the Not1-Apa1 fragment from pRO109, which encodes the hCMV-MIE promoter/enhancer 5' to the the humanised A33 heavy chain variable region, along with IgG4 CH1 and hinge(DCys) sequences and SV40 polyadenyiation sequences on an Apa1-BamH1 fragment derived from the expression vector pAL49 (International Patent Specification No. WO 921010509).

Plasmids pGR50, pAL71, and pAL72 were linearised with Pvu1 for pGR50, or Fsp1 for pAL71 and pAL72, and 50 mg of DNA was used to transfect $10^7$ NS0 cells, by electroporation, using 1500 V and 3 mF with 2×1 sec. pulses. The cells were distributed into 96 well dishes at 5×10$^5$ cells in 50 mL, per well in CB2 medium supplemented with 10% dialysed, heat inactivated, foetal calf serum (10% dFCS) and 2 mM glutamine. After 24 h at 37° C., 5% $CO_2$ a further 100 mL of CB2 medium containing 10% dFCS, supplemented with 10 mM methionine sulphoximine (MSX) was added to each well. The cells were incubated for 2–3 weeks. Discrete colonies were observed after 19 days of culture. Culture supernatants were harvested from wells containing single colonies and antibody producing colonies were expanded for estimation of specific production rates (SPR) as picograms (pg) of antibody produced per cell, per 24 h of culture. The cell lines with the highest SPR values were taken for further analysis. Cell stocks were frozen and the cell lines were grown in by transfer into MM1 medium, containing <1% dialysed foetal calf serum, to produce culture supernatants for antibody purification. Some loss of productivity was seen initially with the cigG1 and higG1 cell lines but after culture in MM1 the productivity of the cell lines stabilised.

The highest producing cell lines were for the 8D3 (cA33 (γ1), SPR of 33 pg/cell24 h, accumulated yield of 35 mg/L from small scale culture), HC86.7 (hA33(γ1), SPR of 3 pg/cell24 h, accumulated yield of 36 mg/L from small scale culture) and HC87.21 (hA33 Fab'(γ4Δcys), SPR of 50 pg/cell24 h, accumulated yield of 112 mg/L from small scale culture and 170 mg/L from 1 5L scale fermentation).

in vivo Biodistribution Studies

1. Chimeric A33(γ1)

cA33(γ1) was purified from the NS0 cell line 8D3 using the method described for chimeric B72.3 (King et al., 1992). The purity of the cA33(γ1) was checked by SDS-PAGE and the activity shown to be equivalent to mA33 by competition experiments with FITC-labelled mA33 for binding to antigen on Colo205 cells analysed by FACscan.

The biodistribution of cA33(γ1) in nude mice bearing sub-cutaneous LS174T xenograft tumours was assessed when labelled with 111-indium. A 9N3 macrocycle for labelling with 111-indium was attached to purified cA33(γ1) using a 9N3-maleimide derivative (CT82, prepared from the compound of Example 2b in International Patent Specification No. WO 89/01475 and the N-hydroxysuccinimide ester of N-(2-carboxyethyl) maleimide). A sample of purified cA33(γ1) was buffer exchanged into 0.1M sodium bicarbonate buffer pH8 containing 2 mM EDTA. Thiol groups were then introduced into the cA33(γ1) by reaction with a 10 fold molar excess of 2-iminothiolane over cA33(γ1) for 30 minutes at room temperature. The thiolated cA33(γ1) was then desalted into 0.1M sodium bicarbonate buffer pH8 containing 2 mM EDTA using a column of Sephadex G-25 (Pharmacia PD-10) to remove the unreacted 2-iminothiolane. The number of thiol groups present were determined by titration with dithiodipyridine. 9N3 macrocycle was then conjugated to the thiolated cA33(γ1) by addition of CT82 at a ten fold molar excess over the number of thiol groups present followed by incubation at 37° C. for 2 hours. The conjugate was then purified by desalting on a Sephadex G-25 column (Pharmacia,PD-1 0) into 0.1 M sodium acetate pH5. Radiolabelling was achieved by the addition of 111-indium to the conjugate, ensuring that the buffer in the conjugate solution was sufficient to buffer the acidic 111 -InCl3. After incubation at 37° C. for 20 minutes the radiolabelling was quenched by the addition of 10 mM DTPA. The labelled cA33(γ1) was purified by gel filtration HPLC on a DuPont Zorbax GF-250 column in 0.2M phosphate pH7.

cA33(γ1) labelled with 111-indium was assessed by SDS-PAGE/autoradiography. There was no apparent breakdown of the cA33(γ1) by the labelling procedure. Groups of four female nude mice bearing subcutaneous 2–3 week old LS174T human tumour xenografts on the flank were injected i.v. in the tail vein with approximately 2 mg/6 mCi of cA33(γ1). Groups of animals were killed at 24 h, 48 h and 120 h for collection of tissues which were weighed, dissolved in 7M potassium hydroxide and counted in an LKB model 1270 gamma counter. Results were expressed as mean percentage of the injected dose per gram of tissue +/− standard deviation (n=4).

Results of the biodistribution experiment with 111-indium labelled cA33 demonstrated good tumour tocalisation (FIG. 8).

2. Humanised A33(γ1)

hA33(γ1) was purified from the NS0 cell line HC86.7 using the same method as for cA33(γ1). The purified antibody was shown to be active using the same competition assay format described above.

The biodistribution of hA33(γ1) in nude mice bearing sub-cutaneous Colo205 xenograft tumours was also assessed when labelled with 90-yttrium. A 12N4 macrocycle for labelling with 90-yttrium was attached to purified hA33 (γ1) using a 12N4-maleimide derivative (C177, prepared from the compound of Example 1b in International Patent Specification No. WO 89/01476 and the N-hydroxysuccinimide ester of N-(2-carboxyethyl) maleimide). A sample of purified hA33(γ1) was buffer exchanged into 0.1M sodium bicarbonate buffer pH8 containing 2mM EDTA. Thiol groups were then introduced into the hA33(γ1) by reaction, with a 10 fold molar excess of 2-iminothiolane over hA33(γ1) for 30 minutes at room temperature. The thiolated hA33(γ1) was then desalted into 0.1M sodium bicarbonate buffer pH8 containing 2 mM EDTA using a column of Sephadex G-25 (Pharmacia PD-10) to remove the unreacted 2-iminothiolane. The number of thiol groups present were determined by titration with dithiodipyridine. 12N4 macrocycle was then conjugated to the thiolated hA33(γ1) by addition of CT77 at a ten fold molar excess over the number of thiol groups present followed by incubation at 37° C. for 2 hours. The conjugate was then purified by desalting on a Sephadex G-25 column (Pharmacia,PD-10) into 0.1M potassium acetate pH6. Radiolabelling was achieved by the addition of 90-YCl₃ to the conjugate, ensuring that the buffer in the conjugate solution was sufficient to buffer the acidic 90-YCl₃. After incubation at 37° C. for 15 minutes the radiolabelling was quenched by the addition of 10 mM DTPA and the labelled hA33(γ1) purified by gel filtration HPLC on a DuPont Zorbax GF-250 column in 0.2M phosphate pH7.

hA33(γ1) labelled with 90-yttrium was assessed by SDS-PAGE/autoradiography. There was no apparent breakdown of the hA33(γ1) by the labelling procedure. Groups of four female nude mice bearing subcutaneous 2–3 week old Colo205 human tumour xenografts on the flank were injected i.v. in the tail vein with approximately 4 mg/1.8 mCi of hA33. Groups of animals were killed at 24 h, 48 h and 144 h for collection of tissues which were weighed, dissolved in 7M potassium hydroxide and counted in an LKB model 1270 gamma counter. Results were expressed as mean percentage of the injected dose per gram of tissue +/− standard deviation (n=4).

Results of this biodistribution experiment showed good tumour localisation of the hA33(γ1) with high tumour loading (FIG. 9).

Potency of humanised A33 (γ1 ) compared to murine A-3

The potency of hA33 (γ1) was compared to that of murine A33 by binding to cells of the human colerectal cancer cell line SW 1222. Fluorescently labelled conjugates of purified humanised and murine A33 were prepared to give approximately 1.5 molecules of fluorescein per antibody molecule. SW1222 cells (2.8×10⁵ per tube) were incubated with the fluorescent antibodies titrated in the range 3.57 µg/ml to 12 ng/ml in PBS with 5% foetal calf serum and 0.2% sodium azide on ice for 1.5 hours. After washing, antibody bound to the surface of the cells was detected by a FACscan (Becton Dickinson) as a fluorescent signal which was converted to numbers of antibody molecules bound per cell by calibration with fluorescent microbead standards. This data was used to generate Scatchard plots which showed that humanised and murine A33 were equally potent (FIG. 10).

Biodistribution of 90-yttrium labelled hA33 compared to cA33 and murine A33

Tumour loading was demonstrated in a further xenogratt system using the human colorectal cancer cell line SW1222. 12N4 macrocycle conjugates of hA33(γ1), cA33(γ1) and murine A33 were produced and labelled with 90-yttrium using the same procedures described above. Female nude mice bearing 2–3 week old subcutaneous SW1222 xenografts were injected i.v. in the tail vein with approximately 8 µg of the respective conjugates. Groups of four animals were killed at 24, 72 and 120 hours for collection of tissues which were weighed, dissolved in 7M potassium hydroxide and counted in a Packard cobra auto-gamma counter. Results were expressed as mean percentage of the injected dose per gram of tissue +/− standard deviation.

Results of this biodistribution experiment showed good tumour loading for all three conjugates, clearly demonstrating the equivalence of the murine, chimeric and humanised antibodies in this system (FIG. 11).

Biodistribution of hA33 labelled with 125-Iodine

A33(γ1) was labelled with 125-iodine using the Iodogen method to a specific activity of 0.8 µCi/4g and purified by gel filtration on Sephadex G-25 (Pharmacia, PD10).

Appoximately 10 µg/8 µCi of 125-iodine labelled hA33 was injected into groups of nude mice bearing SW1222 xenografts and the biodistribution determined at 3, 24, 48, 120 and 168 hours as described above.

Results or this experiment (FIG. 12) demonstrate good tumour localisation by 125-iodine labelled hA33.

Therapy study

The effectiveness of A33 in tumour therapy was assessed using the SW1222 tumour xenograft model. 12N4 macrocycle conjugate of A33 was prepared as described above and labelled with 90-yttrium to a specific activity of 3.2 $\mu$Ci/g using th, method described above except that the labelled protein was purified by gel filtration chromatography using a prepacked sephadex G-25 column (PD10. Pharmacia) rather than by the HPLC method. A 12N4 conjugate of the non-specific antibody MOPC21 was also prepared and labelled in the same manner. Groups of six female nude mice bearing 2–3 week old subcutaneous SW1222 xenografts were injected i.v. in the tail vein with approximately 78 $\mu$g/250 $\mu$Ci of each labelled conjugate. Tumour sizes in each animal were measured at the start of the experiment and at intervals thereafter.

Results of this experiment (FIG. 13) show a clear antitumour effect of the A33 conjugate which resulted in complete regression of tumours. Treatment with the non-specific control antibody was considerably less effective showing the benefit of tumour targeting by A33.

EXAMPLE 2

Purification of hA33 Fab'($\gamma$4$\Delta$cys) and Cross-Linking to Produce hA33 DI-Fab' (DFM) and Tri-Fab' (TFM)

hA33 Fab'($\gamma$4$\Delta$cys) (see Example 1) was purified from NS0 cell tissue culture supernatant by chromatography on protein A sepharose. A column of protein A sepharose was equilibrated with 100 mM boric acid buffer pH8.0 containing 150 mM sodium chloride. The tissue culture supernatant from NS0 cells expressing the hA33 Fab'($\gamma$4$\Delta$cys) was then adjusted to pH 8.0 by the addition of 1 M Tris and applied to the column. After washing with the equilibration buffer, the Fab' was eluted with 0.1 M citric acid collecting fractions directly into sufficient 1M Tris to adjust the pH of the fraction to between pH6 and pH7.

The purified Fab'($\gamma$4$\Delta$cys) was buffer exchanged into 0.1M sodium acetate/ citrate buffer pH6.0 containing 2 mM EDTA and concentrated to approximately 8mg/ml by ultrafiltration. Partial reduction was then carried out by adding b-mercaptoethylamine to 10 mM and incubating at 37° C. for 1 hour. The reducing agent was then removed by desalting on a column of Sephadex G-25 (PD-10) run in 0.1M potassium acetate buffer pH6.0 containing 2 mM EDTA.

The freshly reduced, desalted Fab'($\gamma$4$\Delta$cys) was cross-linked to produce di-Fab' using the cross-linker CT52 (Intermediate 6, European Patent Specification No. 384624). Cross-linker was added such that the Fab'($\gamma$4$\Delta$cys) was in a 2.2 fold molar excess over the cross-linker, and the reaction mixture incubated at 37° C. overnight. The extent of cross-linking was assessed using HPLC gel filtration on a DuPont Zorbax GF-250 column in 0.2M phosphate buffer pH7.0 and by SDS-PAGE (FIGS. 14, 17). Typically 50–60% of the Fab'(g4Dcys) was cross-linked to di-Fab' (DFM). The DFM was then purified by HPLC with a DuPont Zorbax GF-250×L column run in 0.2M phosphate pH7.0, and the purity assessed by SDS-PAGE.

The freshly reduced, desalted Fab'($\gamma$4$\Delta$cys) was also cross-linked to form the TFM with CT557 cross-linker (International Patent Specification No. WO 92122583). CT557 was dissolved in dimethylformamide at 1 mM. The CT557 solution was then added to the freshly reduced, desalted Fab'($\gamma$4$\Delta$cys) such that a 5 fold molar excess of Fab'($\gamma$4$\Delta$cys) over the CT557 concentration was maintained. After incubation at 37° C. overnight the extent of cross-linking was assessed by HPLC gel filtration and SDS-PAGE (FIGS. 15, 17). Typically 30–45% of the Fab'($\gamma$4$\Delta$cys) was cross-linked to TFM. The TFM was purified by gel filtration chromatography as described for the DFM above and the purity of the TPM preparation was then assessed using SDS-PAGE. hA33(Fab'($\gamma$4$\Delta$cys) TFM was also prepared with CT998 (international Patent Application No. PCT/GB 92/01047) (FIGS. 16,17).

The activity of the cross-linked humanised Fab'($\gamma$4$\Delta$cys) fragments was measured by competition with FITC-labelled murine A33 for binding to Colo205 calls by FACscan analysis. The results (FIG. 18) reveal that the DFM has approximately equivalent activity to the humanised IgG as expected, whereas the TFM shows advantageiously increased binding due to increased avidity, of the trivalent species.

Radiolabelling of hA33 DFM and TFM and Tumour Localisation in Animal Experiements hA33 DFM was prepared with the cross-linker CT52 (see above) which contains a 12N4 macrocycle for radiolabelling with 90-yttrium. hA33 TFM made with the CT557 cross-linker was conjugated to 12N4-maleimide (CT77) as described for hA33($\gamma$1) above in Example 1. Both DFM and TFM-12N4 were then radiolabelled with 90-Yttrium as described for the hA33($\gamma$1) above. hA33 DFM and TFM labelled with 90-yttrium were assessed by SDS-PAGE/autoradiography. There was no apparent breakdown of either OFM or TFM by the labelling procedure. The labelled DFM and TFM were then tested for tumour localisation compared to hA33 IgG1 prepared and labelled as described above. Groups of four female nude mice bearing subcutaneous 2–3 week old LS174T human tumour xenograits on the flank were injected i.v. in the tail vein with approximately 4.5 mg/15 mCi of TFM, 5 mg/12 mCi of DFM and 5 mg/2.3 mCi of IgG1. Groups of animals were killed at 24 h, 48 h and 144 h for collection of tissues which were weighed, dissolved in 7M potassium hydroxide and counted in an LKB model 1270 gamma counter. Results were expressed as mean percentage of the injected dose per gram of tissue +/− standard deviation (n=4).

Results of this biodistribution experiment showed good tumour localisation of the hA33($\gamma$1), OFM and TFM (FIG. 19). The DFM and TFM cleared faster than the IgG1 as expected, but still showed good tumour uptake, leading to improved tumour:blood ratios for the cross- linked fragments (FIG. 20).

Production and evaluation of mA33 Tri-Fab' (TFM)

Purified murine A33 was buffer exchanged into 0.2M acetate buffer pH4.2 containing 0.5M ammonium sulphate and digested to F(ab')$_2$ by addition of pepsin at a ratio of 1:50 (pepsin:antibody). After incubation at 37° C. for approximately 4 hours digestion was stopped by adjusting the pH of the mixture to 8 with 2M tris. The F(ab')$_2$ produced was purified firstly by passing through a column of protein A sepharose pre-equilibrated with and run in 50 mM glycine-glycinate buffer pH8.8 and secondly by gel filtration chromatography using a column of Sephacryl S-200HR run in 0.1M potassium acetate buffer pH6.0 containing 0.2M potassium chloride and 2 mM DTPA. Purified F(ab')$_2$ was used to produce mA33 TFM with CT998 by initially selectively reducing the hinge to produce Fab'. This was achieved by firstly butter exchanging F(ab')$_2$ into 0.1M sodium phosphate buffer pH 7.95 containing 2 mM DTPA followed by incubation with 10 mM b-mercaptoethylamine for 30 minutes at 37° C. The Fab' produced was desalted into 0.1M sodium phosphate buffer pH 6.9 containing 2 mM DTPA to remove the reducing agent and the CT998 cross-linker was added to the freshly desalted Fab', in multiple additions over an 18 hour period at 37° C., to a final ratio of 1.1:1 (Fab':CT998). The extent of cross-linking was determined by HPLC gel filtration analysis and typical yields of murine A33 TFM were 8–20% of the total protein. The murine A33 TFM was then purified by HPLC gel filtration using a DuPont GF-250XL column run in 0.2M sodium phosphate containing 2 mM DTPA pH 7.0.

A biodistribution experiment was carried out with 90-yttrium labelled mA33 TFM to assess tumour targeting. mA33 TFM was labelled with 90-yttrium by firstly desalting on a Sephadex G-25 column (Pharmacia, PD10) into 0.1M potassium acetate pH6.0 followed by incubating with 90-YCl3 ensuring that the buffer in the TFM preparation was sufficient to buffer the acidic 90-YCl$_3$. After incubation at room temperature for 15 minutes the radiolabelling was quenched by the addition of 10 mM DTPA and the labelled TFM purified by HPLC gel filtration on a DuPont Zorbax GF-250 column in 0.2M phosphate pH7.0. A biodistribution experiment was then carried out using female nude mice bearing SW1222 xenografts as described above. In this experiment 90-yttrium labelled mA33 TFM was compared to 90-yttrium labelled mA33 IgG prepared and labelled as described above. Injections of approximately 7 μg/21 μCi IgG and 8 μg/12 μCi of TFM were carried out. Results of this experiment show good tumour localisation for the murine TFM with improved tumour:blood ratios over IgG (FIGS. 21 and 22).

The ability to treat tumours with murine A33 TFM was then assessed in a SW1222 tumour xenograft therapy study as carried out for IgG (Example 1). TFM was labelled with 90-yttrium to a specific activity of 3 μCi/μg using the method described above except that the labelled protein was purified by gel filtration chromatography using a prepacked sephadex G-25 column (PD10. Pharmacia) rather than by the HPLC method. Purity of the labelled protein was subsequently checked by HPLC and SDS-PAGE/autoradiography and found to be high. A group of six female nude mice bearing 2–3 week old subcutaneous SW1222 xenografts were injected i.v. in the tail vein with approximately 100 μg/300 μCi of labelled TFM. Tumour sizes in each animal were measured at the start of the experiment and at intervals thereafter.

Results of this experiment (FIG. 23) demonstrate that A33 TFM is effective in tumour therapy.

Biodistribution of hA33 TFM

The biodistribution of hA33 TFM was also assessed in guinea pigs. hA33 TFM was prepared and radiolabelled with 90-yttrium as described above. Approximately 10 μg/20 μCi of 90-yttrium labelled hA33 TFM was injected into groups of male Dunkin Hartley guinea pigs via the ear vein. Groups of four animals were killed at 3, 24, 48 and 144 hours for collection of tissues which were weighed, dissolved in 7M potassium hydroxide and counted in a Packard cobra autogamma counter. Results were expressed as mean percentage of the injected dose per gram of tissue +/- standard deviation.

The results of this biodistribution (FIG. 24) demonstrate that hA33 TFM clears from the blood rapidly and does not accumulate in any non-specific tissues. This suggests that hA33 TFM has favourable biodistribution properties for in vivo applications.

EXAMPLE 3 a) Constructions of Vectors for *E. coli* Expression

The construction of vectors for the expression and secretion from *E. coli* of the humanised A33 as a Fab' (γ4Δcys) was accomplished in a number of steps. In a first step the hL gene and the hH-Fd (γ4Δcys) gene were reconstructed to replace the 1g signal sequences with those from the ompA protein (Skerra and Pluckthun, 1989).

The vector pSKompA was digested with Nru1, within the signal sequence coding region, and EcoR1 was used to clone both the hL gene and the hH-Fd'(γ4Δcys) gene. The human kappa constant region was isolated from pMRRO10 (International Patent Specification No. WO 92/01059) as an SpI1-EcoRI fragment and the humanised V$_L$ region was obtained in a PCR reaction using primer 5' AAA.AAG.A-CA.GCT.ATC.GCG.ATT.GCA GTG.GCA.CTG.GCT.G-GT.TTC.GCT.ACC.GTA.GCG.CAA.GCT.GAT. ATC.CA-G.ATG.ACT.CAG 3' and primer 5' CCG.GCC.CGT.ACG.TTT. TAC.TTC 3' (SEQ ID NOS 1 and 2, respectively) to amplify the V$_L$ sequence from pCG16, at the same time attaching to the mature V$_L$ sequence the C terminal sequence of the ompA signal from the Nru1 site. The PCR fragment was cleaved with Nru1 and SpI1 to expose the cloning sites and the fragment was cloned. along with the SpI1-EcoR1 human CK fragment into the Nru1-EcoR1 cut pSKompA vector to give pMRRO55.

DNA sequences coding for the human CH1 and hinge (Δcys) domains, terminating in inframe stop signals were isolated as an Apa1-EcoR1 fragment from pMRRO22 (International Patent Specification No. WO 93/06231) The humanised VH fragment was obtained in a PCR reaction using primer 5' AAA.AAG.ACA.GCT.ATC.GCG.ATT.G-CA.GTG.GCA. CTG.GCT.GGT.TTC.GCT.ACC.G-TA.GCG.CAA.GCT.GAG.GTG.CAG. CTG.CTG.GAG 3' (SEQ ID NO: 3) and primer 5' GCG.CGC.GGG.CCC.T-TC.GTT.GAG 3' SEQ ID NO: 4 to amplify the V$_H$ sequence from pRO109. at the same time attaching the C terminal sequence of the ompA signal from the Nru1 site to the mature V$_H$ sequence. The PCR fragment was cleaved with Nru1 and Apa1 to expose the cloning sites and the fragment was cloned along with the Apa-EcoR1 human CH1 and hinge (Δcys) coding DNA fragment in to the Nru-EcoR1 cut pSKompA vector to give pMRR54.

An expression plasmid based on the medium copy number plasmid pACtac (International Patent Specification No. WO 92/01059) was constructed as follows. The ompA-hH-Fd'(Δcys) gene was isolated from pMRR54 as a Xba1-Sma1fragment and cloned into a Xba1-Pvu2 cut vector fragment of pSP73, (Promega Corporation) to give pMRR56, so as to allow the subsequent manipulation of the ompA-hH-Fd'(Δcys) gene as an EcoR1 xfragment.

The ompA-hL gene was isolated as an Xho1-EcoR1 fragment from pMRR55 and cloned into a Sal1-EcoR1 (partial) vector fragment of pACtac (partial EcoR1 digesion is required because of a second EcoR1 site in the chloramphenicol acetyl transferase gene) to give pMRR58. pMRR58 was digested partially with EcoR1, (treated with calf intestinal alkaline phosphatase to remove 5' phosphate groups) CIP'ed, and used as vector for the insertion of the ompA-hH-Fd'(Δcys) gene as an EcoR1 fragment isolated from pMRR56. After transformation competent *E coli* clones were identified by restriction mapping. A plasmid with the ompA-hH-Fd' (Δcys) gene at the correct location and in the correct orientation was named pMRR60. The final expression vector configuration of pMRR60 is shown in FIG. 25 pMRR60 was transformed into *E. coli* strain W3110 (ATCC strain 2735).

b) Expression of A33 grafted Fab in *E. coli*

*E. coli* strain W3110 (pMRR60) was grown in fermenters of various capacities as described below.

Inocula for all fermentations were prepared from frozen glycerol stocks in LB medium (see below) containing chloroamphenicol. The seeding density was usually 300 ml glycerol stock per litre LB. Inoculum cultures, grown in Erienmeyer flasks (1 L containing 200 mL medium) incubated at 30° C. and 250 RPM in an orbital shaker were used when an OD 600 nm of 3 had been attained (normally 12–16h). Fermenters and shake flasks were seeded with 5–10% volumes of inoculum.

Media and media components used for inoculum cultures and subsequent fermentations were prepared and used as follows.

LB: Luria Broth
LB Cm: LB+chloramphenicol 25 mg/ml

| SM6B | |
|---|---|
| Component | g/L |
| $(NH_4)_2SO_4$ | 5.0 |
| $NaH_2PO_4$ | 6.24 |
| KCl | 3.87 |
| $MgSO_4.1H_2O$ | 0.56 |
| Citrate | 4.0 |
| SM6A Trace Element solution | 10 ml/L |
| Antifoam (Mazu DF843 10% in $H_2O$) | 1.0 ml/L |
| Made up to 0.2 L with deionised water (5x solution) | |

| SM6B Trace element solution | |
|---|---|
| Component | g/L 100x stock solution |
| Citrate | 100.0 |
| $CaCl_2.6H_2O$ | 5.0 |
| $ZnSO_4.4H_2O$ | 2.0 |
| $MnSO_4.4H_2O$ | 2.0 |
| $CuSO_4.5H_2O$ | 0.5 |
| $CoSO_4.6H_2O$ | 0.4 |
| $FeCl_3.6H_2O$ | 9.67 |
| $H_3BO_3$ | 0.03 |
| $NaMoO_4$ | 0.02 |

Made up to 1 l with deionised water. Components were added in the order shown and were allowed to dissolve completely prior to the addition of the next salt.

Medium SM6B was kept as a 5× solution, the concentrated salts solution was added to the fermenter to the correct concentration for the culture volume up to the point of induction (i.e. sterilised volume+inoculum+ glucose feeds). Subsequent salt requirements arising from the increase in volume brought about by feeding lactose solution were supplied at the time of lactose feeding. The fermenter was brought up to the correct volume pre sterilisation with deionised water.

Defined media were brought to pH 6.95 using 3.6M $NH_4OH$ after autoclaving in situ at 121° C. for 20 min. After sterilisation of the salts solution, glucose was added to the fermenter as a 50% (w/v) solution to a final concentration of 20 g/L.

Glucose and lactose were autoclaved separately as 50% solution (w/v) in $H_2O$ and added to cultures as described in the fermentation methods section. Prior to autoclaving, conc $H_2SO_4$ (100 ml per litre) was added to glucose solutions.

Casamino acids (Difco, 200 g/l) solution in $H_2O$ sterilised by autoclaving) were added to the fermenter at the start of lactose feeding to give a final accumulated supply of 20 g/L (final fermenter volume).

Fermentations (2 L. 15 L and 150 L) of *E. coli* W3110 (pMRR60) were carried out in medium SM6B. Glucose was used as the initial carbon and energy source for all fermentations and was added after medium sterilisation to a concentration of 20 g/l. Culture pH was brought to and maintained at 6.95 by the addition of 3.6M $NH_4OH$ or 2M $H_2SO_4$.

Dissolved oxygen tension (DOT) was maintained above 10% air saturation by control of agitator speed (between 250 and 1000 RPM for 2 and 15 L fermentations and between 150 and 650 RPM for 150 L fermentations). Culture temperature was maintained at 30° C. throughout the fermentation. Cultures were aerated at 0.75–1.5 v/v/min. During the later stages of 150L fermentations the vessel was pressurised to 0.4 bar to maintain the dissolved oxygen tension above 10%. Oxygen utilisation rates (OUR) and carbon dioxide evolution rates (CER) were determined from exhaust gas analysis values carried out by mass spectrometry. OUR reached maximum values of approx. 150 mmol/l/h in the fermentations described.

Induction of product expression was initiated by switching the carbon source to lactose from glucose. Glucose was fed to support the culture to an OD of approximately 40 (an accumulative addition of 40 g/l). Lactose feeding was started at an OD of approximately 35, and was fed as individual shots of 60% lactose to a concentration of up to 60 g/l culture when required or as a predetermined exponential feed program. Where casamino acids were added, these additions were made or started, at the start of lactose feeding.

Fermenters were harvested 24 h after the switch to lactose utilisation. 2 L Fermentations were clarified by centrifugation at 4200 RPM rmax 250 mm. 15 and 150 L Fermentations were clarified by tangential flow filtration (TFF) using a Millipore prostack system with durapore 0.65 mm membranes and a retentate flow rate of approx. 10 L/min/channel.

Product was selectively released from the periplasm by incubating culture pellets or concentrated cell suspensions harvested by centrifugation or TFF respectively. Harvested cells were washed in Tris HCl buffer 100 mM pH 7.4 and then incubated in Tris buffer 100 mM pH 7.4 containing 10 mM EDTA. Incubations were carried out at 40° C. for 4 h. Repeated incubations of the cells produced further material. Alternatively, cell lysis by enzymatic [e.g. lysozyme] or mechanical means was found to release more active hA33 product than the selective release of product using EDTA.

A western immunoblot of cell extracts incubated at a range of temperatures up to 46° C. is shown in FIG. 26. The samples were run reduced and non reduced to reveal a range of assembled and partially degraded hA33 Fab. This set of extractions was prepared by incubating the intact cells overnight in Tris HCl buffer 100 mM pH 7.4 containing EDTA 10 mM.

In the Figure:

lanes 1–5 samples were reduced with 2-mercaptoethanol
lanes 6–10 were run non-reduced.
lanes 1 and 6 were loaded with an extraction carried out at 4° C., 2 and 7 at 30° C., 3 and 8 at 43° C., 4 and 9 at 44° C. and
lanes 5 and 10 at 46° C.

The bands labeled on the non-reduced side are:

1 Assembled intact Fab
2 and 3 Partially degraded Fab
4 Intact heavy and light chains The titre of protein obtained in the 5 extracts was determined by a dye binding assay kit (Pierce) and found to be 1.06, 0.7, 0.66, 0.28 and 0.26 g/l for extracts made at 4, 30, 43, 44 and 46° C. respectively. Activity of the protein was shown to be equivalent to mA33 Fab using the competition assays described in Example 1.

FIG. 27 shows a western immunoblot of cell extracts obtained by incubation in Tris HCl/EDTA buffer at 30° C. (lanes 1–8) and 46° C. (lanes 10–17). The samples loaded represent a time course across a fermentation of *E. coli* W3110 (pMRR60).

Advantageously, predominantly single banded material was obtained in the samples extracted at 46° C. while 4 principal bands were obtained in the samples extracted at 30° C., illustrating that a simple heat treatment could be used to obtain substantially pure hA33 Fab, free of partially degraded Fab and separate light and heavy chain materials.

The use of an elevated extraction temperature to obtain hA33 Fab from *E. coli* W3110 (pMRRR60) of the correct assembled molecular weight free of unwanted fragments and single chains is further illustrated in FIG. 28 which shows Western immunoblots of cell extracts obtained by incubation in Tris/EDTA buffer, (lanes 1 and 2) or by treatment with lysozyme (lanes 3–7).

lane 1 extraction carried out at 30° C.
lane 2 extraction carried out at 46° C.
lanes 3–7 lysozyme treatment of cell pellets post incubation at 46° C.

Preparation and evaluation of hA33 DFM from *E. coli* hA33 Fab' was purified from *E. coli* cell lysate after heat treatment as described above. Cell lysate was centrifuged to remove debris and the supernatant heat treated at 46° C. for 24 hours. After centrifugation at 10,000 rpm for 30 minutes the supernatant was made 0.1M in boric acid and the pH adjusted to 8 with 5M sodium hydroxide. The Fab' was then purified by applying the supernatant to a column of protein A sepharose pre-equilibrated in 0.1M borate pH 8 and the column washed with the same buffer. Fab' was then eluted from the column with 0.1M citric acid. The eluent containing the Fab' was adjusted to pH 6 with 2M tris.

Purified hA33 Fab' was then chemically cross-linked to di-Fab (DFM). The purified Fab' was concentrated by ultrafiltration and buffer exchanged into 0.1 M potassium acetate pH6. Fab' was then reduced by the addition of β-mercaptoethylamine to 11 mM and incubated at 37° C. for 30 minutes. Reducing agent was removed by desalting on a Sephadex G-25 column (Pharmacia, PD10) into 0.1M potassium acetate pH6 and cross-linking initiated by the addition of CT52 (see above) to a 2.2 fold molar excess of Fab' over CT52. The DFM produced was then purified as described for DFM from NS0 derived Fab' in Example 2.

hA33 DFM from NS0 cells was prepared as described in Example 2 and compared to the *E. coli* derived material for relative potency. Titrations of hA33 DFM which had been prepared from NSO-derived or *E. coli* derived Fab' were incubated with a saturating concentration of FITC-conjugated murine A33 IgG in the presence of colo 205 cells. Incubation media included 0.20o sodium azide to avoid any effects due to internalisation of the antibodies. Cells were washed and bound FITC-labelled antibody measured in a FACscan (Becton Dickinson). DFM molecules were used in this comparison to avoid any differences in binding which could be attributed to avidity effects resulting from different proportions of contaminating F(ab')$_2$ in univalent Fab' preparations. Results from this experiment are shown in FIG. 29 and demonstrate that binding sites from NS0 and *E. coli* are equally potent.

Results of this experiment demonstrate that DFM prepared from hA33 Fab' made in *E. coli* is equivalent to material produced in mammalian cells. To test whether DFM from E. coli and NS0 derived hA33 Fab' were equivalent in vivo a biodistribution experiment was carried out using female nude mice bearing LS174T xenografts. The DFM preparations were labelled with 125-iodine using Bolton-Hunter reagent (Amersham) to a specific activity of approximately 0.15 µCi/µg.

Approximately 3 µg/0.4 µCi of 125-iodine labelled DFM from *E. coli* or NS0 cells were injected into groups of four female nude mice bearing 2–3 week old subcutaneous LS174T xenografts and the biodistribution assessed at 24 hours as described above.

Results of this experiment demonstrate that DFM prepared from hA33 Fab' from *E. coli* has an equivalent biodistribution to material produced in NS0 cells (FIG. 30).

REFERENCES

Adair, J. R., Athwal, D. S., Emtage, J . S ., 1991.Humanised antibodies. WO91/09967

Amit, A. G., Mariuzza, R. A., Phillips, S. E. V., Poljak, R. J., 1986. Three dimensional structure of an antigen-antibody complex at 2.8 A resolution. Science., 2,3, 747–753

Baker, T. S., Begent, R. H. J., Dewji, M. R., Conlan, J., Secier, D. S.,1991. Characterization of the antibody response in patients undergoing radioimmunotherapy with Chimeric 672.3. Antibod. Immunoconj. Radiopharm., 4 ,799–809

Bebbington, C. R., Renner, G., Thomson, S., King, D., Abrams, D., Yarranton, G. T., 1992. High-level expression of a recombinant antibody from myeloma cells using a glutamine synthetase gene as an amplifiable selectable marker. Bio/Technology, 10, 169–175

Begent, R, H, J., Ledermann, J. A., Bagshawe, K. D., Green, A. J., Kelly, A. M. B., Lane, D., Secher, D. S., Dewji, M. R., Baker, T. S., 1990. PhaseI/II study of Chimeric 672.3 antibody in radioimmunotherapy of colorectal carcinoma. Br. J. Cancer, 62, 487

Bhat, T. N., Bentley, G. A., Fischmann, T. O., Boulot, G., Poijak, R. J., 1990. Small rearrangements in structures of Fv and Fab fragments of anitibody D1.3 on antigen binding. Nature, 347, 483–485

Bodmer, M. W., Adair, J. R., Whittle, N. R., 1989. Recombinant antibody WO89/01974

Boulot, G., Eisele, J. -L. Bentley, G. A., Bhat, T. N., Ward, E. S., Winter. Ge., Poljak, R. J., 1990. Crystallisation and preliminary X-ray diffraction study of the bacterially expressed Fv from the monoclonal anti-lysozyme antibody D1.3 and of its complex with the antigen lysozyme. J. Mol. Biol., 213, 617–619

Boulot, G., Rojas, C., Bentley. G. A., Poijak, R. J., Barbier, E., Le Guern, C., Cazenave, P. A., 1987. Preliminary crystallographic study of a complex between the Fab fragment of a monoclonal anti-lysozyme antibody (D1.3) and the Fab fragment from an anti-idiotypic antibody against D1.3 J. Mol. Biol., 194, 577–579

Carter P., Presta, L., Gorman, C. M., Ridgway, J. B. B., Henner, D., Wong, W. L. T., Rowland, A. M., Kotts, C., Carver, M. E., Shepard, H. M., 1992. Humanization of an anti-p185HER2 antibody for human cancer therapy. Proc. Natl. Acad. Sci.,USA., 89, 4285–4289

Co. M. S., Avdalovic, N. M., Caron, P. C., Avdatovic, M. V., Scheinberg, D. A., Queen, C. 1992. Chimeric and humanized antibodies with specificity for the CD33 antigen. J. Immunol., 148, 1149–1154

Co, M. S., Deschamps, M., Whitley, R. J., Queen, C., 1991. Humanized antibodies for antiviral therapy. Proc. Natl. Acad. Sci. USA, 88, 2869–2873

Cockett, M. I. C., Bebbington, C. R., Yarranton, G. T., 1990. High-level expression of tissue inhibitor of metalloproteinases in Chinese hamster ovary cells using glutamine synthetase gene amplification. Bio/Technology, 8, 662–667

Colman, P. M., Laver, W. G., Varghese, J. N., baker, A. T., Tulloch, P. A., Air, G. M., Webster, R. G., 1987. Three-dimensional structure of a complex of antibody with influenza virus neuraminidase. Nature, 326, 358–363

Crowe, S., 1992. The CAMPATH study: A review. in Monoclonal Antibodies. State-of the Art in research and potential clinical applications, London (Abstract)

Daugherty, B. L., DeMartino, J. A., Law, M. -F., Kawka, D. W., Singer, I. I., Mark, G. E., 1991. Polymerase chain reaction facilitates the cloning, CDR-grafting and rapid expression of a murine monoclonal antibody directed against the CD18 component of leukocyte integrins. Nucl. Acids Res., 19, 2471–2476

Davies, D. R. Sheriff, S., Padlan, E., 1989. Comparative study of two Fab-lysozyme crystal structures. Cold Spring Harbor Symp. Quant. Biol., 54, 233–238

Ghrayeb, J., Knight, D. M., Looney, J. E., 1991. Chimeric immunoglobulin for CD4 receptors WO 91/10722

Hakimi, J., Chizzonite, R., Luke, D. R., Familletti, P. C., Bailon, P., Kondas, J. A., Pilson, R. S., Lin, P., Weber, D. V., Spence, C., Mondini, L. J., Tsien, W. -H., Levin, J. E., Gallati, V. H., Korn, L., Waldmann, T. A., Queen, C., Benjamin, W. R., 1991. Reduced immunogenicity and improved pharmacokinetics of humanized anti-Tac in cynomolgus monkeys. J. Immunol., 147, 1352–1359.

Hale, G., Dyer, M. J., Clark, M. R., Phillips, J. M., Marcus, R., Riechmann, L, Winter, G., Waldmann, H., 1988. Remission induction in Non-Hodgkin lymphoma with reshaped human monoclonal antibody CAMPATH-1 H Lancet, ii, 1394–1399

Hird, V., Verhoeyen, M., Badley, R. A., Price, D., Snook, D., Kosmas. C., Gooden, C., Bamias, A., Meares, C., Lavender, J. P., Epenetos, A. A., 1991. Tumour localisation with e radioactively labelled reshaped human monoclonal antibody. Br. J. Cancer, 64, 911–914

Jones, P. T., Dear, P. H., Foote, J., Neuberger, M. S., Winter, G., 1986. Replacing the complementarity-determining regions in a human antibody with those from a mouse. Nature, 321, 522–525

Jones, S. T., Bendig, M. M., 1991. Rapid PCR-cloning of full length mouse immunoglobulin variable regions. Bio/Technology, 9, 88–89

Kabat, E. A., Wu, T. T., Reid-Miller, M., Perry, H. M., Gottesman, K. S., 1987. Sequences of proteins of immunological interest.4th edition.Washington DC: United States Department of Health and Human Services Khazaeli, M. B., Saleh, M. N., Liu, T. P., Meredith, R. F., Wheeler, R. H., Baker, T. S., King, D., Secher, D., Allen, L., Rogers, K., Colcher, D., Schiom, J, Shochat. T, D., LoBuglio, A. F., 1991. Pharmacokinetics and immune response of 131l-Chimeric mouse/human B72.3 (human gamma 4) monoclonal antibody in man. Cancer Res., 51, 5461–5466

King, D. J., Adair, J. R., Angal, S., Low, D. C., Proudtoot, K. A., Lloyd, J. C., Bodmer, M. Yarranton, G. T., 1992. Expression, purification and characterisation of a mouse: human Chimeric antibody and Chimeric Fab' fragment. Biochem. J., 281, 317–323

Knox, S. J., Levy, R., Hodgkinson, S., Bell, R., Brown, S., Wood, G. S., Hoppe, R., Abel, E. A., Steinman, L., Berger, R. G., Gaiser, C. Young, G., Bindl, J., Hanham, A., Reichert, T., 1991. Observations on the effect of Chimeric anti-CD4 monoclonal antibody in patients with Mycosis Fungoides. Blood, 77, 2–30

Kurrie, R., Shearman, C. W., Moore, G. P., Seiler, F., 1990. Improvea monoclonal antibodies against the human alpha/beta T-cell receptor, their production and use. EP 0403156

Law R., Kuwabara, M. D., Briskin, M., Fasel, N., Hermanson, G., Sigman. D. S., Wall, R., 1987. Protein-binding site at the immunoglobulin membrane polyadenylation signal: Possible role in transcription termination. Proc. Natl. Acad. Sci. USA, 84, 9160–9164

Law, M. -F., Mark, G. E., III, Williamson, A. R., 1991. Method for producing recombinant immunoglobulins. EP 0438310

LoBuglio, A. F., Wheeler. R. H., Trang, J., Haynes. A., Rogers, K., Harvey, E. B., Sun, L. Ghrayeb, J., Khazaeii, M. B.1989. Mouse/human Chimeric monoclonal antibody in man: Kinetics and immune response. Proc. Natl. Acad. Sci. USA, 86, 4220–4224

Maniatis et al, Molecular Cloning, Cold Spring Harbor, New York 1982.

Mathieson, P. W., Cobbold, S. D., Hale, G., Clark, M. R., Olivera, D. B., Lockwood, C. M., Waldmann, H., 1990. Monoclonal antibody therapy in systemic vasculitis. New Engl. J. Med., 323, 250–253

Meredith, R. F., Khazaeli, M. B., Plott, W. E., Saleh, M. N., Liu, T., Allen, L. F., Russell, C. D., Orr, R. A., Colcher, D., Schlom, J., Shochat, D., Wheeler, R. W., LoBuglio, A. F., 1992. Phase I trial of Iodine-131-Chimeric B72.3 (human IgG4) in metastatic colorectal cancer. J. Nucl. Med., 33, 23–29

Meredith, R. F., LoBughio, A. F., Plott, W. E., Orr, R. A., Brezovich, I. A., Russell, C. D., Harvey, E. B., Yester, M. V., Wagner, A., J., Spencer, S. A., Wheeler, R. H., Saleh, M. N., Rogers, K. J., Polansky, A., Salter, M. M., Khazaeli, M. B., 1991. Pharmacokinetics, immune response, and biodistribution of Iodine-131-labeled Chimeric mouse/human IgG1, k 171 A monoclonal antibody. J. Nucl. Med., 32, 1162–1168

Moi, M. K., Meares, C. F., DeNardo, S. J., 1988. The peptide way of macrocyclic bifunctional chelating agents: Synthesis of 2-(p-Nitrobenzyl)-1,4,7,10-tetraazacyclododecane-N,N',N'',N'''-tetraacetic acid, and study of its Yttrium (III) complex. J. Am. Chem. Soc., 110, 6266–6267

Morrison, S. L., Johnson, M. J., Herzenberg, L. A., Oi, V. T., 1984. Chimeric human antibody molecules: Mouse antigen-binding domains with human constant region domains. Proc. Natl. Acad. Sci. USA., 81, 6851–6855

Orlandi, R., Gussow, D. H., Jones, P. T., Winter, G., 1989. Cloning immunoglobulin variable domains for expression by the polymerase chain reaction. Proc. Natl. Acad. Sci. USA., 86, 3833–3837

Padlan, E. A., 1991. A possible procedure for reducing the immunogenicity of antibody variable domains while preserving their ligand-binding properties. Mol. Immunol., 28, 489–498

Padlan, E. A., Silverton, E. W., Sheriff, S., Cohen, G. H., Smith-Gill, S. J., Davies, D. R., 1989. Structure of an antibody-antigen complex: Crystal structure of the HyHEL-10 Fab-lysozyme complex. Proc. Natl. Acad. Sci. USA., 86, 5938–5942

Poijak, R. J., 1991. Structure of antibodies and their complexes with antigens. Mol. Immunol., 28, 1341–1345

Primrose and Old, Principles of Gene Manipulation, Blackwell, Oxford, 1980.

Queen, C., Schneider, W. P., Selick, H. E., Payne, P. W., Landolfi, N. F., Duncan, J. F., Avdalovic, N. M., Levitt, M., Junghans, R. P., Waldmann, T. A., 1989. A humanized antibody that binds to the interleukin 2 receptor. Proc. Natl. Acad. Sci. USA., 86, 10029–10033

Queen, C., Selick, H. E., 1990. Chimeric immunoglobulins specific for p55 TAC protein of the IL-2 receptor. WO90/07861

Riechmann, L., Clark, M., Waldmann, H., Winter, G 1988. Reshaping human antibodies for therapy. Nature, 332, 323–327

Rolfe, M. R., Bebbington, C. R., 1992. Amplification using CHO cell expression vectors. In Ausubel, F. M., Brent, R., Kingston, R. C., Moore D. D., Seidman, J. G., Smith, J. A., Streuhl, K., (eds.) Current Protocols in Molecular Biology Routledge, E. G., Lloyd, I., Gorman, S. D., Clark, M. Waldmann, H. 1991. A humanized monovalent CD3 antibody which can activate homologous complement. Eur. J. Immunol., 21, 2717–2725

Saiki R. K., Scharf, S., Faloona, F., Mullis, K. B., Horn, G., Erlich, H. A., Arnheim, N., 1985. Enzymatic amplification of b-globin genomic sequences and restriction site analysis for diagnosis of sickle cell anemia. Science, 230, 1350–1354

Saleh, M. N., Khazaeli, M. B., Wheeler, R. H., Allen, L., Tilden, A. B., Grizzle, W., Reisfeld, R. A., Yu, A. L, Gillies, S. D., LoBuglio, A. F., 1992. Phase I trial of the chimeric anti-GD2 monoclonal antibody ch14.18 in patients with malignant melanoma. Hum. Antibod. Hybridomas, 3, 19–24

Sherff, S., Silverton, E. W., Padlan, E. A., Cohen, G. H., Smith-Gill, S. J., Finzel, B. C., Davies, D. R., 1987. Three-dimensional structure of an antibody-antigen complex Proc. Natl. Acad. Sci. USA., 84, 8075–8079

Skerra, A., Pluckthun,A., 1989. Assembly of a functional immunoglobulin Fv fragment in *Escherichia coli*. Science, 240, 1038–1041

Trang, J. M., LoBuglio, A. F., Wheeler, R. H., Harvey, E. B., Sun, L., Ghrayeb, J., Khazaeli, M. B., 1990. Pharmacokinetics of a mouse/human chimeric monoclonal antibody (C-17-1 A) in metastatic adenocarcinoma patients. Pharmacol. Res., 7, 587–592

Travers, P., Bodmer, W., 1984. Preparation and characterization of monoclonal antibodies against placental alkaline phosphatase and other human trophoblast-associated determinants. Int. J. Cancer., 33, 633–641

Verhoeyen, M., Broderick, L., Eida, S., Badley, A., 1991. Reshaped human anti-PLAP antibodies in Epenetos, A. A.(ed.) Monoclonal antibodies Applications in clinical oncology Pub. Chapman and Hall Medical pp37–43

Vernoeyen, M., Milstein, C., Winter, G., 1988. Reshaping human antibodies: Grafting an antiiysozyme activity. Science, 239, 1534–1536

Welt, S., Divgi, C. R., Real, F. X., Yeh, S. D., Pilar, G. C., Finstad. C. L., Sakamoto, J., Cohen, A., Sigurdson, E. R., Kemeny, N., Carswell, E. A., Oettgen, H. F., Old. L. J., 1990. Quantitative analysis of antibody localisation in human metastatic colon cancer: Studies with monoclonal antibody A33. J. Clin. Oncol., 8, 1894–1896

Whittle, N., Adair, J., Lloyd, C., Jenkins, L., Devine, J., Schiom, J., Raubitshek, A., Coicher, D., Bodmer, M., 1987. Expression in COS cells of a mouse/human chimaeric B72.3 antibody. Prot. Eng., 1, 499–505

Winter, G. P., 1987. Recombinant antibodies and methods for their production. EP-0239400

Wu, T. T., Kabat, E. A., 1970. An analysis of the sequences of the variable regions of Bence Jones proteins and myeloma light chains and their implications for antibody complementarity. J. Exp. Med., 132, 211–250

What is claimed is:

1. A humanized antibody molecule (HAM) having specificity for the epitope recognized by the murine monoclonal antibody A33 (MAb A33), wherein said HAM comprises:

(1) the light chain variable region comprising amino acids 28 to 135 of SEQ ID NO: 46;

(2) the heavy chain variable region comprising amino acids 27 to 143 of SEQ ID NO: 55; and (3) remaining immunoglobulin-derived parts of the HAM being derived from a human immunoglobulin, said HAM being optionally conjugated to an effector or reporter molecule.

2. A HAM according to claim 1, wherein said human immunoglobulin is selected from the group consisting of human framework sequences for both the heavy and light chains of LAY, POM, KOL, REI, EU, TUR, TEI, NEWM.

3. A HAM according to claim 2, wherein the framework sequence is LAY.

4. A multivalent monospecific antigen-binding protein comprising two three, four or more HAMs according to claim 1 or fragments thereof, bound to each other by a connecting structure, said antigen binding protein being optionally conjugated to an effector or reporter molecule, wherein the connecting structure is the residue of a cross-linking agent of formula (1):

$$R^1CH(R^2)NHCOR^3$$

wherein $R^1$ is a carboxyl or esterified carboxyl or carboxamide group or a group —COA where A is an effector or reporter molecule attached to the —CO group either directly or via a spacer group to form a carbon-carbon, or carbon-hetero atom linkage; $R^2$ and $R^3$, which may be the same or different, is each an optionally substituted straight or branched alkylene, alkenylene, or alkynylene chain containing one or more reactive functional groups such that the total number of reactive functional groups in $R^2$ and $R^3$ together is two, three or more.

5. A multivalent antigen-binding protein according to claim 4, which comprises three Fab fragments bound to each other by a connecting structure.

6. A HAM according to claim 1, wherein the effector or reporter molecule is a radionuclide or complexed radionuclide.

7. A HAM according to claim 6, wherein the radionuclide is radioiodine.

8. A HAM according to claim 6, wherein the complexed radionuclide is a chelated radionuclide selected from the group consisting of $^{99m}$Tc, $^{186}$Re, $^{188}$Re, $^{58}$Co, $^{60}$Co, $^{67}$Cu, $^{195}$Au, $^{199}$Au, $^{110}$Ag, $^{203}$Pb, $^{206}$Bi, $^{207}$Bi, $^{111}$In, $^{67}$Ga, $^{68}$Ga, $^{88}$Y, $^{90}$Y, $^{160}$Tb, $^{153}$Gd and $^{47}$Sc, chelated with a polydentate chelating agent.

9. A HAM according to claim 8, wherein the radionuclide is $^{111}$In or $^{90}$Y.

10. A multivalent antigen-binding protein comprising at least three Fab' fragments of the HAM of claim 1.

11. A multivalent antigen-binding protein comprising two, three, four or more Fab' fragments of the HAM of claim 1.

12. A multivalent antigen-binding protein according to claim 4, wherein said fragments comprise two, three, four or more Fab' fragments.

13. A multivalent antigen-binding protein according to claim 4, wherein said fragments comprise three Fab' fragments.

14. A multivalent antigen-binding protein according to claim 4, wherein said human immunoglobulin is selected from the group consisting of human framework sequences for both the heavy and light chains of LAY, POM, KOL, REI, EU, TUR, TEI, NEWM.

15. A multivalent antigen-binding protein according to claim 14, wherein the framework sequence is LAY.

16. A multivalent antigen binding protein according to claim 4, wherein the effector or reporter molecule is a radionuclide or complexed radionuclide.

17. A multivalent antigen binding protein according to claim 16, wherein the radionuclide is radioiodine.

18. A multivalent antigen binding protein according to claim 16, wherein the complexed radionuclide is a chelated radionuclide selected from the group consisting of $^{99m}$Tc, $^{186}$Re, $^{188}$Re, $^{58}$Co, 60CO, $^{67}$CU, $^{195}$Au, $^{199}$Au, $^{110}$Ag, $^{203}$Pb, $^{206}$Bi, $^{207}$Bi, $^{111}$In, $^{67}$Ga, $^{68}$Ga, 88 Y, $^{90}$Y, $^{160}$Tb, $^{153}$Gd and $^{47}$Sc, chelated with a polydentate chelating agent.

19. A multivalent antigen binding protein according to claim 18, wherein the radionuclide is $^{111}$In or $^{90}$Y.

* * * * *